United States Patent
Hsieh et al.

(10) Patent No.: US 12,364,429 B2
(45) Date of Patent: Jul. 22, 2025

(54) COMPOSITIONS AND METHODS FOR A UNIVERSAL CLINICAL TEST FOR OLFACTORY DYSFUNCTION

(71) Applicant: The Rockefeller University, New York, NY (US)

(72) Inventors: Julien Wen Hsieh, Geneva (CH); Andreas Keller, Astoria, NY (US); Leslie Birgit Vosshall, New York, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 0 days.

(21) Appl. No.: 18/160,624

(22) Filed: Jan. 27, 2023

(65) Prior Publication Data

US 2023/0172525 A1    Jun. 8, 2023

Related U.S. Application Data

(63) Continuation of application No. 16/628,075, filed as application No. PCT/US2018/040704 on Jul. 3, 2018, now abandoned.

(60) Provisional application No. 62/528,420, filed on Jul. 3, 2017.

(51) Int. Cl.
*A61B 5/00* (2006.01)

(52) U.S. Cl.
CPC ...... *A61B 5/4011* (2013.01); *A61K 2800/591* (2013.01)

(58) Field of Classification Search
CPC .... A61B 5/4011; A61K 2800/591; C11B 9/00
See application file for complete search history.

(56) References Cited

U.S. PATENT DOCUMENTS

| | | |
|---|---|---|
| 5,800,897 A | 9/1998 | Sharma et al. |
| 6,844,302 B1 | 1/2005 | Boden et al. |
| 8,545,724 B2 | 10/2013 | Braun et al. |
| 2007/0077204 A1 | 4/2007 | Devanand et al. |
| 2011/0177522 A1 | 7/2011 | Hung et al. |
| 2014/0221269 A1 | 8/2014 | Sobel et al. |
| 2017/0119032 A1 | 5/2017 | Senomyx |

FOREIGN PATENT DOCUMENTS

| | | |
|---|---|---|
| EP | 2174585 A1 | 4/2010 |
| EP | 2753367 A1 * | 7/2014 |
| EP | 2792302 A1 | 10/2014 |
| WO | 2016/161261 A1 | 10/2016 |

OTHER PUBLICATIONS

Hummel, T. et al., 'Sniffin Sticks': Olfactory Performance Assessed by the Combined Testing of Odor Identification, Odor Discrimination and Olfactory Threshold, Chemical Senses, Jan. 1997, vol. 22, No. 1, pp. 39-52.
Keller, A. et al., Olfactory perception of chemically diverse molecules, BMC Neuroscience, 2016, vol. 17, No. 55, 17 pages.

* cited by examiner

*Primary Examiner* — Kimberly Ballard
*Assistant Examiner* — Stacey N MacFarlane
(74) *Attorney, Agent, or Firm* — Hodgson Russ LLP

(57) ABSTRACT

Disclosed are compositions and methods for measuring olfactory sensitivity, olfactory resolution, and combinations thereof. Such measurements can be made during a single test, or over consecutive tests, which may be performed during a single testing period, such as in a single day, or over a series of testing periods. The tests may be performed by a health care professional, or may be conveniently self-administered by the user.

3 Claims, 13 Drawing Sheets

COMPOSITIONS AND METHODS FOR A UNIVERSAL CLINICAL TEST FOR OLFACTORY DYSFUNCTION

CROSS REFERENCE TO RELATED APPLICATIONS

This application is a continuation of U.S. application Ser. No. 16/628,075, filed on Jan. 2, 2020, which is a National Phase of International Application No. PCT/US2018/040704, filed on Jul. 3, 2018, which claims priority to U.S. Provisional Application No. 62/528,420, filed on Jul. 3, 2017, the disclosures of each of which are hereby incorporated by reference.

STATEMENT REGARDING FEDERALLY SPONSORED RESEARCH

This invention was made with government support under grant no. UL1 TR000043 awarded by National Institutes of Health. The government has certain rights in the invention.

FIELD OF THE DISCLOSURE

The disclosure generally relates to compositions and methods of sensory diagnosis and/or repair.

BACKGROUND OF THE DISCLOSURE

Smell dysfunction manifests itself primarily in the reduced ability to detect or identify volatile chemicals, and ranges from the complete inability to smell any odors, to a partial reduction in olfactory sensitivity, to smell distortion, for instance that a large number of odors smell like cigarette smoke. The prevalence of smell dysfunction in the general adult population is about 20% in Europe and the United States (1-3). This condition is dangerous because those affected are unable to detect fire, spoiled food, hazardous chemicals, and leaks of odorized natural gas (4, 5). Smell loss also has severe health consequences, including mental health symptoms such as depression, anxiety, and social isolation. It affects quality of life by altering food preferences and the amount of food ingested (5). Food is often perceived as bland or tasteless by patients with smell disorders, leading to loss of appetite or overeating (4, 5).

Smell dysfunction has many causes, including head trauma, upper respiratory tract infection, nasal polyps, and congenital anomalies (6, 7). In many cases, the cause of smell dysfunction is unknown (5, 8). Importantly, smell dysfunction is an early sign of Alzheimer's disease (9), the most common cause of dementia in the United States that is projected to affect an estimated 1 in every 45 individuals by 2050 (10). There is growing evidence that diminished olfactory function arises early in the progression of Alzheimer's disease, and is highly predictive of future cognitive decline (3, 4). Because of the high prevalence and dramatic consequences of smell loss, accurate diagnosis of olfactory dysfunction is important. While self-reported hearing loss tends to be accurate (11), self-reporting of olfactory dysfunction is notoriously unreliable. Therefore, accurate diagnostic tests for smell dysfunction that can be deployed worldwide are critically important. Following a diagnosis, therapeutic options and counselling can be offered to patients suffering from smell loss (12).

In clinical smell testing, patients are presented with odor stimuli in a variety of formats, including scratch 'n' sniff strips, glass vials or jars, felt-tip pens, or paper scent strips used in perfume shops, and asked to answer questions about what they smell. Smell tests assess the ability of subjects to detect, discriminate, or identify odors. Olfactory threshold tests measure the lowest concentration of an odor stimulus that a patient can perceive, while discrimination tests assess the ability of subjects to distinguish two different smells. Finally, odor identification tests evaluate whether a patient can detect and match odors to standard words that describe the smell (13).

There are at least two major challenges to reliably testing a patient's sense of smell. First, sensitivity to monomolecular odorants varies greatly even among subjects with a normal sense of smell (14-16). All commercial smell tests that use monomolecular odorants therefore run the danger of misdiagnosing patients. For instance, when a patient has a low score on a test that assesses olfactory sensitivity with the rose-like odor phenyl ethyl alcohol (17), it is difficult to know whether the patient suffers from general smell dysfunction, or is merely insensitive to phenylethyl alcohol with an otherwise normal sense of smell.

The second challenge is to develop a test that is not influenced by the patient's prior olfactory experiences. This has an obvious influence on the results of odor identification tests such as the University of Pennsylvania Smell Identification Test (UPSIT) for which subjects are given a booklet with 40 scratch 'n' sniff items and asked to select one of four words (for example "gingerbread", "menthol", "apple", or "cheddar cheese") that best describes what the odor smells like. Whether a patient can correctly identify the smell of gingerbread depends not only on the patient's sense of smell, but also on whether the patient has previously encountered the smell of gingerbread. This in turn depends on many factors such as the cultural and age group the patient belongs to. To address this familiarity problem, the UPSIT has been adapted for use in a number of countries worldwide by replacing unfamiliar items and adapting the answers on the multiple-choice test. For instance, the North American UPSIT was adapted for Taiwanese subjects by replacing "clove", "cheddar cheese", "cinnamon", "gingerbread", "dill pickle", "lime", "wintergreen", and "grass" with "sandalwood", "fish", "coffee", "rubber tire", "jasmine", "grapefruit", "magnolia", and "baby powder" (18). The strong influence of prior olfactory experience on the test results limits the utility of odor identification tests. Even performance on non-semantic odor discrimination tasks depends on prior experience with the odorants (19, 20), and it is therefore important to avoid stimuli having differential familiarity in the test population. Thus, there is an ongoing and unmet need to develop new compositions and methods for assessing olfactory function. The present disclosure is pertinent to this need.

SUMMARY OF THE DISCLOSURE

The present disclosure provides compositions, kits, and methods for determining olfactory sensitivity and olfactory resolution. The disclosure provides distinct ensembles of odorants that can be used in making such determinations. In some embodiments, odorants are provided in a plurality of dilutions, such as serial dilutions, such that iterative exposure to the distinct dilutions provides for quantifying and/or scoring olfactory sensitivity and/or resolution. In one non-limiting approach, the lowest concentration of an odor stimulus that a subject can perceive is determined, and used to provide a value for olfactory sensitivity. In another non-limiting approach, a subject's capacity to distinguish distinct smells from one another is quantified and/or scored to provide a value for olfactory resolution. Certain aspects of olfactory resolution and/or sensitivity can be assessed using a variety of experimental designs, a non-limiting example of which comprises a triangle test, whereby the capacity of an individual to determine the presence or absence of an olfactory stimulus, and/or to discriminate between distinct olfactory stimuli, is analyzed.

In embodiments, a value determined using an approach described herein can be used to assist in a diagnosis of an olfactory defect, and/or another condition or disorder that is correlated with olfactory sensory acuity, for example, by determining a sensitivity and/or resolution value that is lower or different from a threshold or reference value.

In embodiments, methods of the disclosure can comprise performance of triangle tests. Triangle tests are known to those skilled in the art as a discriminative approach used in sensory science to determine the presence or absence of a stimulus, and/or a difference between distinct samples, such as by asking a subject to select one of three stimuli that is different from the other two.

Kits comprising combinations of odorants described herein are also provided.

BRIEF DESCRIPTION OF THE FIGURES

For a fuller understanding of the nature and objects of the disclosure, reference should be made to the following detailed description taken in conjunction with the accompanying figures.

and SMELL-R (v2) (D). (E) Cross-population comparison of UPSIT and SMELL-R (v2) (mean±95% confidence interval) for subjects in (C,D).

Figure 6:
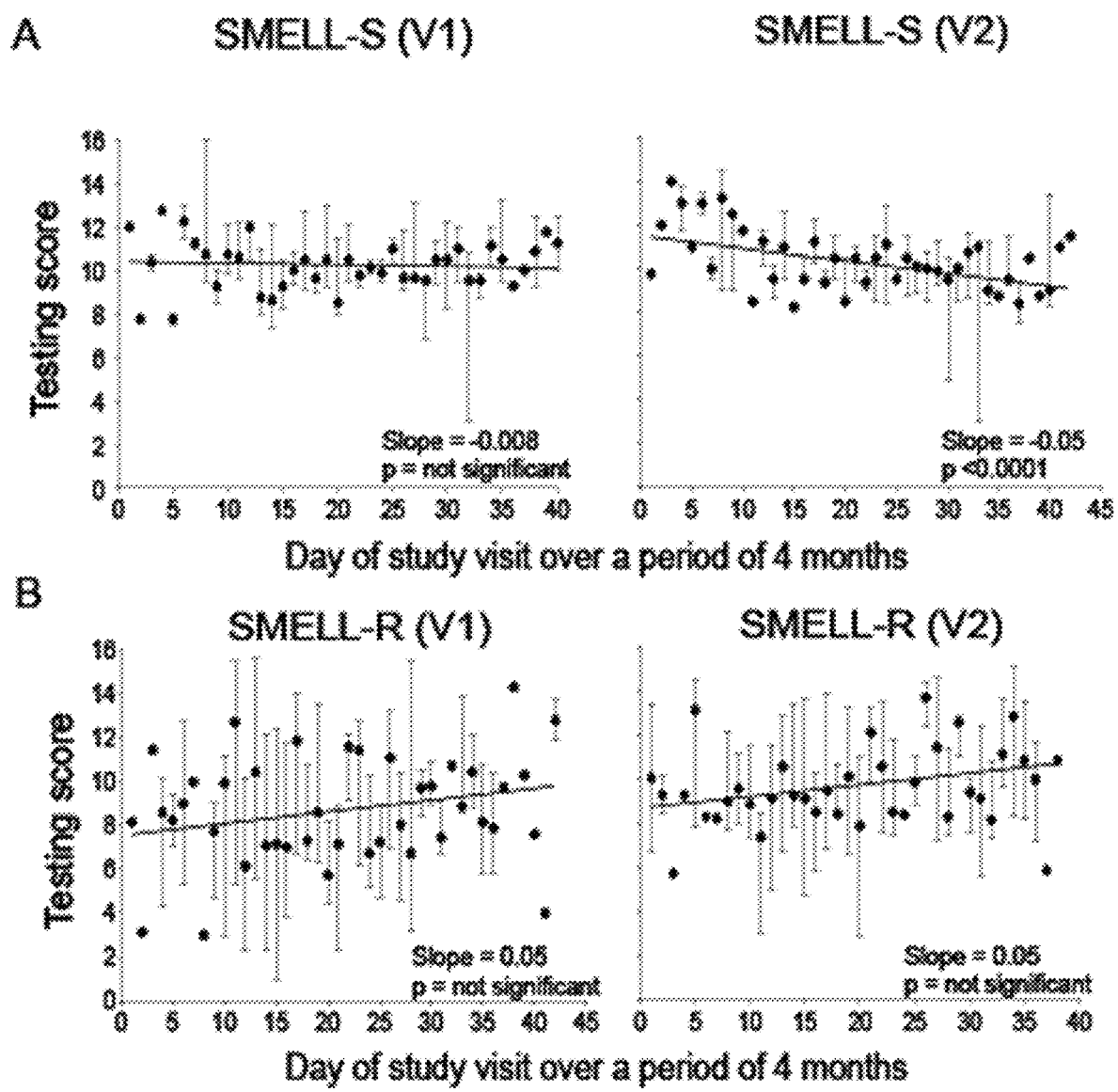

FIG. 6 shows SMELL-S (panel A) and SMELL-R (panel B) stimuli are stable over 4 months of testing. To calculate the stability of SMELL-S (panel A) and SMELL-R (panel B), the median and interquartile range of testing score per study visit day were plotted. The slope of the data was fitted by linear regression, and analyzed for significant difference from a slope of zero, which would correspond to perfect stability across the testing period. Stimuli for each test were freshly made only once at the beginning of the study, stored at room temperature in a ventilated lab, and used throughout the study. Study visit days took place 2-3 times a week. We tested 75 subjects who performed each one of the 4 tests twice.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various changes may be made without departing from the scope of the disclosure.

Every numerical range given throughout this specification includes its upper and lower values, as well as every narrower numerical range that falls within it, as if such narrower numerical ranges were all expressly written herein.

The disclosure includes all method steps and compositions of matter described herein in the text figures and tables of this disclosure, including all such steps individually and in all combinations thereof. The disclosure includes all compositions of matter including but not necessarily limited to every combination and sub-combination of compounds described herein, all dilutions of the compounds, all compound mixtures, all compound ratios, and all combinations of compound combinations that may be provided in single containers, or more than one container, and sets of compounds provided in single and separate containers. Containers are defined as the vehicle by which stimuli are presented to the subject, and can comprise a solid or liquid formulation in a vial or jar; a scratch 'n' sniff scent strip; a solid or liquid formulation in a device that produces a vapor or aerosol of the stimuli. The stimuli can be delivered manually by the subjects manipulating the container and sniffing, or digitally by a device that automatically delivers the stimuli to the subject. In embodiments, a mixture of compounds described herein can be provided in a semi-solid composition, including but not limited to a wax. In embodiments, mixtures that are present in, for example, a wax, can be provided as a component of a device, such as a disk, or cartridge. In embodiments, the disclosure includes a system comprising one or more disks or cartridges that comprise a mixture of compounds described herein in a liquid, semi-solid, or solid medium. In embodiments, the system allows for production and/or dissemination to a user of a vapor, such as in the presence of a drift, such as an air drift.

The compound combinations can comprise or consist of any of the compounds listed for any combination thereof, and my further include buffers or diluents that, for example, do not impact the olfactory system of a subject undergoing testing using the compounds. The disclosure includes a proviso that any compound or combination of compounds can be excluded from the claims of this application or patent, including but not necessarily limited to those compounds disclosed herein as "excluded" wherein the exclusion is for any reason, including but not limited to lateralization score or intensity-matching, or a combination thereof. Compounds of this disclosure are provided with compound identifiers (CID) which are the permanent identifier for a unique chemical structure as curated in PubChem, a project of the National Center for Biotechnology Information (NCBI) of the US government. All of the information in the associated PubChem database for each of the CIDs in this disclosures is incorporated herein by reference as of the filing date of this application or patent. In embodiments, compositions comprising any combination of compounds described herein remain stable over a period of time, such as from seven days, to at least a period of twelve months, including all days and intervals of days there between. In embodiments, the combinations of compounds are stored at room temperature and remain stable. In embodiments, stability is determined by the combination of compounds remaining suitable for using in a method described herein. In an embodiment, stability is determined as described for FIG. 6, which demonstrates determining stability of SMELL-S (FIG. 6, panel A) and SMELL-R (FIG. 6, panel B) tests, by plotting the median and interquartile range of testing score per study visit day. The slope of the data was fitted by linear regression (but other statistical methods that will be apparent to those skilled in the art could also be used) and analyzed for significant difference from a slope of zero, which would correspond to perfect stability across the testing period.

The disclosure includes measuring olfactory sensitivity, olfactory resolution, and combinations thereof. Such measurements can be made during a single test, or over consecutive tests, which may be performed during a single testing period, such as in a single day, or over a series of testing periods. The tests may be performed by a health care professional, or may be conveniently self-administered by the user. The tests thus involve methods for evaluating the olfactory function of an individual. The methods generally comprise allowing a subject to nasally inhale odorants from any combination of compounds and/or series of compound combinations described herein such that a determination of the sensitivity and/or the resolution capability of the olfactory function of the individual is made. The disclosure includes assigning threshold and/or score values to the olfactory function of the individual, as further described herein. In certain aspects the disclosure includes using the compound combinations described herein to assess olfactory function and generate one or more scores or other values that represent olfactory sensitivity, olfactory resolution, and/or combinations thereof. The disclosure includes use of control combinations of compounds and comparing perception of smell of test combinations to perception of smell to the control combinations.

In certain embodiments, the disclosures provides for integration of the testing procedures described herein with adaptive software to develop one or more thresholds and/or scores for olfactory sensitivity and/or resolution. Thus, embodiments of the disclosure can in part be implemented by a device comprising a microprocessor running software to perform one or more calculations described herein. In embodiments, the disclosure includes an application (i.e., an app) that can guide a user through one or a series of tests described herein, and whereby the test results can be entered into the app and one or more threshold values or scores can be generated and presented to the user via a user interface. Such apps can be configured to run on a computer connected to a bar code scanner, or any mobile device, such as a mobile phone or a tablet that can scan a QR code with a camera. In an embodiment, the software/app interfaces with a scent delivery device that controls the release of the stimuli, wherein the stimuli comprise a combination of compounds as described herein. In embodiments, the disclosure comprises a distributed system in a networked environment.

In certain embodiments the invention facilitates determination of the lowest concentration of an odor stimulus that a subject can perceive, and thus provides for generating a value for olfactory sensitivity. In alternative or complementary embodiments the invention facilitates analysis of a subject's ability to distinguish distinct smells from one another, and thus provides a value for olfactory resolution. In embodiments, methods of the disclosure can comprise performance of triangle tests. Triangle tests are known to those skilled in the art as a discriminative approach used in sensory science to determine the presence or absence of a stimulus, and/or a difference between distinct samples, such as by asking a subject to select one of three stimuli that is different from the other two.

In certain aspects of this disclosure, subjects are tested using a series of odorant combinations, which may or may not be presented using a triangle test approach, to determine which of a series of test combinations of odorants can be perceived using, for instance, serial dilutions of combinations of odorants, until a threshold is reached wherein no smell can be perceived. In certain aspects of this disclosure, subjects are tested to determine which of a series of test combinations of odorants are different from a reference combination, such as by removal or replacement of one or more odorants from a series of odorant combinations, until a threshold is reached, wherein difference in smell between a sample and a reference cannot be detected.

In an embodiment, a triangle test may comprise a test using three unknown samples to determine whether or not an individual can determine which sample is distinct from the others, i.e., the individual is provided samples XXY, which represents three compounds or combinations of compounds or dilutions thereof, to the individual, and the individual is tested to determine whether or not the individual can identify Y as distinct from samples XX.

Figure 1:
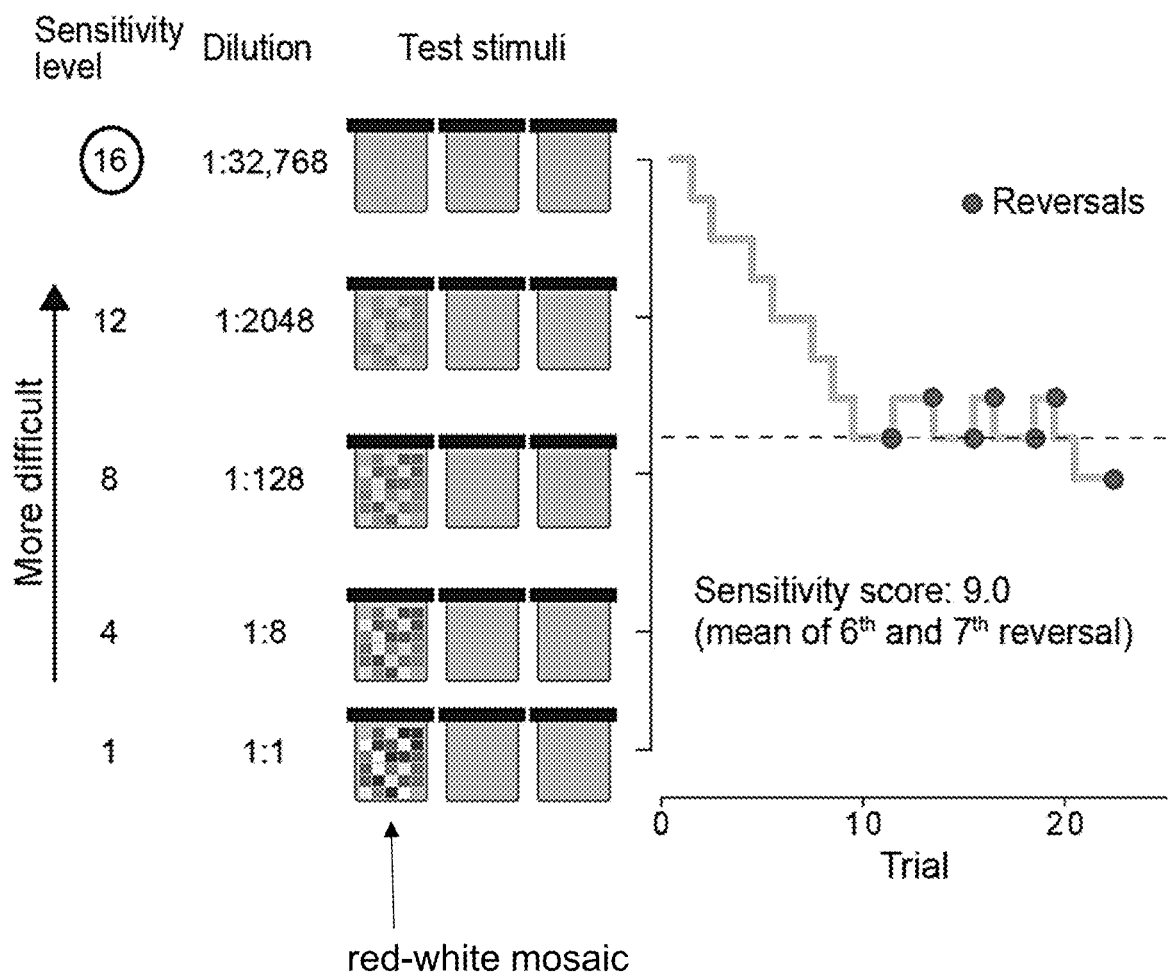
FIG. 1 shows SMELL-S olfactory sensitivity and SMELL-R olfactory resolution tests. (A) Schematic of triangle test stimuli for SMELL-S, comprising two glass vials containing solvent (gray) and one containing increasingly diluted mixtures of 30 molecules (red-white mosaic). Olfactory sensitivity of a subject measured with SMELL-S [Subject Expt 1-A023, SMELL-S (v2)]. (B) Schematic of triangle test stimuli for SMELL-R, comprising two jars containing the same mixture of 30 molecules (red-white mosaic) and a one containing mixtures of 30 molecules (black-gray mosaic) with an increasing number of molecules shared with the other two. Olfactory resolution of a subject measured with SMELL-R [Subject Expt 1-A016, SMELL-R (v1)]. Circles in A and B indicate starting level for each test.
Figure 1:
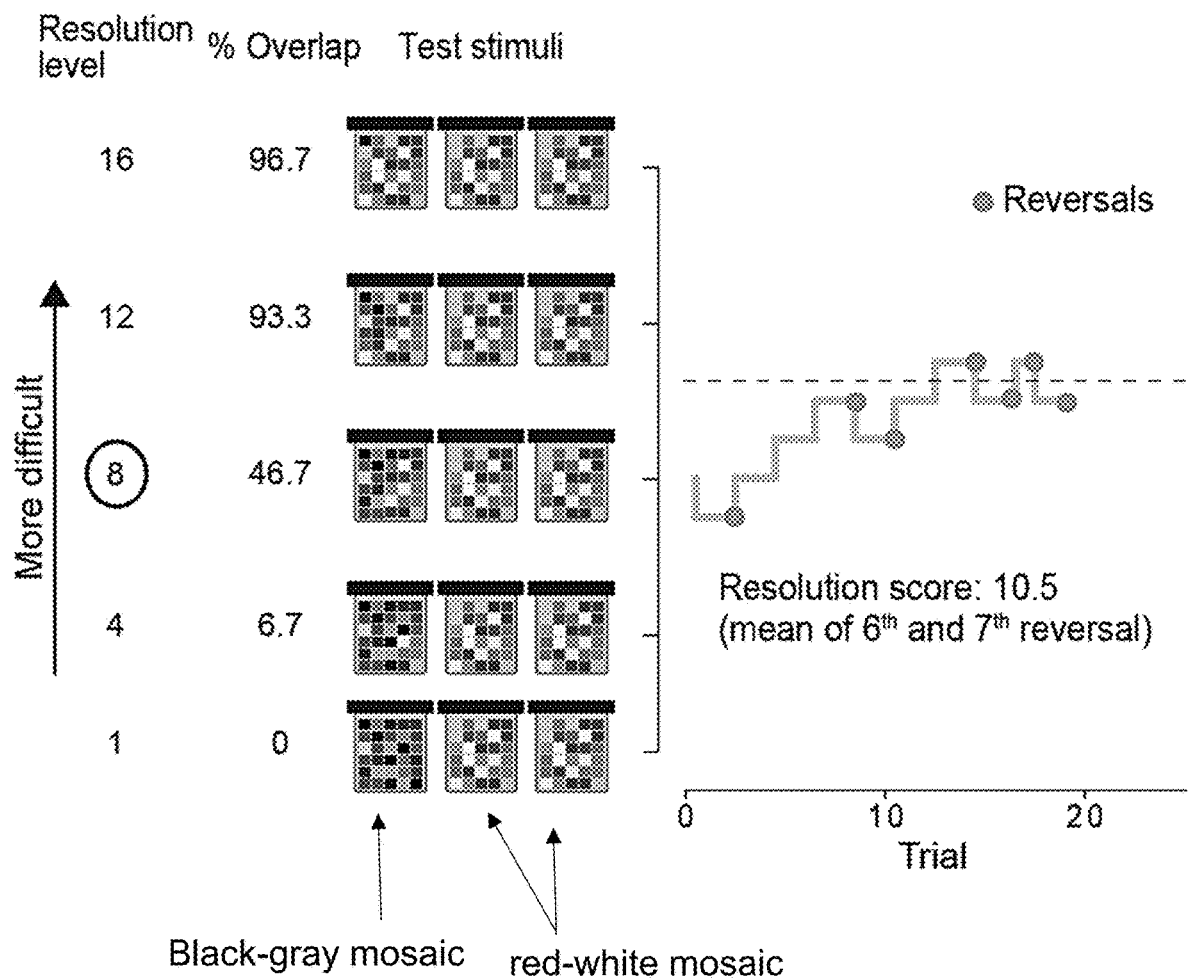

Non-limiting embodiments of the disclosure are generally outlined in FIG. 1, wherein panel A in FIG. 1 depicts an approach to determining olfactory sensitivity, and wherein FIG. 1, panel B, presents an approach to determining olfactory resolution. All steps and combinations of steps depicted in the figures of this disclosure are included within its scope. All dilution values described herein, whether or not depicted in the figures, are encompassed within this disclosure. All possible combinations of compounds listed Supporting Data Set 1 and all other tables provided herein are encompassed by this disclosure. Any single compound, or any combination of compounds described herein, can be excluded from the claims.

In embodiments the disclosure provides for determining a threshold score that is at least in part calculated using a reversal, wherein a reversal comprises a change in the direction of the concentration used for the test, i.e., the subject who is nasally inhaling samples with increasing concentrations is subsequently provided a decreased concentration, or vice versa. In embodiments, more than one reversal point can be attained in order to determine a threshold value. In certain embodiments, from 1-7 reversals are attained. In embodiments, a threshold value is determined when a subject cannot detect a particular high concentration of odorants at least twice, or the subject detects a particular low concentration of odorants more than one time. A threshold value can be the same as, or used in establishing a score for the individual. In an embodiment, a score can be determined using reversals in combination with concentration values where one, or a series, or an average of concentration values where reversal(s) occurred are used. In embodiments, an individual is assigned a score of from 1-16, wherein 16 indicates the individual is able to correctly identify low concentrations of odorants, whereas a score of 1 indicates the individual was not able to identify high concentrations of odorants. Such thresholds and scores can be used for determining olfactory sensitivity, and can be adapted for determining olfactory resolution. For example, standard staircase procedures can be used, given the benefit of the present disclosure, to determine a subject's ability to discriminate between different combinations of compounds that can be, for example, altered in a stepwise fashion to become increasingly similar or dissimilar to each other, and/or to test the capability of an individual to detect a sample that is dissimilar from other sample(s), such as is generally outlined in FIG. 1B.

In certain approaches the compositions, kits and methods of this disclosure are broadly applicable to geographically and culturally distinct populations of human individuals, and to individuals over a variety of ages. Thus, the disclosure removes difficulties of, for example, semantic-based smell tests that include biases based on lack of prior exposure to an odorant, and/or an inability to verbalize a characteristic of an odorant due to geographical, cultural, or linguistic influences or experience. In particular, the present disclosure provides smell tests that use mixtures of molecules that average out the variability in sensitivity to individual molecules. Because these mixtures have unfamiliar odors, and the tests are non-semantic, their use eliminates differences in test performance due to the familiarity with the smells or the words used to describe them. Thus, the tests facilitate smell testing of diverse populations, without the need to adapt the test stimuli.

In certain approaches the compositions and methods of this disclosure are used to test a human individual who is diagnosed with, suspected of having, or is at risk for developing one or more sensory and/or cognitive disorders. In embodiments, the individual is at risk for developing a cognitive disorder that comprises memory loss, and/or dementia. In embodiments the disclosure is used to aid in diagnosis of such a disorder, and may moreover contribute to earlier diagnosis than has been possible before the development of the present invention. In embodiments the disorder is Alzheimer's disease, or is a post-concussion syndrome, or Chronic Traumatic Encephalopathy (CTE). In certain and alternative embodiments, the disclosure aids in diagnosis of hyposmia, anosmia, parosmia, or phantosmia. Additional conditions that the compositions and methods of this disclosure may assist in the diagnosis of include but are not necessarily limited to: inflammatory nasal and sinus diseases, such as those caused by postviral olfactory dysfunction, chronic rhinosinusitis with nasal polyps, chronic rhinosinusitis without nasal polyps; nasal tumors, including esthesioneuroblastoma, adenocarcinoma, respiratory epithelial adenomatoid hamartoma; neurodegenerative diseases including Parkinson's Disease and Huntington's Disease; normal aging; toxic exposure to chemicals in the industrial workplace; congenital syndromes affecting the sense of smell, including Kallmann Syndrome, Kartagener Syndrome, Isolated Congenital Anosmia; brain tumors, including olfactory groove meningioma or temporal lobe neoplasia; systemic diseases, including diabetes, alcoholism, liver failure, renal failure, hypothyroidism, systemic lupus erythematosus; and psychiatric disorders, including depression or schizophrenia. Thus, in embodiments, a result obtained from performing a method of this disclosure may provide a diagnosis, or aid in a healthcare provider's diagnosis, of any of the foregoing conditions.

In embodiments, the compositions and methods of this disclosure can aid in monitoring a treatment for one or more conditions. In a non-limiting embodiment, an individual can be evaluated with an initial test or set of tests described herein to establish baseline values for olfactory sensitivity and/or olfactory resolution. The individual can subsequently be re-tested after, for example, a period of therapy for a disorder, and if the individual exhibits an improvement in a value for olfactory sensitivity and/or olfactory resolution relative to the baseline it may be indicative that the particular therapy is effective. Conversely, if the individual exhibits worsening of a value for olfactory sensitivity and/or olfactory resolution relative to the baseline it may be indicative that the particular therapy is not effective. Similar approaches can be adapted to determine if, for example, a particular agent, such as pharmaceutical agent or environmental agent, is having an impact on the olfactory function of an individual. In other embodiments, the disclosure is suitable for evaluating whether an individual has suitable olfactory properties that relate to, for example, a particular occupation wherein sense of smell is important for safety or other reasons, including but not necessarily limited to the development of consumer and industrial products that produce or otherwise involve perception of distinct odors.

In view of the foregoing and the following description, figures and tables, it will be apparent to those skilled in the art that the present disclosure provides new non-semantic tests for olfactory sensitivity (SMELL-S) and olfactory resolution (SMELL-R) that overcome previous challenges by using mixtures of odorants that have unfamiliar smells. The tests can be self-administered with minimal training and exhibit high test-retest reliability. Because SMELL-S uses odor mixtures rather than a single molecule, odor-specific insensitivity is averaged out. Indeed, SMELL-S accurately distinguished people with normal and dysfunctional smell. SMELL-R is a discrimination test in which the difference between two stimulus mixtures can be altered stepwise. This is an advance over current discrimination tests, which ask subjects to discriminate monomolecular odorants whose difference cannot be objectively calculated. SMELL-R showed significantly less bias in scores between North American and Taiwanese subjects than conventional semantically-based smell tests that need to be adapted and translated to different populations. It is expected that SMELL-S and SMELL-R will be broadly effective in diagnosing smell dysfunction, including that associated with the earliest signs of memory loss in Alzheimer's disease.

In embodiments, compounds used during testing according to this disclosure are provided to the subject in identical containers, with the proviso that coded indicia signifying to the test provider may be included to identify the composition of the compounds. In embodiments, at least two containers, or at least three containers are provided. At least one of the containers comprises a distinct combination of compounds, and/or a distinct dilution of compounds, relative to at least one other container. In embodiments, the containers are arranged in a particular order, such as a line, and the subject nasally inhales the sample from left to right, or right to left, or top to bottom, or bottom to top, etc. In embodiments, the subject identifies strongest odor (SMELL-S, as described below) or the odd odor (SMELL-R, as described below), or completes both tests.

In embodiments the disclosure provides combinations of the following compounds, which are also listed in the "Molecules Included" table that is part of the Supporting Data Set 1 that forms a part of this disclosure: butyraldehyde, cuminaldehyde, octanal, dihydrocoumarin, octanol, phenethylamine, pyruvic acid, methyl sulfide, 4-methyl-5-thiazoleethanol, decanoic acid, eugenol, 2-phenylethanol, dimethyl anthranilate, 2-isopropylphenol, 2-methoxy-4-methylphenol, carvyl acetate, furfuryl alcohol, α-methylbenzyl alcohol, acetophenone, methyl phenylacetate, diphenyl ether, α,α-dimethylbenzenepropanol, phenethyl acetate, 2-ethyl-1-hexanol, 4-methylanisole, ethyl propionate, diethyl malonate, ethyl butyrate, propyl butyrate, 3,7-dimethyl-1-octanol, (−)-citronellol, isoamyl butyrate, ethyl heptanoate, ethyl octanoate, propyl propionate, dimethyl succinate, methyl heptanoate, gamma-valerolactone, benzenethiol, butyl butyrate, butylamine, thiophene, ethyl decanoate, diethyl sebacate, valeraldehyde, piperidine, 2-octanone, heptanoic acid, propyl sulfide, heptanol, decanol, lauryl acetate, 2-hydroxyacetophenone, methyl anthranilate, p-tolyl acetate, 4-allylanisole, ethyl acetate, allyl heptanoate, nonanol, α,α-dimethylphenethyl acetate, 3-acetylpyridine, diethyl sulfide, 6-methyl-5-hepten-2-one, carvacrol, methyl propionate, butyl propionate, methyl 2-furoate, 5-methylfurfural, ethyl undecanoate, pentyl acetate, 2-decanone, 2-nonanone, decahydro-2-naphthol, undecane, 1,6-hexanedithiol, 2-acetyl-5-methylfuran, Isoamyl octanoate, allyl butyrate, terpinyl formate, 2-methoxy-3-methylpyrazine, hexyl hexanoate, ethyl 2-methylbutyrate, phenethyl propionate, p-anisaldehyde, ethyl hexanoate, allyl hexanoate, benzyl phenylacetate, 2-phenoxyethyl isobutyrate, butyl 10-undecenoate, methyl 2-methoxybenzoate, hexyl formate, 4-methyl-5-thiazoleethanol acetate, delta-undecalactone, ethyl-3-hydroxyhexanoate, 3-acetyl-2,5-dimethylfuran, 2-ethoxythiazole, 2-furanmethanethiol formate, 4-oxoisophorone, dihydrojasmone, whiskey lactone, 6-acetyl-1,1,2,4,4,7-hexamethyltetralin, 2-methyl-4-propyl-1,3-oxathiane, 2-acetyl-3,5(6)-dimethylpyrazine, omega-pentadecalactone, 3-octanone, phenethyl 2-furoate, 2-(1-methylpropyl)thiazole, 3-octyl acetate, and geraniol.

These compounds were intensity-matched and exhibited a lateralization score≤11, as described further herein. In embodiments, the disclosure includes combinations of that comprise or consist of at least 2, 3, 4, 5, 6, 7, 8, 9, 10, 11, 12, 13, 14, 15, 16, 17, 18, 19, 20, 21, 22, 23, 24, 25, 26, 27, 28, 29, or 30 of these compounds. Mixtures that include more than 30 compounds, whether or not they are the compounds described herein, are also included. In embodiments, the disclosure comprises combinations of these compounds, wherein the compounds are divided into more than one container. Any container suitable for holding the compounds, and whereby a human subject can access the container to smell its contents, is included in the disclosures. In embodiments, the container comprises a glass or plastic vessel which may comprise an attached or removal cover or cap. In embodiments the vessel is a jar, a tube, or a vial. In embodiments, the vessel comprises an absorbent material. In embodiments, the vessel comprises a digital scent delivery device that volatilizes or aerosolizes the stimuli from a solid or liquid form. In embodiments, the disclosure comprises combinations that contain all of compounds in the Molecules Included list below, wherein sets of the compounds, such as from 2-30 of the compounds, are divided into separate containers. In embodiments, the disclosures comprises sets of these compounds, wherein the compounds are diluted by a method and in a solvent appropriate for a given delivery system such as one or more dilutions obtained from a serial dilution.

In embodiments, the disclosure comprises any combination(s) or sets of combinations of compounds that are described in the "Table SMELL-R and SMELL-S Combinations" table that is part of the Supporting Data Set 1. In embodiments, one or more of the compounds are diluted as set forth in the SMELL-R and SMELL-S Combinations table.

In embodiments, the disclosure comprises kits. The kits can comprise one or more containers comprising any combination of compounds described herein, and may comprise empty containers for iterative tests, and/or for making compound dilutions for use in the methods described herein. The kits can include one or more solutions, such as for dissolving or suspending or dispersing any of the compounds described herein, and/or for diluting such compounds. The kits may comprise compound master mixes that are suitable for use directly, or for making dilutions and compound combinations as described herein. The kits can include printed material or a means for accessing web-hosted information that instructs the user how to perform the sensitivity and/or resolution tests described herein.

In one embodiment, the disclosure comprises fixing one or more results from a test described herein in a tangible medium of expression, and optionally communicating the test result to a database, and/or to a health care provider.

The following examples are intended to illustrate but not limit the invention.

Example 1

This example provides a description of smell tests: SMELL-S and SMELL-R.

To improve currently available diagnostic tools for testing olfactory function, and as outlined above, we created two new smell tests based on odorant mixtures. The Olfactory Sensitivity Test (SMELL-S) measures sensitivity to a mixture of 30 monomolecular odorants (FIG. 1A). The Olfactory Resolution Test (SMELL-R) measures the ability of subjects to discriminate the smell of such mixtures with an increase in overlapping components (FIG. 1B) (21, 22). Tests were presented in glass jars or vials as triangle tests, in which subjects were asked to pick out the stimulus with the strongest odor (SMELL-S) or the odd odor (SMELL-R). Both tests used adaptive staircase procedures that are standard in clinical olfactory testing (FIG. 1A, 1B) (23) (Hummel T, Sekinger B, Wolf S R, Pauli E, & Kobal G (1997) 'Sniffin' sticks': olfactory performance assessed by the combined testing of odor identification, odor discrimination and olfactory threshold. *Chem Senses* 22(1):39-52, the disclosure of which is incorporated herein by reference).

Test-Retest Reliability

Figure 2:
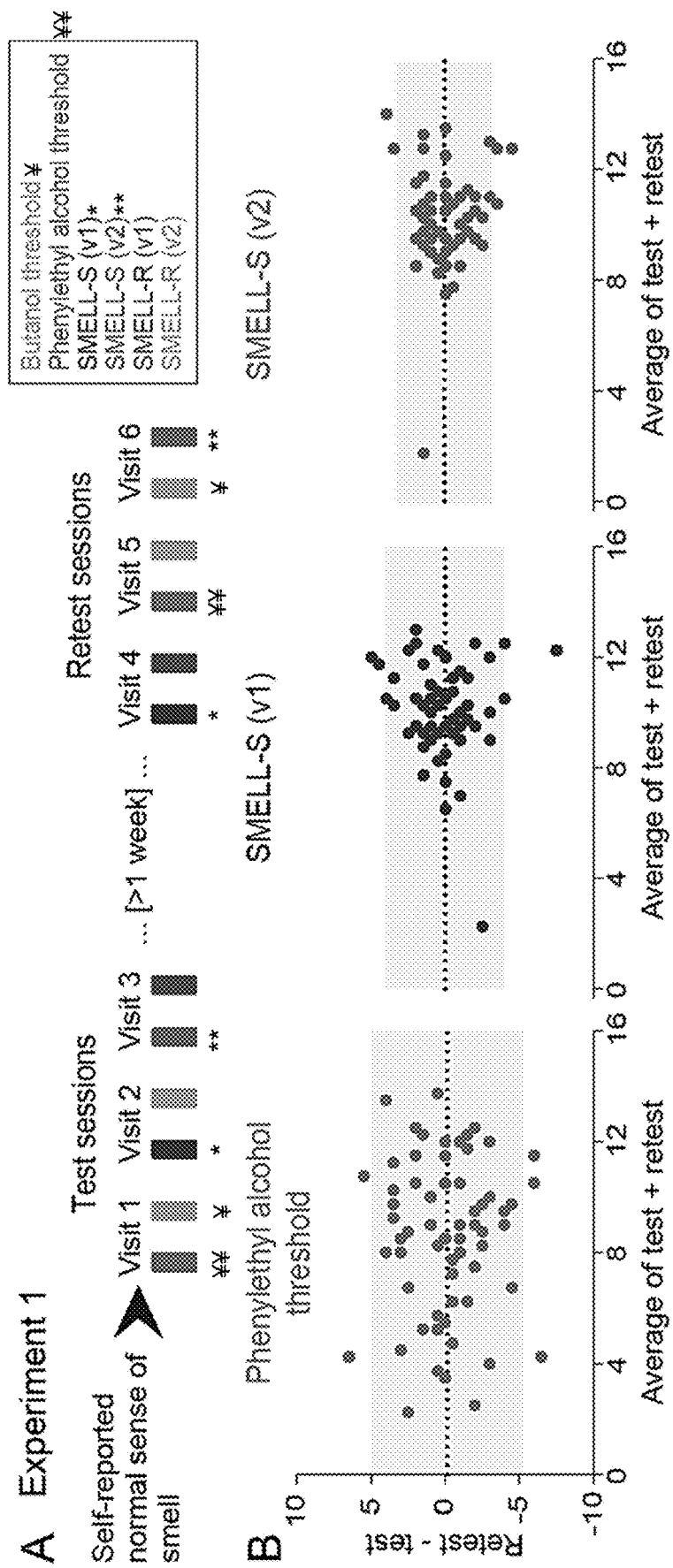
FIG. 2 shows test-retest reliability and relationship between SMELL-S and SMELL-R tests. (A) Experiment 1 design, showing one example of the many different presentations of the six smell tests. SMELL-R tests were always administered after SMELL-S or threshold tests in a given visit. (B) Bland-Altman plots of the indicated tests where each dot represents data from one subject. Black dotted lines represent the average of differences between retest and test scores, and gray areas indicate 95% limits of agreement (average difference±1.96 S.D. of the difference, n=74-75). (C) Test and retest scores for SMELL-R (v1) and SMELL-R (v2) where each dot represents data from one subject (ICC=intraclass correlation coefficient; n=73-75).
Figure 2:
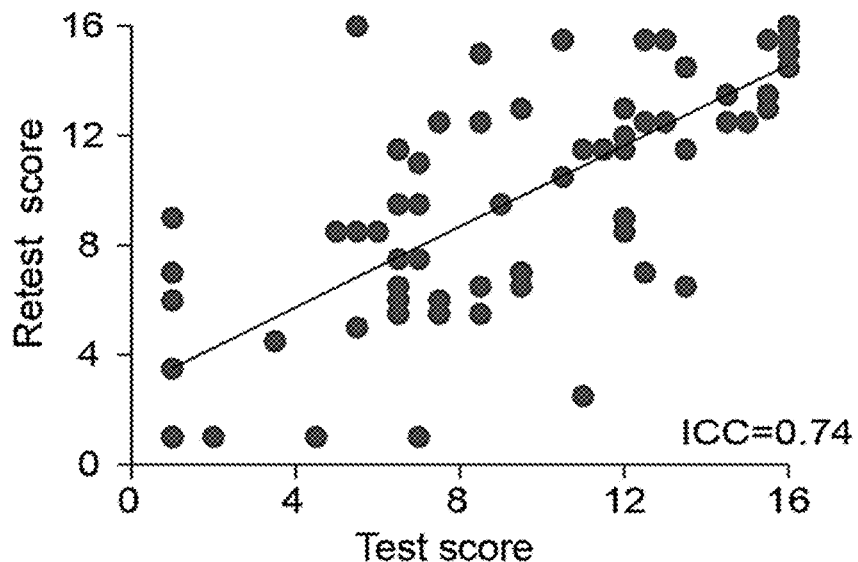
Figure 2:
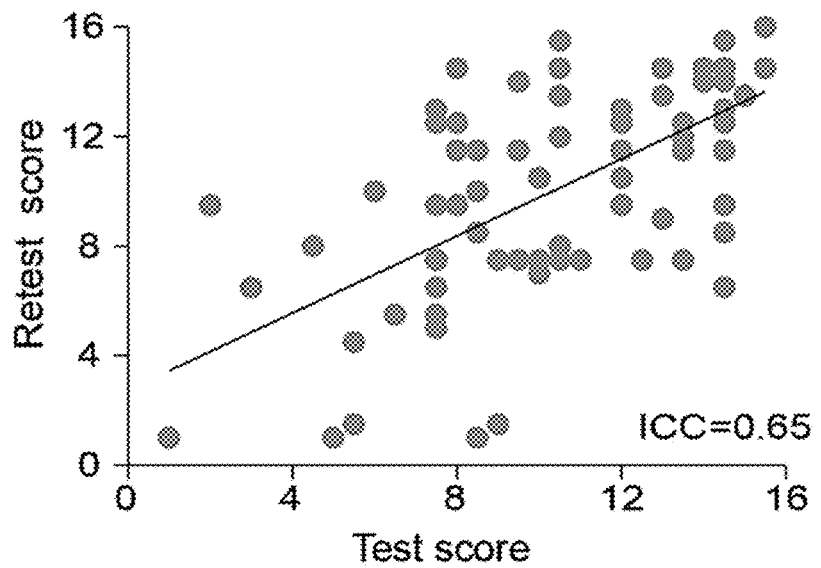

Effective diagnostic tests should be designed with high test-retest reliability. We therefore measured the reliability of SMELL-S and SMELL-R in a population of subjects with a self-reported normal sense of smell (Experiment 1; FIG. 2A). We tested two versions of SMELL-S and SMELL-R (v1 and v2) which are described in the Supporting Data set which is part of this disclosures, which differed in the 30 components used for the mixtures. We also carried out conventional threshold tests with the monomolecular odorants phenylethyl alcohol and butanol. All tests were self-administered with stimuli presented in glass jars. We excluded data from the butanol threshold test from analysis because the stimuli were not stable, as evidenced by a decline in average daily score for all subjects over the course of the four-month study (Supporting Data Set 1).

To assess test-retest reliability for SMELL-S, we computed the absolute difference in test-retest scores for each subject (FIG. 2B). The bias, as defined by the difference between the average of the test and retest scores, was close to zero for all three tests. This indicates that subjects did not show systematically different performance between the test and retest sessions. The 95% limits of agreement were much smaller for the two SMELL-S tests than the phenylethyl alcohol threshold test (FIG. 2B). We did not calculate test-retest correlations because of the large inter-individual variability of the phenylethyl alcohol threshold test compared to the two versions of SMELL-S (24). These results demonstrate that the SMELL-S test is more reliable than the phenylethyl alcohol threshold test. The phenylethyl alcohol threshold test is commercially available as Sniffin' Sticks, a well-validated test administered by clinical staff that utilizes felt-tip pens for odorant delivery (23, 25). To confirm that our self-administered phenylethyl alcohol threshold test presented in glass vials produced results comparable to Sniffin' Sticks, we re-invited 23 subjects from Experiment 1 and administered the Sniffin Sticks' version of the phenylethyl alcohol threshold test. There was a strong correlation between the phenylethyl alcohol threshold self-administered in glass vials and Sniffin' Sticks administered by a research assistant (r=0.87; 95% confidence interval: 0.72-0.95, Pearson correlation). This further confirms our conclusions that both versions of SMELL-S are more reliable tests of olfactory sensitivity than thresholds measured with phenylethyl alcohol.

We next examined the test-retest reliability of the SMELL-R test. Because the interindividual variability between SMELL-R (v1) (mean 9.3±4.3 standard deviation) and SMELL-R (v2) (mean 10.2±3.5 standard deviation) did not differ significantly (p=0.074, F test) (FIG. 2C), we calculated the intraclass correlation coefficient (ICC) for the SMELL-R tests. By this metric the two versions of SMELL-R are very reliable (FIG. 2C). Because SMELL-R (v2) had lower interindividual variability, we used this version of the test for the remaining experiments in the study.

Addressing the Problem of Odor-Specific Insensitivity

Smell tests that use a monomolecular stimulus like phenylethyl alcohol may misdiagnose a subject with odor-specific insensitivity to this odorant. A test based on mixtures of many components would overcomes this problem as described herein, because each odorant in the mixture has only a small impact on the overall test score (26). Such a test is expected to be highly effective in diagnosing general olfactory dysfunction, rather than variability in sensitivity to any individual odorant.

Figure 3:
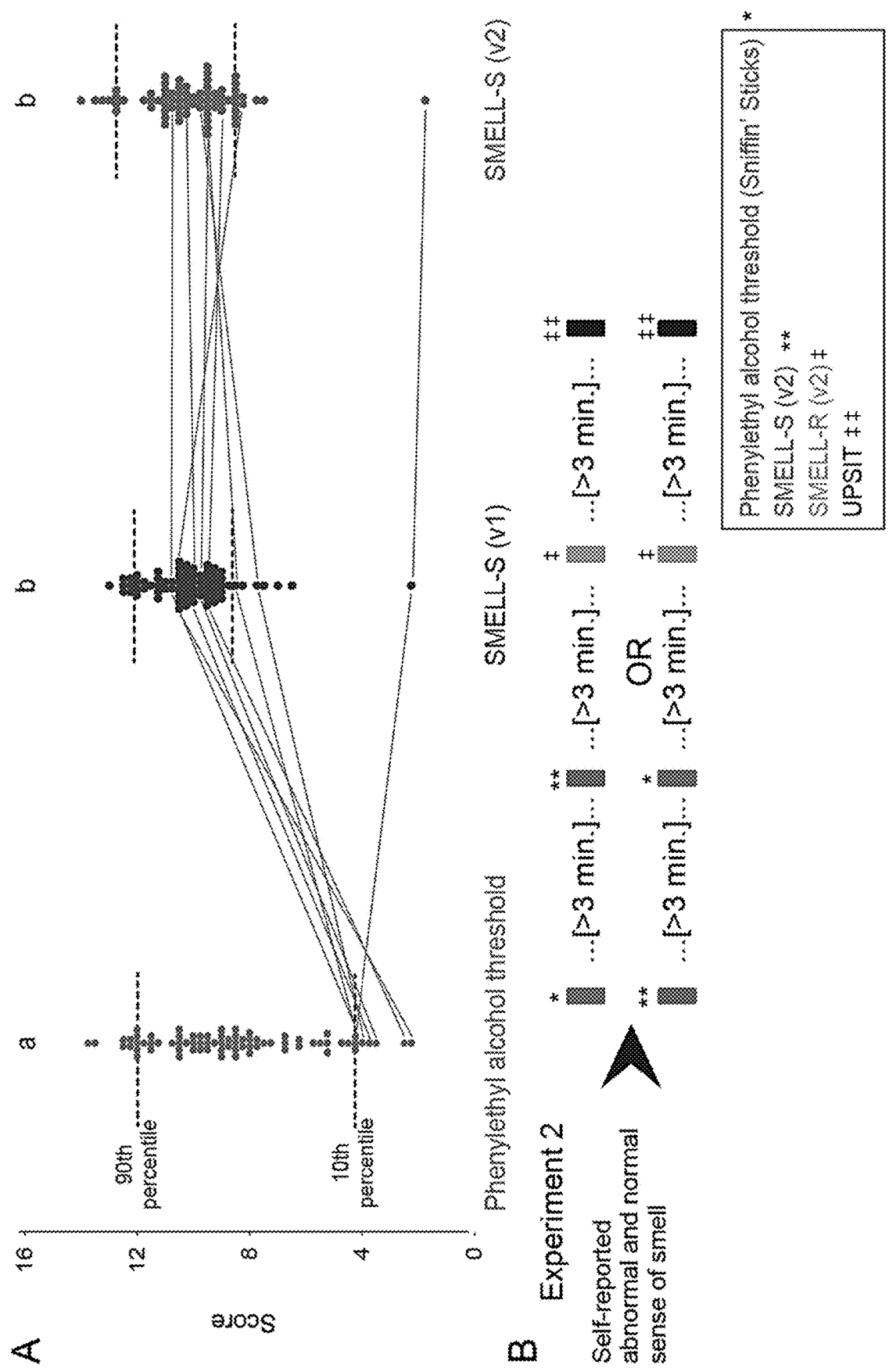
FIG. 3 shows addressing the problem of odor-specific insensitivity. (A) Subject average scores of the indicated tests from Experiment 1 between test and retest. Data marked with different letters indicate significantly different inter-individual variance between groups (p<0.0001; Conover squared ranks test, n=74-75). Data from the seven lowest-scoring subjects in the phenylethyl alcohol test are connected by lines. (B) Experiment 2 design. (C) The relationship between different etiologies of olfactory dysfunction and UPSIT scores in published studies, as well as of Experiment 2 subjects divided by self-reported smell abilities (mean±95% confidence interval). References: Korsakoff Syndrome (43), traumatic brain injury (45), sinonasal disease (45), Parkinson's Disease (46), postviral olfactory dysfunction (45), amnestic mild cognitive impairment (9), elderly at higher risk of cognitive decline (9), non-amnestic mild cognitive impaired (9), and toxic exposure (47). (D) UPSIT scores for subjects divided into normal and dysfunctional groups according to phenylethyl alcohol threshold (Sniffin' Sticks) (cut-off score=6.5) performance, where each dot represents data from one subject. Subjects scored as normal by the UPSIT but dysfunctional by Sniffin' Sticks phenylethyl alcohol test are colored in red in D and E. Data from the remaining subjects are colored brown here and in E. Data labeled with different letters are significantly different (p=0.0003, Mann-Whitney test). Medians and interquartile range are represented. (F) Comparison of UPSIT and phenylethyl alcohol (Sniffin' Sticks) scores. (F) UPSIT scores for subjects divided into normal and dysfunctional groups according SMELL-S (v2) (cut-off score=7) performance, where each dot represents data from one subject. Subjects scored as normal by the UPSIT but dysfunctional by Sniffin' Sticks phenylethyl alcohol test in D are colored red in F and G, while the others are in blue. Data labeled with different letters are significantly different (p<0.0001; Mann-Whitney test), and represented as median and interquartile range. (G) Comparison between UPSIT and SMELL-S (v2) scores. Subjects with identical values are indicated by superimposed open circles and an X, and retain the specified color coding.
Figure 3:
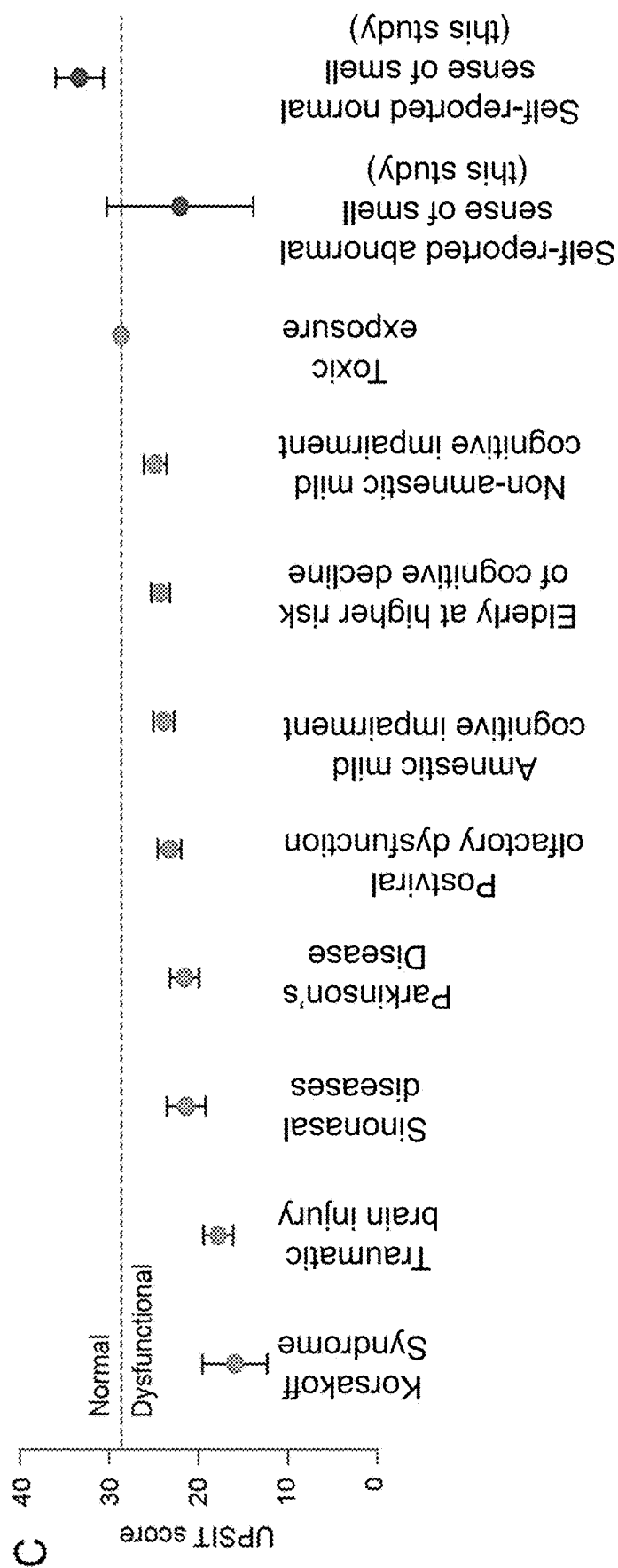
Figure 3:
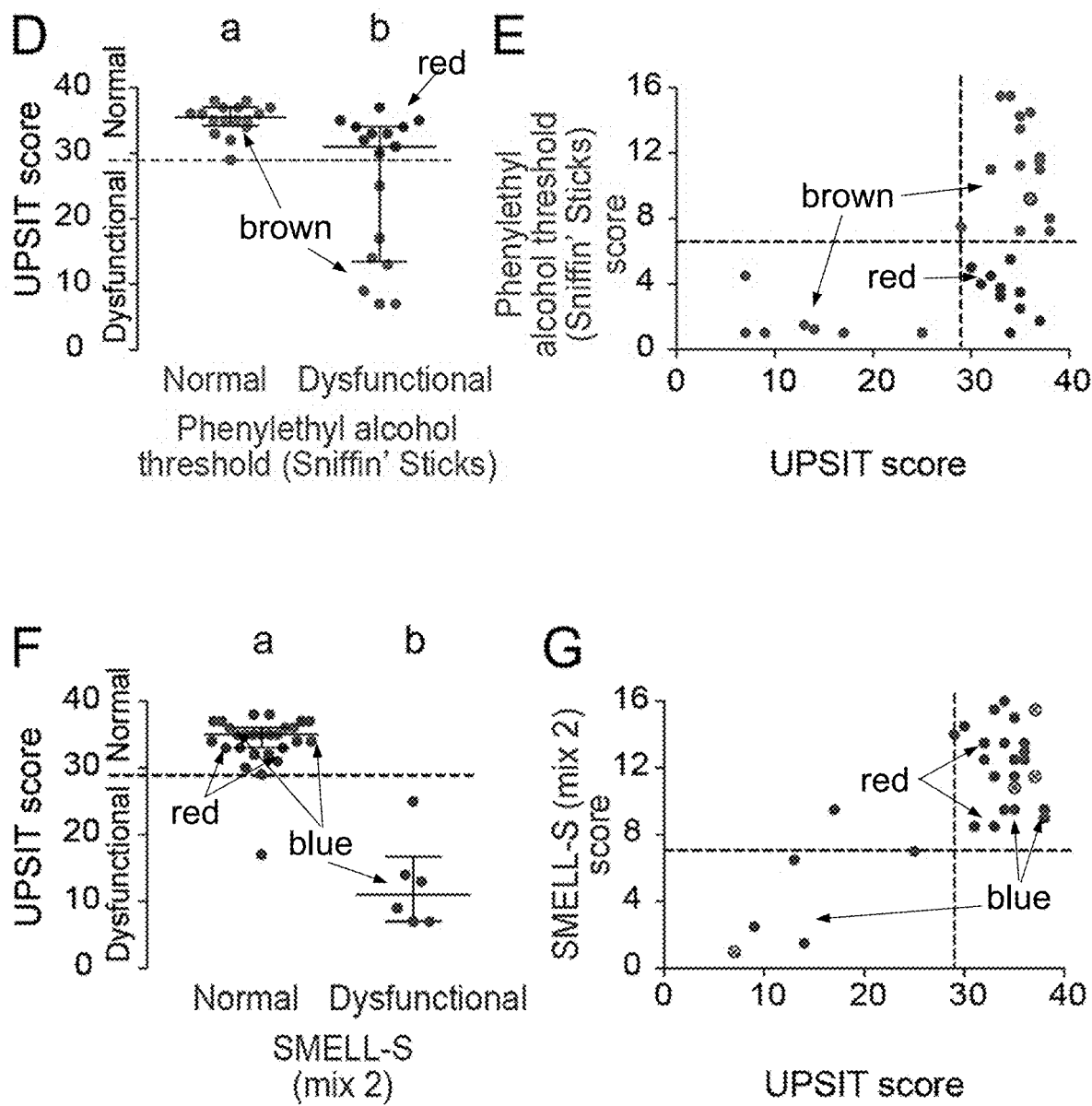

To explore how odor-specific sensitivity affects the accuracy of smell dysfunction diagnosis, we compared the performance of subjects in Experiment 1 on smell tests that used monomolecular stimuli or mixtures. The variability in test scores across all subjects in Experiment 1 of the phenylethyl alcohol threshold was significantly higher than that of SMELL-S (v1) and SMELL-S (v2) (FIG. 3A). Of the 7 subjects in the lowest $10^{th}$ percentile in the phenylethyl alcohol threshold test, only one was in the lowest $10^{th}$ percentile for both versions of SMELL-S. Without intending to be bound by any particular theory, we speculate that this subject has an impaired sense of smell. The low phenylethyl alcohol scores of the other 6 subjects likely reflect odor-specific insensitivity to odorant rather than impaired olfactory function. These subjects would have been misdiagnosed with smell dysfunction using the phenylethyl alcohol threshold test.

To confirm this, we compared the SMELL-S test with the Sniffin' Sticks phenylethyl alcohol threshold test and the North American version of the UPSIT (Experiment 2; FIG. 3B). Since SMELL-S (v2) had the narrowest 95% limits of agreement (FIG. 2B), we used this version of SMELL-S for the rest of this study. In Experiment 2, we assessed the performance of subjects with a self-reported normal or abnormal sense of smell on the UPSIT, Sniffin' Sticks, and SMELL-S (v2). Based on results in FIG. 3A, we anticipated that SMELL-S (v2) would be more accurate than the Sniffin' Sticks phenylethyl alcohol threshold test in identifying subjects with smell dysfunction. We used the UPSIT to benchmark the performance of the Sniffin' Sticks phenylethyl alcohol threshold test compared to SMELL-S (v2). Because this smell test is composed of 40 different items, the final score is not strongly affected by odor-specific insensitivity to any given stimulus among the 40 items of the test. To set a cut-off between normal and dysfunctional subjects, we performed a literature search on mean UPSIT scores in North American patients suffering from smell dysfunction caused by various etiologies. Based on this analysis and consistent with an earlier study (3), we defined normal olfactory function as an UPSIT score of 29 and over and smell dysfunction as an UPSIT score of 28 and lower (FIG. 3C). In Experiment 2, the mean score of the subjects with self-reported smell dysfunction was below this cut-off, whereas the mean score of those with self-reported normal sense of smell was above the cut-off (FIG. 3C). For the Sniffin' Sticks phenylethyl alcohol threshold test we used the cut-off specified by the manufacturer, with normal defined as a score higher than 6.5 and dysfunctional a score of lower than 6.5.

Figure 4:
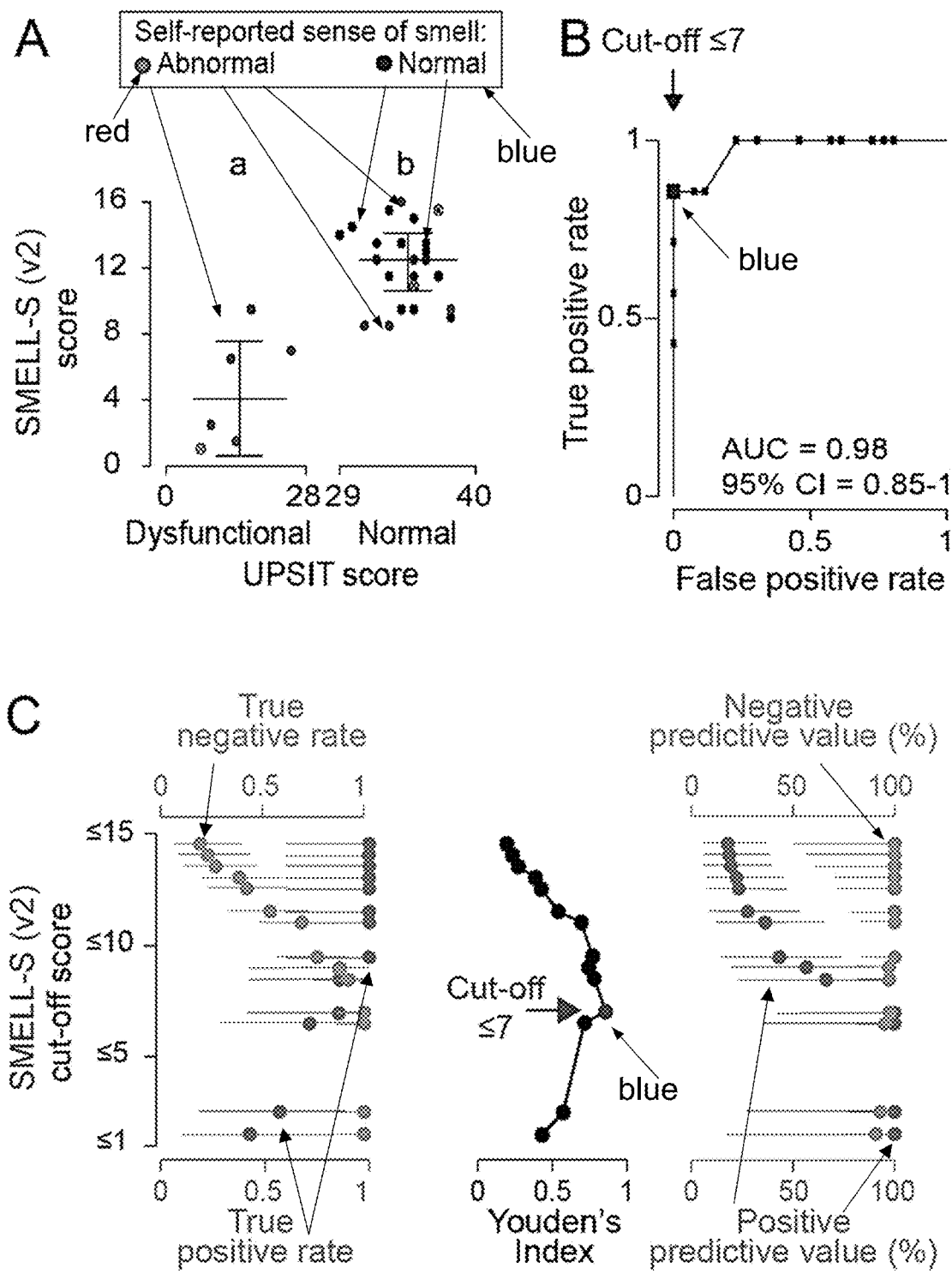
FIG. 4 shows SMELL-S and SMELL-R diagnostic accuracy. (A) Comparison of UPSIT and SMELL-S (v2) scores for Experiment 2 subjects (mean±S.D.) Subjects were divided into dysfunctional (n=7) and normal (n=26) using an UPSIT cut-off score of 29. Data labeled with different letters are significantly different (p=0.0005, two-sided unpaired t-test with Welch's correction). (B) Area under the ROC curve (AUC) for SMELL-S (v2). The optimal cut-off is indicated by the blue dot. (C) Plots of four measures of diagnostic accuracy resulting from different cut-off scores for SMELL-S (v2) (percentage±95% confidence interval). The optimal cut-off score for olfactory dysfunction defined by Youden's Index (center) is indicated by the blue dot. (D) Comparison of UPSIT and SMELL-R (v2) scores for Experiment 2 subjects (mean±S.D.) Subjects were divided into dysfunctional (n=7) and normal (n=26) using an UPSIT cut-off score of 29. Data labeled with different letters are significantly different (p=0.0035, two-sided unpaired t-test with Welch's correction). Subject Expt 2-A006 had a self-reported normal sense of smell but low scores on the UPSIT, as well as SMELL-S (v2) in A and SMELL-R (v2) in D. (F) Area under the ROC curve (AUC) for SMELL-R (v2). The optimal cut-off is indicated by the green dot. (F) Plots of four measures of diagnostic accuracy resulting from different cut-off scores for SMELL-R (v2) (rate or percentage±95% confidence interval). The optimal cut-off score for olfactory dysfunction defined by Youden's Index (center) is indicated by the green dot. Subjects with identical values are indicated by superimposed open circles and an X, and retain the specified color coding.
Figure 4:
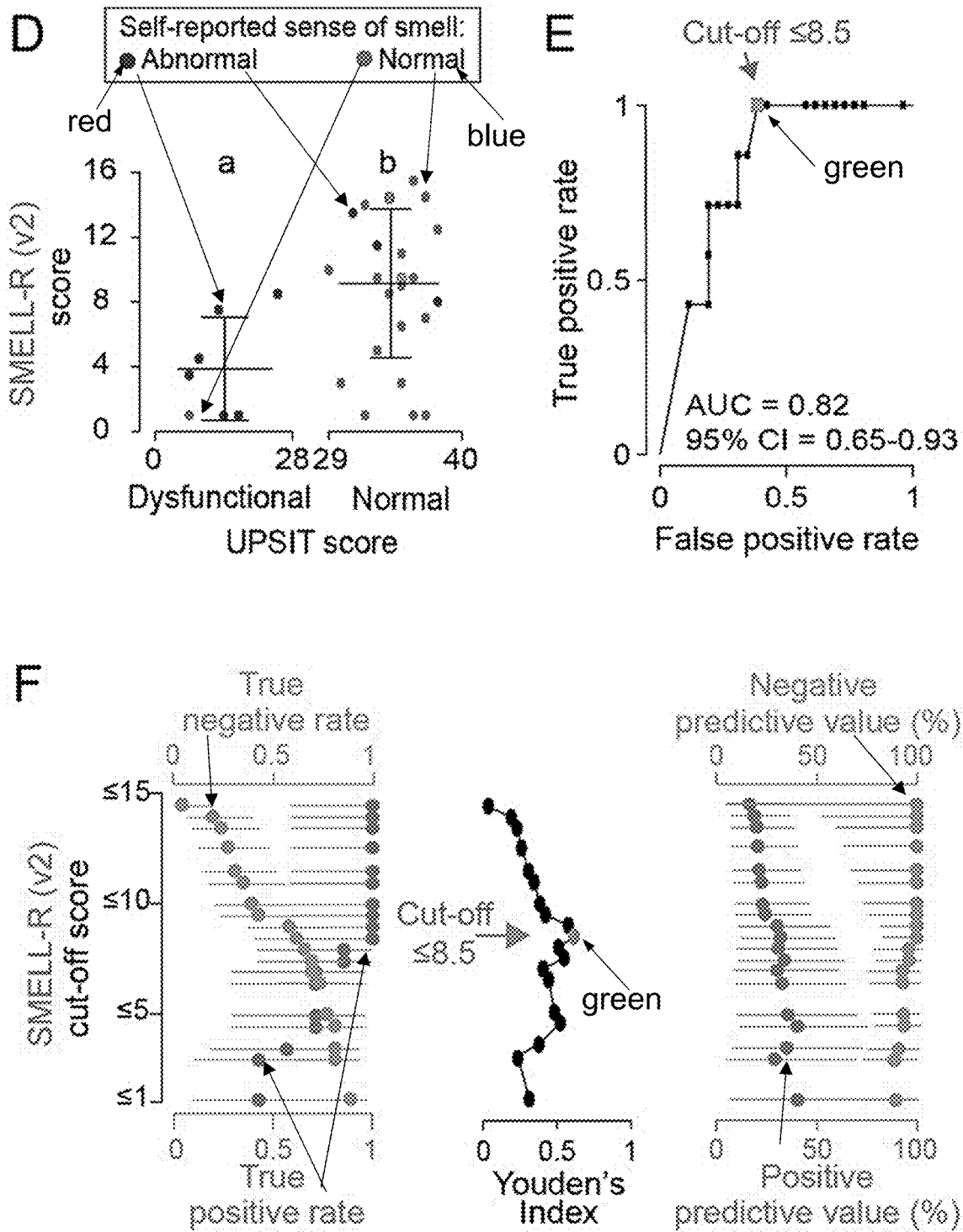

Subjects in Experiment 2 were divided into normal and dysfunctional according to their performance on the Sniffin' Sticks phenylethyl alcohol threshold test (FIG. 3D). Using the UPSIT cut-off score as a metric of olfactory dysfunction, 10 subjects would have been misdiagnosed as having olfactory dysfunction by the Sniffin' Sticks phenylethyl alcohol threshold test (FIG. 3D-G, red dots). When we divided subjects according to performance on the SMELL-S (v2) test using a cut-off score of 7 (see FIG. 4), we found that only one subject was given a different diagnosis using the UPSIT than with SMELL-S (v2) (FIG. 3F). This demonstrates that the SMELL-S (v2) test is superior to the Sniffin' Sticks phenylethyl alcohol threshold test in accurately diagnosing smell dysfunction. We conclude that odor-specific insensitivity to phenylethyl alcohol makes the Sniffin' Sticks phenylethyl alcohol threshold unreliable, and that the use of odor mixtures in SMELL-S (v2) overcomes this problem and is superior in accurately diagnosing smell dysfunction.

Diagnostic Accuracy

To be useful in the clinic, smell tests should correctly identify patients with smell dysfunction, and not misdiagnose normal subjects. In other words, diagnostic tests must balance false positive and false negative results. To establish a diagnostically optimal cut-off score for SMELL-S (v2) and SMELL-R (v2), we divided subjects into dysfunctional and normal using an UPSIT cut-off score of 29, and examined SMELL-S (v2) scores of self-reported normal and abnormal subjects in these two groups (FIG. 4A). Subjects with normal UPSIT scores had significantly higher SMELL-S (v2) scores than those that were dysfunctional (FIG. 4A). Subjects with a self-reported normal sense of smell (blue dots in FIG. 4A) had significantly higher SMELL-S (v2) scores (median, 12.5; interquartile range, 11-14) than whose with self-reported abnormal sense of smell (median, 7.75; interquartile range, 2.25-9.50) (red dots in FIG. 4A) (p=0.0011, Mann-Whitney test).

We next determined the overall accuracy of SMELL-S (v2), and selected an optimal cut-off score to differentiate normal and dysfunctional subjects (FIG. 4B-C). The standard measure of clinical test accuracy is the area under the receiver operating characteristic (ROC) curve, which plots the true and false positive rates at different cut-off scores. The area under the ROC curve of SMELL-S (v2) is 0.98 (95% confidence interval: 0.85-1.00) (FIG. 4B), which is close to the perfect accuracy of 1.

To select the cut-off value for SMELL-S (v2) that optimally distinguishes normal and dysfunctional subjects we calculated Youden's Index (27) at each of 14 SMELL-S (v2) cut-off scores. A Youden's Index value of 1 indicates no false positives and no false negatives. (FIG. 4C). Based on this analysis, the administration of SMELL-S (v2) with a cut-off value of 7 will be clinically useful for physicians to diagnose patients with olfactory dysfunction.

We carried out the same procedure to determine the accuracy of the SMELL-R olfactory resolution test. Subjects classified as dysfunctional by their UPSIT score had lower SMELL-R (v2) scores, and subjects classified as normal by UPSIT performance had a higher SMELL-R (v2) scores (FIG. 4D). The area under the ROC curve for SMELL-R (v2) was 0.82 (95% confidence interval: 0.65-0.93) (FIG. 4E). The optimal cut-off assessed by Youden's Index was 8.5 (FIG. 4F). These data show that SMELL-R at a cut-off value of 8.5 will be clinically useful for diagnosing smell dysfunction.

Addressing the Problem of Different Prior Olfactory Experiences

An aspect of this disclosure is the development of a test that does not have to be adapted to different populations. To ask if SMELL-R (v2) performs well in different countries, we compared SMELL-R (v2) performance between Taiwanese and North American subjects (Experiment 3, FIG. 5A). As a positive control we used the North American version of the UPSIT for both populations, because previous work has shown that Taiwanese subjects have systematically lower scores on this test due to unfamiliarity with several of the test items (18). To enable self-administration of the UPSIT we supplied Taiwanese subjects with a Chinese translation of the English multiple-choice questions in the test booklet. SMELL-R (v2) did not require any language translation because it is non-semantic.

Figure 5:
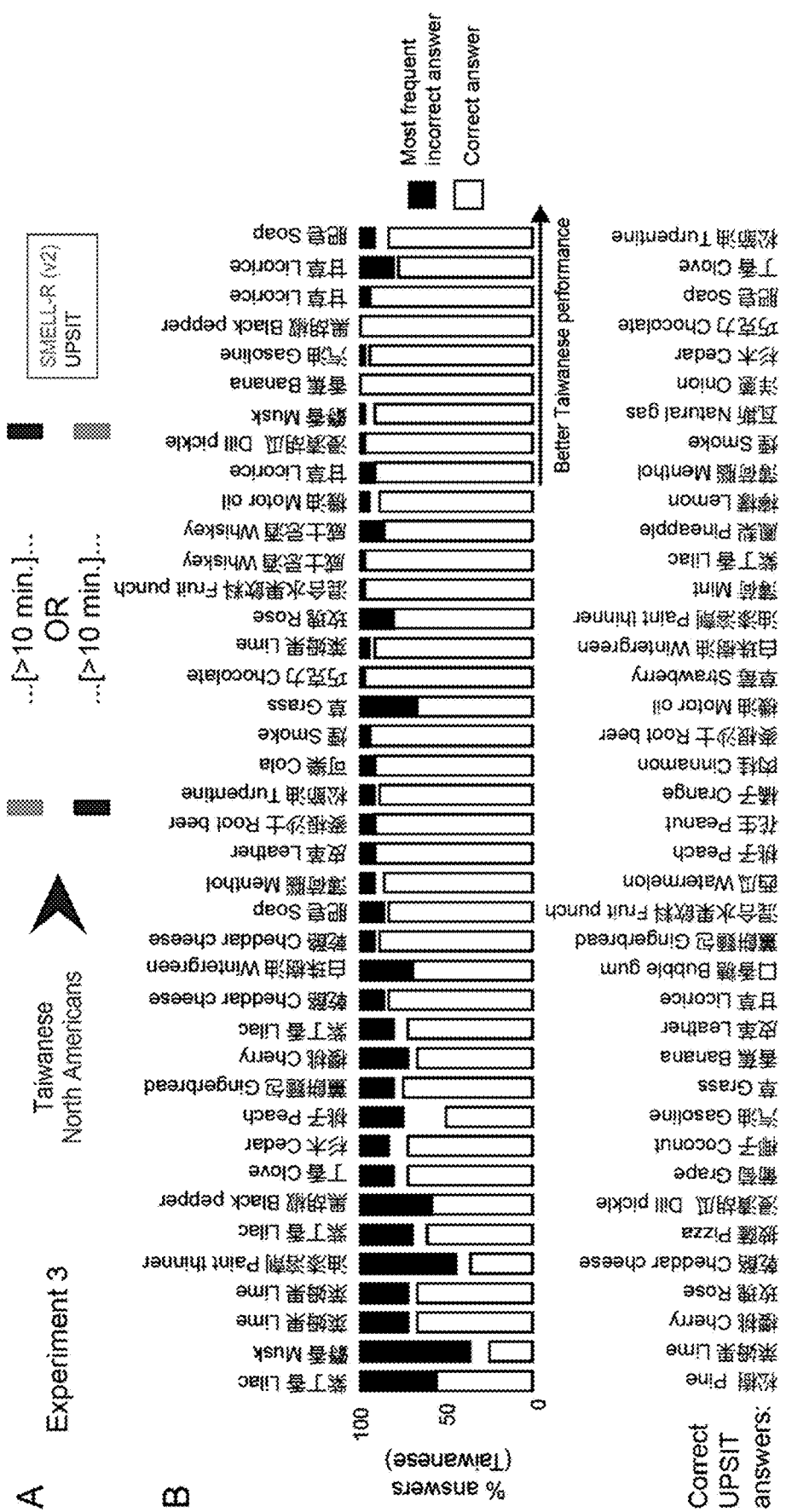
FIG. 5 shows addressing the problem of different prior olfactory experiences. (A) Experiment 3 design. (B) Performance of Taiwanese (n=36) (top) and North American (n=36) (bottom) subjects for individual UPSIT items, open bar bars indicate correct answers and solid bars indicate the most frequent incorrect answer. (CD) Histogram of North American and Taiwanese subject scores for the UPSIT (C)
Figure 5:
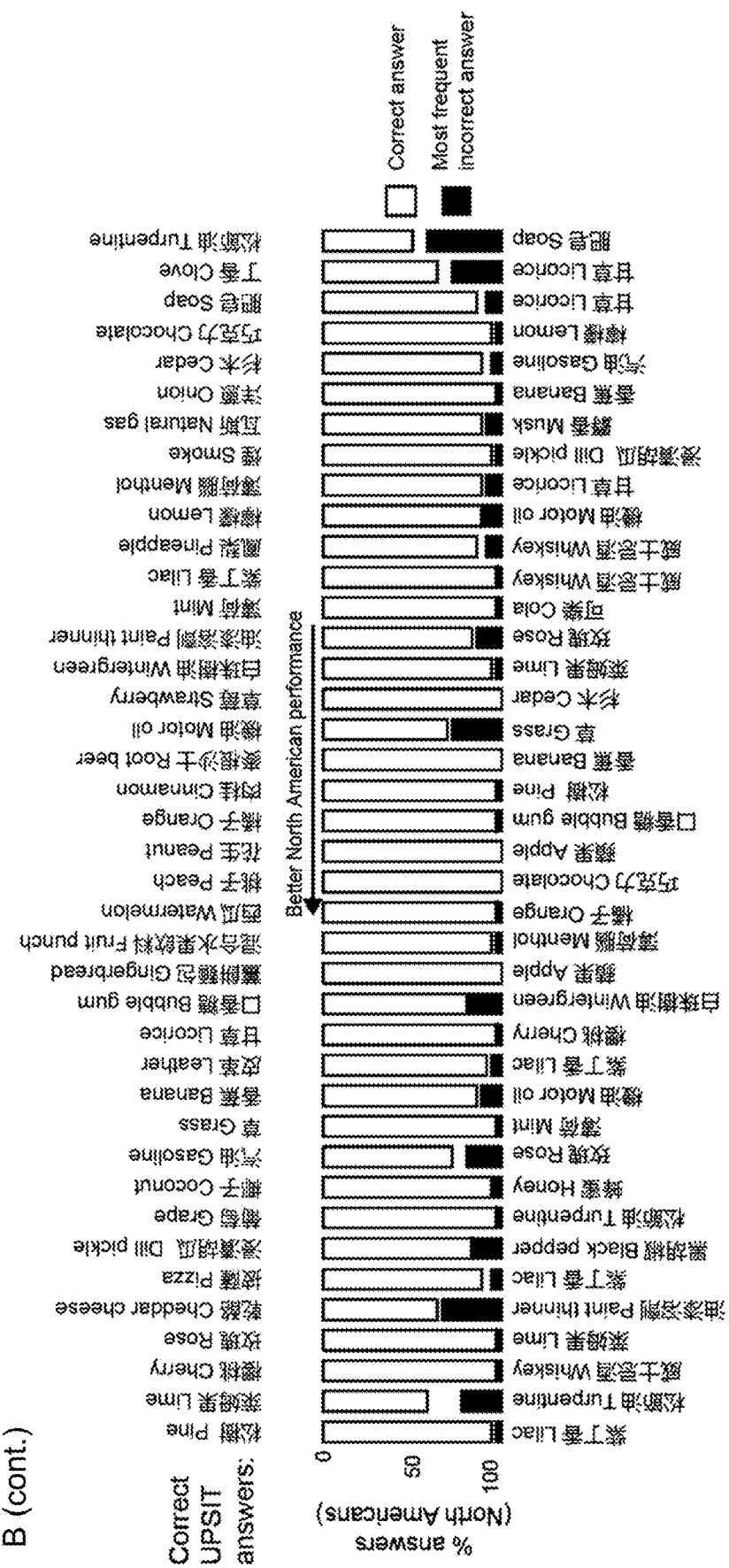
Figure 5:
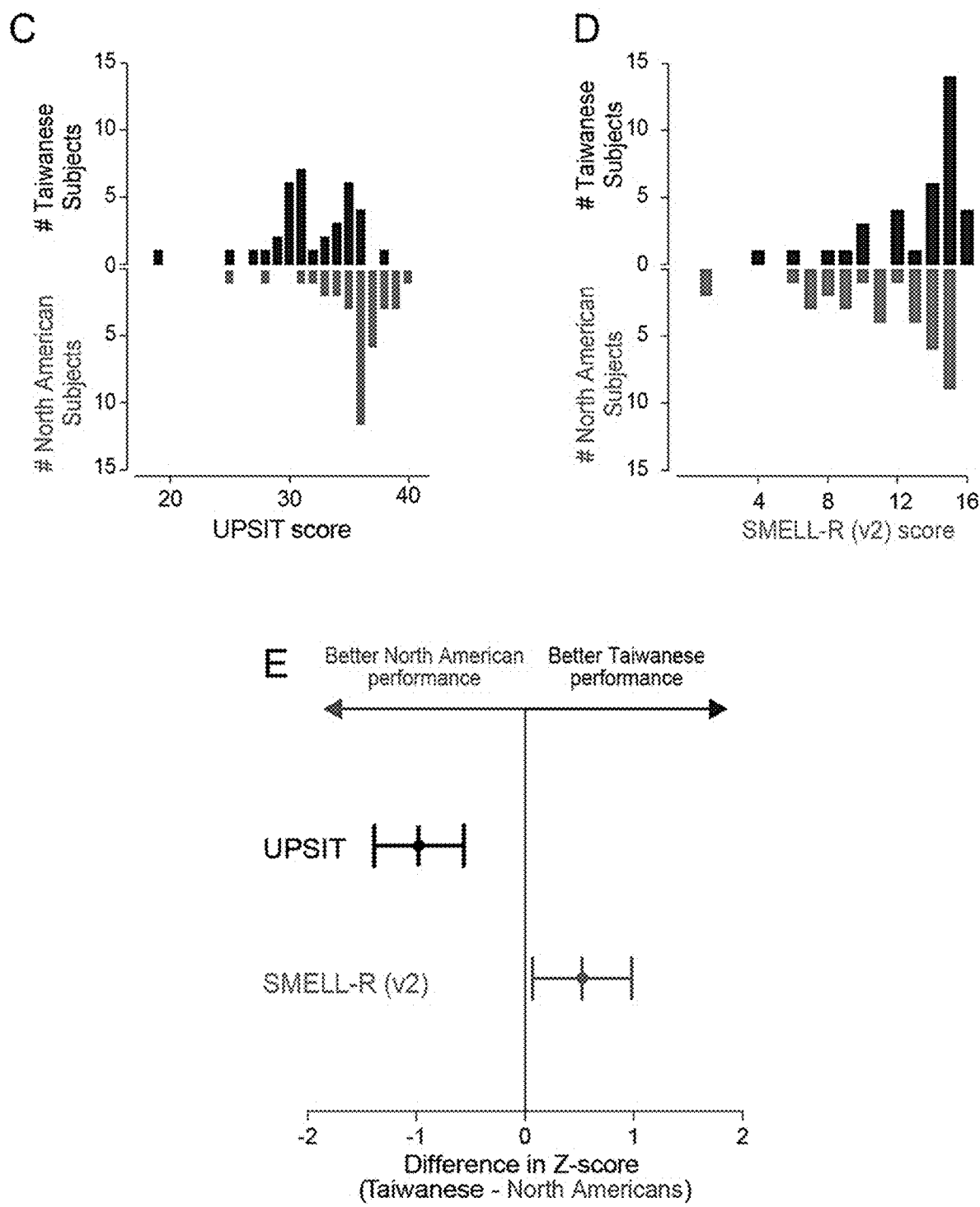

North Americans performed better on most of the items in the UPSIT, with the biggest differences found for "pine", "lime", "cherry", and "rose" (FIG. 5B). Even so, several items were frequently mistaken by North American subjects, including "paint thinner" when the correct answer was "cheddar cheese", "musk" instead of "lime", and "wintergreen" instead of "bubble gum". The Taiwanese subjects also struggled with the "cheddar cheese" item, also frequently mistaking it for "paint thinner", but in addition mistook "turpentine" for "soap", "motor oil" for "grass", and "clove" for "licorice". The overall UPSIT scores for Taiwanese subjects were significantly lower than those of the North American subjects (FIG. 5C) (p<0.0001, Mann Whitney test). In contrast, Taiwanese subjects scored higher on SMELL-R (v2) than the North American subjects (FIG. 5D) (p=0.0157, Mann Whitney test). The difference for the two populations was much smaller for SMELL-R (v2) than the UPSIT as determined by calculating the difference in Z-scores (FIG. 5E). While we do not know the underlying cause for the superior performance of Taiwanese subjects on SMELL-R (v2), the results show that our test avoids the bias seen for the UPSIT, in which test performance is systematically higher in the population for which the test was developed. We conclude that SMELL-R (v2) can be applied across different populations with different prior olfactory experiences, and without the need to adapt it to the local culture and language.

Materials and Methods
General, Subjects

All behavioral testing with human subjects took place between March 2015 and December 2016, and was approved and monitored by the Institutional Review Boards of The Rockefeller University in New York, NY (USA), except the Taiwanese arm of Experiment 3, which was approved by the Institutional Review Board of Taichung Veterans General Hospital in Taichung, Taiwan. North American subjects were recruited by The Rockefeller University Clinical Research Recruitment and Outreach Support Service (37). Taiwanese subjects were recruited by the nursing staff of the Department of Otorhinolaryngology at the Taichung Veterans General Hospital (Taiwan). All subjects gave their written informed consent to participate in these experiments, and were compensated for their time. All North American and Taiwanese subjects were able to understand and follow instructions in English or Mandarin, respectively. Subjects were aged 18 or over and agreed to refrain from using perfume or cologne, and ingesting anything except water one hour prior to the study visit. At the beginning of each visit, subjects washed their hands with odorless soap. For subjects reporting a normal sense of smell and taste, we excluded subjects who presented with current or past history of conditions that might be related to smell loss (acute or chronic rhinosinusitis, nasal tumor, upper respiratory tract infection or head trauma that altered the sense of smell for more than one month, history of brain or sinonasal surgery, asthma, stroke, neurodegenerative disease, radiation therapy or chemotherapy, active smoking, or consumption of medication affecting the sense of smell during the study). Participants with self-reported smell dysfunction were not subject to these exclusion criteria. All raw data in the paper, including details about the demographics of the subjects, odorants, and composition of the test stimuli are in Supporting Data Set 1.

General, Tests

To allow for self-administration and automatic data collection, we designed a custom computer application that was used for the vial threshold tests and also the SMELL-S and SMELL-R tests. The testing station comprised a computer, wireless mouse, barcode scanner, and trays containing numbered stimulus containers labeled with bar codes. Triangle tests were set up so that subjects were never tested with the same set of stimuli twice in a row, to avoid the situation where subjects remembered their answers from the previous trial. Subjects used a barcode scanner to register test data automatically. Subjects took between 20-35 minutes to complete each smell test, with the exception of the UPSIT which took 10-15 minutes. A standard inter-trial interval was imposed to avoid odor adaptation by requiring subjects to play a computer game for 20 seconds.

SMELL-S and SMELL-R were created with four different mixtures of 30 molecules drawn from a panel of 109 monomolecular, intensity-matched chemicals. These odorants were selected from stimuli utilized in previous psychophysical studies (21, 38). We used only molecules that minimally activated the trigeminal system, because such stimuli can be detected by anosmic subjects (39, 40). A characteristic of trigeminal activation by a molecule is a fresh, cold, burning, eucalyptus, pungent, or tickling sensation. We used a lateralization task in which an odorant is applied into only one nostril to assign a lateralization score to each molecule. It is possible to localize the stimulated nostril if it activates the trigeminal system. In contrast, it is much harder to localize an olfactory stimulus (41). Lateralization tasks were self-administered by one investigator. Two disposable squeeze bottles were placed in a device facilitating simultaneous squeezing and stimuli delivery in each nostril. Only one bottle was filled with an odor stimulus. The tip of each bottle was fitted with a foam piece that conformed to the investigator's nostril, and placed at the entrance of each nostril. The investigator squeezed both bottles simultaneously and attempted to localize which nostril had received the stimulus. After each task, the device was spun on a rotating platform to randomize the odor-stimulus side. The final score corresponded to the number of correct tasks. There were a total of 20 tasks (42). As a control experiment, we found that the lateralization score of the trigeminal stimulus eucalyptol (CID: 2758) at pure concentration was high (median, 20; interquartile range, 19.25-20; 4 trials). The lateralization score of the olfactory stimulus vanillin (CID: 1183) at pure concentration was low (median, 6.5; interquartile range, 5-12.5, 6 trials). The difference between the lateralization scores of eucalyptol and vanillin was statistically significant (p=0.0009, Mann-Whitney test). Each candidate for the mixtures was tested once. We included candidates with a score of 11 and below in the design of the mixtures (Supporting Data Set 1).

To intensity-match molecules to be used in mixtures, odorants were diluted and three investigators individually classified them as "too weak", "well matched", or "too strong". The concentration of "too weak" stimuli was increased and that of "too strong" stimuli decreased by a factor of 10. Weak components that could not be intensity-matched even at pure concentrations were excluded from the pool of odorants. We repeated this process until most of the components fell into the optimal intensity range. For 18 components investigators could not reach a consensus about intensity, but these were nevertheless used in the mixtures (CID: 1068, 7969, 31244, 9589, 17898, 104721, 3314, 14491, 62144, 7583, 7983, 60999, 251531, 7799, 61151, 9609, 8118, 89440). With these components, we created four mixtures of 30 components. The SMELL-S (v1) mixture was used as the ODD odor in SMELL-R (v1), and the SMELL-S (v2) mixtures was used as the CONTROL odor in SMELL R (v2). The mixtures for SMELL-R (v1) CONTROL odor and SMELL-R (v2) ODD odor were unique to these tests. Details of all mixtures are in Supporting Data Set 1.

Stimuli for the vial threshold tests and SMELL-S were presented to subjects with amber glass vials (height: 95 mm, diameter: 28 mm). Stimuli for SMELL-R were presented to subjects with amber glass jars (height: 51 mm, diameter: 55 mm). The complete list of stimuli used in this study is in Supporting Data Set 1.

Threshold Tests: Phenylethyl Alcohol and Butanol

Threshold tests were administered as a series of triangle tests. Subjects were presented with three vials: two contained 1 ml solvent (paraffin oil) and one contained either phenylethyl alcohol or butanol diluted in solvent in a total volume of 1 ml. Tests comprised 16 different concentrations generated by serial dilutions (1:2) of either odorant in paraffin oil, with the starting concentrations at 0.0313% for phenylethyl alcohol (vial) and 0.25% for butanol (vial). The subject was prompted to sniff each vial and select the one with the strongest perceived odor using an adaptive staircase procedure commonly used in smell testing (23). If they were unable to detect any difference among the three vials, they were prompted to choose one at random. The procedure started at the lowest concentration. If they identified an incorrect vial, the second next higher concentration was presented and so on, until they identified the correct vial. If the subjects identified the correct vial, they were retested at the same concentration. If they identified the correct vial in this retest, they were tested at the next lower concentration. If they identified an incorrect vial, they were tested at the next higher concentration. A reversal is when the direction in which the concentration is changed reverses. The procedure ended after the seventh reversal, or until the subject failed the level with the highest concentration twice in row, or succeeded with the lowest concentration level 5 times in row. The threshold was defined as the average of the concentrations at which the last two reversals occurred. If the highest concentration were not correctly identified twice, the score was 1. If the lowest was identified 5 times in a row, the score was 16.

SMELL-S Olfactory Sensitivity Test (v1 and v2)

For SMELL-S (v1) and SMELL-S (v2), we prepared 19 serial dilutions in paraffin oil (1:2) of two different mixtures of 30 monomolecular odorants and used the last 16 dilutions, such that the tests ranged from easiest (level 1, 1:8 dilution) to most difficult (level 16, 1:262,144 dilution). Subjects were asked to sniff 3 vials, one of which was filled with 1 ml of a mixture of 30 components, and the other two were filled with 1 ml of solvent (paraffin oil). Subjects were instructed to pick out the one vial with the strongest perceived odor. If they were unable to detect any difference among the three vials, they were prompted to choose one at random. The procedure started at the lowest concentration (level 16). We calculated the SMELL-S sensitivity score following the same adaptive staircase procedure described above. For each subject, we measured the olfactory sensitivity with two versions of the tests, SMELL-S (v1) and SMELL-S (v2), which differed only by the chemical composition of the mixtures.

SMELL-R Olfactory Resolution Tests (v1 and v2)

For SMELL-R (v1) and SMELL-R (v2), we prepared 16 pairs of mixtures of 30 monomolecular odorants that differ in how many components the two mixtures in the pair share from 0% (easiest; level 1) to 96.7% (most difficult; level 16). To create 16 levels of increasing overlapping components, we randomly progressively replaced components of a mixture of 30 molecules (we termed this the ODD odor), with components from another mixture of 30 components that did not change in composition across the levels (we termed this the CONTROL odor). Increasing the level of difficulty by one point correspond to an addition of 2 overlapping molecules between both mixtures, except from level 15 to 16, where we added only 1 shared molecule. Stimuli (8 ml) were introduced into jars containing absorbent cotton pads. Subjects were asked to sniff the contents of 3 jars, one of which was filled with 8 ml of a mixture of 30 components, and the other two were filled with 8 ml of a mixture of 30 components with different degree of overlap with the first jar. Subjects were instructed to pick out the odd jar. If they were unable to detect any difference among the three jars, they were prompted to choose one at random. Triangle tests started at a medium difficulty (level 8). If they identified the incorrect jar, the next easier level was presented. We calculated the SMELL-R resolution score following the same adaptive staircase procedure described above. For each subject, we measured the olfactory resolution with two versions of the tests, SMELL-R (v1) and SMELL-R (v2), which differed only in the chemical constituents of the two sets of mixtures.

Sniffin' Sticks Phenylethyl Alcohol Threshold Test

The Sniffin' Sticks (23) threshold phenylethyl alcohol threshold test is a commercial product that uses felt-tip pens filled with odorant instead of ink for odor presentation. [threshold module (2-phenyl ethanol) of the extended Burghart Sniffin' Sticks test, Burghart Messtechnik, item #LA-13-00015]. The test comprises pens containing 16 serial dilutions of phenylethyl alcohol (1:2) in solvent (propylene glycol) with a starting concentration of 4%. The test was administered as a triangle test. Three pens were presented to the subjects by the investigator in a randomized order. Two pens contained the solvent only, and the third pen contained the diluted odorant. Subjects were blindfolded with a disposable mask because the color code of the Sniffin' Sticks reveals which pen contains the odor, and were asked to identify the pen with the strongest perceived odor. The procedure started at the lowest or second lowest concentration of odorant (level 16 or 15, respectively). We calculated the threshold score following the same adaptive staircase procedure described above except that the threshold was defined as the average of the last four reversals occurred.

UPSIT

The University of Pennsylvania Smell Identification Test (UPSIT, marketed as the Smell Identification Test by Sensonics International) is a well-validated and self-administered smell identification test widely used in the USA (43). The test consists of 4 different 10-page booklets, with a total of 40 monomolecular stimuli. On each page, there is a different "scratch and sniff" strip which is embedded with a microencapsulated odorant. There are also four choice multiple-choice questions on each page. Subjects used the tip of a pencil to release the smell of the stimuli. Subjects sniffed the odorant and selected the one word among the four options (for example "paint thinner", "cherry", "coconut", or "cheddar cheese") that most closely matched their perception of the smell. Subjects entered their answers to the 40 multiple-choice questions manually into a booklet, and investigators transferred the data manually into a spreadsheet. UPSIT performance was scored as the number of correct answers out of 40. We used the same North American UPSIT (43) on subjects at Rockefeller University and Taichung Veterans General Hospital. The Taiwanese subjects were given a reference sheet on which the English multiple-choice questions in the UPSIT booklets were translated into Chinese by R.-S. J. (FIG. 5B) (18).

Experiment 1, Design

In this protocol (Rockefeller University IRB Protocol #JHS-0862), we studied the test-retest reliability of SMELL-S and SMELL-R. We invited volunteers with self-reported normal sense of smell and taste to the Rockefeller University Hospital for six visits (FIG. 2A). During these six visits, six olfactory tests were performed, each of them once during a test session (visit 1 to 3), and then again during a retest session (visit 4 to 6). There was a gap of at least 1 week between the last test visit (visit 3) and the first retest visit (visit 4), and a gap of at least 24 hours between each of the other visits. At each visit, two of the six tests were performed. Although the order of the tests was randomized, in any visit where SMELL-R tests were administered, they were always administered after the SMELL-S or the threshold tests. This experiment was done between March and June 2015.

Experiment 1, Subjects 75 subjects (43 female) participated in this experiment, with a mean age of 44 (range: 21-74). 34 subjects self-identified as White, 26 as Black, 6 as Asian, 2 as Mixed Race, and 7 as Other. 11 subjects self-identified as Hispanic. It took an average of 21 days (range: 14-38 days) for subjects to complete all 6 visits in this experiment.

Experiment 1, Statistical Analysis

The Intra-class Correlation Coefficient (ICC) was used to measure absolute agreement between test and retest measures for the whole cohort. A sample of n=75 subjects provided 95% confidence that the ICC in the population was larger than 0.67 based on a sample distribution that is centered on 0.8 (44). Bland-Altman plots were used as an auxiliary tool if significant differences in inter-individual variability were found between compared tests (24) (FIG. 2B). We used the non-parametric Conover squared ranks test to assess equality of variance across threshold tests. Statistical significance was reached when $p<0.05$ (FIG. 3A).

Experiment 2, Design

This experiment was carried out under Rockefeller University IRB protocol #JHS-0922, and was designed to evaluate the accuracy of our tests and whether SMELL-S can distinguish between subjects with specific-anosmia to phenylethyl alcohol but an otherwise normal sense of smell and subjects with smell dysfunction. During a single visit in December 2016, subjects performed four smell tests. The first two tests were either SMELL-S (v2) or Sniffin' Sticks phenylethyl alcohol threshold test. The order of these first two tests was randomized. It was followed by SMELL-R (v2) and finally the UPSIT, as a validated commercial reference test. The investigators enforced a break of at least 3 minutes between tests. During some of the breaks, participants filled out a questionnaire to provide demographic information and answer questions about their sense of taste and smell (Supporting Data Set 1). In 7 cases in the UPSIT tests in Experiment 2, subjects did not provide an answer to a given item, and this was scored as an incorrect answer. The missing data correspond to 3 subjects who missed one item each, and 2 subjects who missed 2 items each.

Experiment 2, Subjects

This experiment included 33 subjects (22 female), with a mean age of 48 (range: 21-76). 17 subjects self-identified as White, 8 as Black, 3 as Asian, 2 as Mixed Race, 1 as Other. Two subjects opted out of self-reporting race. Four subjects self-identified as Hispanic. We re-enrolled 23 subjects from Experiment 1 who self-reported a normal sense of smell and taste. These 23 were selected based on their threshold test results to have approximately even representation of subjects with low, medium, and high sensitivity to phenylethyl alcohol. In addition, we recruited 10 subjects with self-reported smell dysfunction. The self-reported etiologies are reported in Supporting Data Set 1.

Experiment 2, Statistical Analysis

We performed a power analysis and determined that a study with 32 subjects (8 with smell loss and 24 with a normal sense of smell) guarantees 80% power at 5% significance to detect an area under the ROC curve greater than 0.78. Since our actual study included 33 subjects, we carried out a post hoc power analysis using the parameters above to show that we can detect an area under the ROC curve greater than 0.79. We employed Youden's Index (27) to find the best cut-off score for SMELL-S and SMELL-R to maximize correct classification of the olfactory sensitivity and resolution of a subject, respectively (FIG. 4C,F). We used two-sided unpaired t-test with Welch's correction to test for differences between SMELL-S and SMELL-R score in normal and dysfunctional groups (FIG. 4A,C).

Experiment 3, Design

In this experiment, we investigated how SMELL-R performs on different populations by comparing Taiwanese (IRB TCVGH #CE16119B) and North American (Rockefeller University IRB Protocol #JHS-0901) subjects. The North American subjects were tested at The Rockefeller University Hospital, and the Taiwanese subjects were tested in the Department of Otolaryngology at Taichung Veterans General Hospital. The experimental design was the same in both institutions. Each subject came to the test site for a single visit, during which subjects performed the SMELL-R (v2) and UPSIT, separated by a 10 minute break, in randomized order (FIG. 5A).

Experiment 3, Subjects 36 subjects were recruited at both sites. All subjects were born and raised in their respective country, had never travelled to the opposite country, and had a self-reported normal sense of smell and taste. In the North American group, the mean age was 25 (range: 19-30), 23 of 36 subjects were female, and 8 self-identified as White, 14 as Black, 4 as Asian, 9 as Mixed Race, and 1 as American Indian or Alaska native. Six self-identified as Hispanic. In the Taiwanese group, the mean age was 26 (range: 19-30) and 26 of 36 subjects were female. Although we recruited subjects with a self-reported normal sense of smell, two of the North American subjects had UPSIT and SMELL-R (v2) scores below the cut-off for olfactory dysfunction (FIG. 5C,D).

Experiment 3, Statistical Analysis

We used unpaired t-test with Welch's correction to test for differences between smell test performance between North American and Taiwanese subjects (FIG. 5C,D). These tests were applied with and without the 2 North American subjects with UPSIT scores below the cut-off defined for a normal sense of smell.

Statistical Analysis

Normality of data was tested throughout using the Kolmogorov—Smirnov test, and the appropriate statistics were used according to the distribution of the data. SPSS (IBM) and Prism (Graphpad) was used for all statistical analysis.

"INCLUDED and EXCLUDED MOLECULES" (Supporting Data Set 1)

| Molecules INCLUDED (n = 109): intensity-matched and lateralization score ≤11 | |
|---|---|
| CID | Odor name |
| 261 | butyraldehyde |
| 326 | cuminaldehyde |
| 454 | octanal |
| 660 | dihydrocoumarin |
| 957 | octanol |
| 1001 | phenethylamine |
| 1060 | pyruvic acid |
| 1068 | methyl sulfide |
| 1136 | 4-methyl-5-thiazoleethanol |
| 2969 | decanoic acid |
| 3314 | eugenol |
| 6054 | 2-phenylethanol |
| 6826 | dimethyl anthranilate |
| 6943 | 2-isopropylphenol |
| 7144 | 2-methoxy-4-methylphenol |
| 7335 | carvyl acetate |
| 7361 | furfuryl alcohol |
| 7409 | α-methylbenzyl alcohol |
| 7410 | acetophenone |
| 7559 | methyl phenylacetate |
| 7583 | diphenyl ether |

| Molecules INCLUDED (n = 109): intensity-matched and lateralization score ≤11 | |
|---|---|
| CID | Odor name |
| 7632 | α,α-dimethylbenzenepropanol |
| 7654 | phenethyl acetate |
| 7720 | 2-ethyl-1-hexanol |
| 7731 | 4-methylanisole |
| 7749 | ethyl propionate |
| 7761 | diethyl malonate |
| 7762 | ethyl butyrate |
| 7770 | propyl butyrate |
| 7792 | 3,7-dimethyl-1-octanol |
| 7793 | (−)-citronellol |
| 7795 | isoamyl butyrate |
| 7797 | ethyl heptanoate |
| 7799 | ethyl octanoate |
| 7803 | propyl propionate |
| 7820 | dimethyl succinate |
| 7826 | methyl heptanoate |
| 7921 | gamma-valerolactone |
| 7969 | benzenethiol |
| 7983 | butyl butyrate |
| 8007 | butylamine |
| 8030 | thiophene |
| 8048 | ethyl decanoate |
| 8049 | diethyl sebacate |
| 8063 | valeraldehyde |
| 8082 | piperidine |
| 8093 | 2-octanone |
| 8094 | heptanoic acid |
| 8118 | propyl sulfide |
| 8129 | heptanol |
| 8174 | decanol |
| 8205 | lauryl acetate |
| 8375 | 2-hydroxyacetophenone |
| 8635 | methyl anthranilate |
| 8797 | p-tolyl acetate |
| 8815 | 4-allylanisole |
| 8857 | ethyl acetate |
| 8878 | allyl heptanoate |
| 8914 | nonanol |
| 9024 | α,α-dimethylphenethyl acetate |
| 9589 | 3-acetylpyridine |
| 9609 | diethyl sulfide |
| 9862 | 6-methyl-5-hepten-2-one |
| 10364 | carvacrol |
| 11124 | methyl propionate |
| 11529 | butyl propionate |
| 11902 | methyl 2-furoate |
| 12097 | 5-methylfurfural |
| 12327 | ethyl undecanoate |
| 12348 | pentyl acetate |
| 12741 | 2-decanone |
| 13187 | 2-nonanone |
| 13216 | decahydro-2-naphthol |
| 14257 | undecane |
| 14491 | 1,6-hexanedithiol |
| 14514 | 2-acetyl-5-methylfuran |
| 16255 | Isoamyl octanoate |
| 16324 | allyl butyrate |
| 16537 | terpinyl formate |
| 17898 | 2-methoxy-3-methylpyrazine |
| 22873 | hexyl hexanoate |
| 24020 | ethyl 2-methylbutyrate |
| 31225 | phenethyl propionate |
| 31244 | p-anisaldehyde |
| 31265 | ethyl hexanoate |
| 31266 | allyl hexanoate |
| 60999 | benzyl phenylacetate |
| 61005 | 2-phenoxyethyl isobutyrate |
| 61027 | butyl 10-undecenoate |
| 61151 | methyl 2-methoxybenzoate |
| 61177 | hexyl formate |
| 61192 | 4-methyl-5-thiazoleethanol acetate |
| 61204 | delta-undecalactone |
| 61293 | ethyl-3-hydroxyhexanoate |
| 61527 | 3-acetyl-2,5-dimethylfuran |
| 61809 | 2-ethoxythiazole |
| 62144 | 2-furanmethanethiol formate |
| 62374 | 4-oxoisophorone |
| 62378 | dihydrojasmone |
| 62900 | whiskey lactone |
| 89440 | 6-acetyl-1,1,2,4,4,7-hexamethyltetralin |
| 101010 | 2-methyl-4-propyl-1,3-oxathiane |
| 104721 | 2-acetyl-3,5(6)-dimethylpyrazine |
| 235414 | omega-pentadecalactone |
| 246728 | 3-octanone |
| 251531 | phenethyl 2-furoate |
| 519539 | 2-(1-methylpropyl)thiazole |
| 521238 | 3-octyl acetate |
| 637566 | geraniol |

| Molecules EXCLUDED (n = 73): lateralization score >11 | |
|---|---|
| CID | Odor name |
| 263 | butanol |
| 379 | octanoic acid |
| 6050 | tributyrin |
| 6448 | bornyl acetate |
| 6501 | ethyl 3-methyl-3-phenylglycidate |
| 6544 | isophorone |
| 6549 | linalool |
| 6753 | omega-6-hexadecenlactone |
| 6998 | salicylaldehyde |
| 7047 | quinoline |
| 7059 | 6-methyl quinoline |
| 7127 | 4-allyl-1,2-dimethoxy benzene |
| 7136 | eugenyl acetate |
| 7147 | 1-phenyl-1-propanol |
| 7150 | methyl benzoate |
| 7165 | ethyl benzoate |
| 7194 | phenethyl benzoate |
| 7302 | 4-hydroxybutanoic acid lactone |
| 7519 | anisole |
| 7601 | phenethyl phenyl acetate |
| 7695 | anisyl acetate |
| 7824 | methyl caproate |
| 7894 | isoamylamine |
| 8103 | hexanol |
| 8137 | methyl 2-nonynoate |
| 8159 | heptyl acetate |
| 8163 | 2-undecanone |
| 8294 | linalyl acetate |
| 8658 | o-anisaldehyde |
| 8908 | hexyl acetate |
| 8918 | nonyl acetate |
| 10722 | o-tolualdehyde |
| 10882 | ethyl valerate |
| 10890 | amyl butyrate |
| 10895 | isobutyl propionate |
| 11086 | 2-aminoacetophenone |
| 11617 | allyl sulfide |
| 12178 | 3-hexanol |
| 12180 | methyl butyrate |
| 12206 | methyl valerate |
| 12265 | 2,5-dimethylpyrrole |
| 12377 | dipropyl disulfide |
| 12506 | tetrahydrofurfuryl acetate |
| 12587 | 4-methylvaleric acid |
| 12810 | delta-decalactone |
| 12813 | gamma-decalactone |
| 15606 | methyl nonanoate |
| 17617 | allyl cyclohexanepropionate |
| 18467 | 2-methoxypyrazine |
| 18827 | 1-octen-3-ol |
| 22386 | 2-pentanol |
| 24197 | diethyl malate |

| Molecules EXCLUDED (n = 73): lateralization score >11 | |
|---|---|
| CID | Odor name |
| 24513 | decanal dimethyl acetal |
| 24834 | 4-ethoxybenzaldehyde |
| 27458 | 2,3-diethylpyrazine |
| 31209 | alpha-amylcinnamaldehyde |
| 31210 | butyl phenyl acetate |
| 31219 | benzyl propionate |
| 31234 | 3-phenyl-1-propanol |
| 31252 | 2,5-dimethyl pyrazine |
| 31404 | butylated hydroxytoluene |
| 36822 | 5,6,7,8-tetrahydroquinoxaline |
| 60998 | isobutyl phenyl acetate |
| 61408 | allyl 2-ethylbutyrate |
| 61641 | methyl 3-(methylthio)propionate |
| 62089 | (±)-4-methyloctanoic acid |
| 440967 | (−)-beta-pinene |
| 520108 | 2-acetylthiazole |
| 565690 | menthyl isovalerate |
| 637758 | ethyl cinnamate |
| 637796 | isosafrole |
| 643820 | nerol |
| 5281168 | 2-hexenal |

| Molecules EXCLUDED (n = 39): lateralization score ≤11 but intensity-matching failed | |
|---|---|
| CID | Odor name |
| 753 | glycerol |
| 1030 | propylene glycol |
| 1183 | vanillin |
| 6506 | tri ethyl citrate |
| 6989 | thymol |
| 7360 | tetrahydrofurfuryl alcohol |
| 7635 | 2-ethylhexyl acetate |
| 7657 | benzyl ether |
| 7937 | 2,6-dimethylpyridine |
| 7991 | valeric acid |
| 8038 | isobutyl acetate |
| 8091 | methyl caprylate |
| 8180 | undecanoic acid |
| 8184 | 1-undecanol |
| 8186 | undecanal |
| 8193 | lauryl alcohol |
| 8363 | benzyl salicylate |
| 9025 | 1,3-dimethoxybenzene |
| 10430 | isovaleric acid |
| 13204 | delta-hexalactone |
| 14286 | 2-acetyl pyridine |
| 15654 | 4-methyl-5-vinylthiazole |
| 15717 | allyl phenylacetate |
| 17525 | hexyl butyrate |
| 21363 | cyclohexaneacetic acid |
| 26331 | 2-ethyl pyrazine |
| 27457 | 2-ethyl-3-methylpyrazine |
| 32594 | 2-isobutyl-3-methoxypyrazine |
| 61138 | 4-pentenoic acid |
| 61523 | 5-phenyl-1-pentanol |
| 61670 | 5-methylquinoxaline |
| 62375 | benzaldehyde dimethyl acetal |
| 62444 | methyl thiobutyrate |
| 62572 | ethyl-3-hydroxybutyrate |
| 93375 | trivertal |
| 228769 | octyl isovalerate |
| 440917 | d-limonene |
| 520296 | delta-tetradecalactone |
| 595928 | benzaldehyde propylene glycol acetal |

SMELL-S and SMELL-R: olfactory tests not influenced by odor-specific insensitivity or prior olfactory experience

"SMELL-R MIXTURES"

| SMELL-R (v1) | | | |
|---|---|---|---|
| | CID | Odor name | Dilution |
| first mix | 14514 | 2-acetyl-5-methylfuran | 1/1000 |
| first mix | 12741 | 2-decanone | 1/10 |
| first mix | 7720 | 2-ethyl-1-hexanol | 1/1,000 |
| first mix | 13187 | 2-nonanone | 1/100 |
| first mix | 6054 | 2-phenylethanol | 1/100 |
| first mix | 89440 | 6-acetyl-1,1,2,4,4,7-hexamethyltetralin | 1/10 |
| first mix | 7410 | acetophenone | 1/1,000 |
| first mix | 16324 | allyl butyrate | 1/1000 |
| first mix | 261 | butyraldehyde | 1/1,000 |
| first mix | 10364 | carvacrol | 1/1000 |
| first mix | 7335 | carvyl acetate | 1/1000 |
| first mix | 2969 | decanoic acid | 1/10 |
| first mix | 660 | dihydrocoumarin | 1/100 |
| first mix | 62378 | dihydrojasmone | 1/10 |
| first mix | 6826 | dimethyl anthranilate | 1/100 |
| first mix | 7583 | diphenyl ether | 1/1,000 |
| first mix | 24020 | ethyl 2-methylbutyrate | 1/1000 |
| first mix | 12327 | ethyl undecanoate | 1/10 |
| first mix | 61293 | ethyl-3-hydroxyhexanoate | pure |
| first mix | 3314 | eugenol | 1/1,000 |
| first mix | 7921 | gamma-valerolactone | 1/100 |
| first mix | 8094 | heptanoic acid | 1/10 |
| first mix | 8129 | heptanol | 1/1000 |
| first mix | 7795 | isoamyl butyrate | 1/10 |
| first mix | 1068 | methyl sulfide | 1/1,000 |
| first mix | 8914 | nonanol | pure |
| first mix | 31225 | phenethyl propionate | 1/100 |
| first mix | 1001 | phenethyl amine | 1/1,000 |
| first mix | 8030 | thiophene | 1/1000 |
| first mix | 9024 | α,α-dimethylphenethyl acetate | 1/10 |
| second mix | 519539 | 2-(1-methylpropyl)thiazole | 1/10,000 |
| second mix | 8375 | 2-hydroxyacetophenone | 1/1,000 |
| second mix | 6943 | 2-isopropylphenol | 1/1,000 |
| second mix | 7144 | 2-methoxy-4-methylphenol | 1/100,000 |
| second mix | 101010 | 2-methyl-4-propyl-1,3-oxathiane | 1/100,000 |
| second mix | 8093 | 2-octanone | 1/1,000 |
| second mix | 521238 | 3-octyl acetate | 1/10 |
| second mix | 1136 | 4-methyl-5-thiazoleethanol | 1/1,000 |
| second mix | 7731 | 4-methylanisole | 1/1,000 |
| second mix | 12097 | 5-methylfurfural | 1/1,000 |
| second mix | 31266 | allyl hexanoate | 1/1,000 |
| second mix | 7969 | benzenethiol | 1/100,000 |
| second mix | 60999 | benzyl phenyl acetate | 1/100 |
| second mix | 7983 | butyl butyrate | 1/1,000 |
| second mix | 8007 | butylamine | 1/10,000 |
| second mix | 13216 | decahydro-2-naphthol | 1/1,000 |
| second mix | 8174 | decanol | 1/10 |
| second mix | 61204 | delta-undecalactone | pure |
| second mix | 61177 | hexyl formate | 1/1,000 |
| second mix | 22873 | hexyl hexanoate | 1/10 |
| second mix | 61151 | methyl 2-methoxybenzoate | 1/100 |
| second mix | 7826 | methyl heptanoate | 1/1,000 |
| second mix | 7559 | methyl phenylacetate | 1/1,000 |
| second mix | 11124 | methyl propionate | 1/1,000 |
| second mix | 454 | octanal | 1/1,000 |
| second mix | 957 | octanol | 1/10 |
| second mix | 251531 | phenethyl 2-furoate | 1/100 |
| second mix | 7770 | propyl butyrate | 1/1,000 |
| second mix | 1060 | pyruvic acid | 1/10,000 |
| second mix | 8063 | valeraldehyde | 1/10,000 |

| SMELL-R (v2) | | | |
|---|---|---|---|
| | CID | Odor name | Dilution |
| first mix | 7793 | (−)-citronellol | 1/10 |
| first mix | 104721 | 2-acetyl-3,5(6)-dimethylpyrazine | 1/1,000 |
| first mix | 61809 | 2-ethoxythiazole | 1/10,000 |
| first mix | 17898 | 2-methoxy-3-methylpyrazine | 1/100,000 |
| first mix | 61005 | 2-phenoxyethyl isobutyrate | pure |
| first mix | 9589 | 3-acetylpyridine | 1/1,000 |
| first mix | 246728 | 3-octanone | 1/1,000 |
| first mix | 1136 | 4-methyl-5-thiazoleethanol | 1/1,000 |
| first mix | 61192 | 4-methyl-5-thiazoleethanol acetate | 1/1,000 |
| first mix | 9862 | 6-methyl-5-hepten-2-one | 1/1,000 |
| first mix | 61027 | butyl 10-undecenoate | pure |
| first mix | 11529 | butyl propionate | 1/1,000 |
| first mix | 660 | dihydrocoumarin | 1/100 |
| first mix | 7820 | dimethyl succinate | 1/10 |
| first mix | 8857 | ethyl acetate | 1/1,000 |
| first mix | 7762 | ethyl butyrate | 1/1,000 |
| first mix | 31265 | ethyl hexanoate | 1/100 |
| first mix | 7799 | ethyl octanoate | pure |
| first mix | 7749 | ethyl propionate | 1/1,000 |
| first mix | 12327 | ethyl undecanoate | 1/10 |
| first mix | 16255 | Isoamyl octanoate | 1/10 |
| first mix | 11902 | methyl 2-furoate | 1/1,000 |
| first mix | 454 | octanal | 1/1,000 |
| first mix | 7654 | phenethyl acetate | 1/10 |
| first mix | 8082 | piperidine | 1/10,000 |
| first mix | 8118 | propyl sulfide | 1/100,000 |
| first mix | 8797 | p-tolyl acetate | 1/1,000 |
| first mix | 14257 | undecane | pure |
| first mix | 62900 | whiskey lactone | 1/1,000 |
| first mix | 7632 | α,α-dimethylbenzenepropanol | 1/10 |
| second mix | 14491 | 1,6-hexanedithiol | 1/100,000 |
| second mix | 14514 | 2-acetyl-5-methylfuran | 1000 |
| second mix | 62144 | 2-furanmethanethiol formate | 1/1,000,000 |
| second mix | 7792 | 3,7-dimethyl-1-octanol | 1/1,000 |
| second mix | 61527 | 3-acetyl-2,5-dimethylfuran | 1/10,000 |
| second mix | 8815 | 4-allylanisole | 1/1,000 |
| second mix | 62374 | 4-oxoisophorone | 1/100 |
| second mix | 16324 | allyl butyrate | 1/1,000 |
| second mix | 8878 | allyl heptanoate | 1/100 |
| second mix | 326 | cuminaldehyde | 1/1,000 |
| second mix | 7761 | diethyl malonate | 1/100 |
| second mix | 8049 | diethyl sebacate | pure |
| second mix | 9609 | diethyl sulfide | 1/100,000 |
| second mix | 24020 | ethyl 2-methylbutyrate | 1000 |
| second mix | 8048 | ethyl decanoate | 1/10 |
| second mix | 7797 | ethyl heptanoate | 1/100 |
| second mix | 7361 | furfuryl alcohol | 1/1,000 |
| second mix | 637566 | geraniol | 1/10 |
| second mix | 8205 | lauryl acetate | 1/10 |
| second mix | 61151 | methyl 2-methoxybenzoate | 1/100 |
| second mix | 8635 | methyl anthranilate | 1/100 |
| second mix | 7826 | methyl heptanoate | 1/1,000 |
| second mix | 235414 | omega-pentadecalactone | 1/10 |
| second mix | 31244 | p-anisaldehyde | 1/1,000 |
| second mix | 12348 | pentyl acetate | 1/1,000 |
| second mix | 1001 | phenethylamine | 1/1,000 |
| second mix | 7770 | propyl butyrate | 1/1,000 |
| second mix | 7803 | propyl propionate | 1/1,000 |
| second mix | 16537 | terpinyl formate | 1/1,000 |
| second mix | 7409 | α-methylbenzyl alcohol | 1/100 |

SMELL-S and SMELL-R: olfactory tests not influenced by odor-specific insensitivity or prior olfactory experience "SMELL-S MIXTURES"

| SMELL-S (v1) | | |
|---|---|---|
| CID | Molecule | Dilution |
| 14514 | 2-acetyl-5-methylfuran | 1/1000 |
| 12741 | 2-decanone | 1/10 |
| 7720 | 2-ethyl-1-hexanol | 1/1,000 |
| 13187 | 2-nonanone | 1/100 |
| 6054 | 2-phenylethanol | 1/100 |
| 89440 | 6-acetyl-1,1,2,4,4,7-hexamethyltetralin | 1/10 |
| 7410 | acetophenone | 1/1,000 |
| 16324 | allyl butyrate | 1/1000 |
| 261 | butyraldehyde | 1/1,000 |
| 10364 | carvacrol | 1/1000 |
| 7335 | carvyl acetate | 1/1000 |
| 2969 | decanoic acid | 1/10 |
| 660 | dihydrocoumarin | 1/100 |
| 62378 | dihydrojasmone | 1/10 |
| 6826 | dimethyl anthranilate | 1/100 |
| 7583 | diphenyl ether | 1/1,000 |
| 24020 | ethyl 2-methylbutyrate | 1/1000 |
| 12327 | ethyl undecanoate | 1/10 |
| 61293 | ethyl-3-hydroxyhexanoate | pure |
| 3314 | eugenol | 1/1,000 |
| 7921 | gamma-valerolactone | 1/100 |
| 8094 | heptanoic acid | 1/10 |
| 8129 | heptanol | 1/1000 |
| 7795 | isoamyl butyrate | 1/10 |
| 1068 | methyl sulfide | 1/1,000 |
| 8914 | nonanol | pure |
| 31225 | phenethyl propionate | 1/100 |
| 1001 | phenethyl amine | 1/1,000 |
| 8030 | thiophene | 1/1000 |
| 9024 | α,α-dimethylphenethyl acetate | 1/10 |

| SMELL-S (v2) | | |
|---|---|---|
| CID | Molecule | Dilution |
| 14491 | 1,6-hexanedithiol | 1/100,000 |
| 14514 | 2-acetyl-5-methylfuran | 1/1000 |
| 62144 | 2-furanmethanethiol formate | 1/1,000,000 |
| 7792 | 3,7-dimethyl-1-octanol | 1/1,000 |
| 61527 | 3-acetyl-2,5-dimethylfuran | 1/10,000 |
| 8815 | 4-allylanisole | 1/1,000 |
| 62374 | 4-oxoisophorone | 1/100 |
| 16324 | allyl butyrate | 1/1,000 |
| 8878 | allyl heptanoate | 1/100 |
| 326 | cuminaldehyde | 1/1,000 |
| 7761 | diethyl malonate | 1/100 |
| 8049 | diethyl sebacate | pure |
| 9609 | diethyl sulfide | 1/100,000 |
| 24020 | ethyl 2-methylbutyrate | 1/1000 |
| 8048 | ethyl decanoate | 1/10 |
| 7797 | ethyl heptanoate | 1/100 |
| 7361 | furfuryl alcohol | 1/1,000 |
| 637566 | geraniol | 1/10 |
| 8205 | lauryl acetate | 1/10 |
| 61151 | methyl 2-methoxybenzoate | 1/100 |
| 8635 | methyl anthranilate | 1/100 |
| 7826 | methyl heptanoate | 1/1,000 |
| 235414 | omega-pentadecalactone | 1/10 |
| 31244 | p-anisaldehyde | 1/1,000 |
| 12348 | pentyl acetate | 1/1,000 |
| 1001 | phenethyl amine | 1/1,000 |
| 7770 | propyl butyrate | 1/1,000 |
| 7803 | propyl propionate | 1/1,000 |
| 16537 | terpinyl formate | 1/1,000 |
| 7409 | α-methylbenzyl alcohol | 1/100 |

SMELL-S and SMELL-R: olfactory tests not influenced by odor-specific insensitivity or prior olfactory experience

"SMELL-S DILUTION RATIO"

| SMELL-S (v1) | |
|---|---|
| | Dilution ratio |
| not used | 1:1* |
| not used | 1:2 |
| not used | 1:4 |
| Level 1 | 1:8 |
| Level 2 | 1:16 |
| Level 3 | 1:32 |
| Level 4 | 1:64 |
| Level 5 | 1:128 |
| Level 6 | 1:256 |
| Level 7 | 1:512 |
| Level 8 | 1:1024 |
| Level 9 | 1:2048 |
| Level 10 | 1:4096 |
| Level 11 | 1:8192 |
| Level 12 | 1:16384 |
| Level 13 | 1:32768 |
| Level 14 | 1:65536 |
| Level 15 | 1:131072 |
| Level 16 | 1:262144 |

*Dilution ratio 1:1 corresponds to a mixture of 30 components of equal volume from the "SMELL-S mixtures"

| SMELL-S (v2) | |
|---|---|
| | Dilution Ratio |
| not used | 1:1* |
| not used | 1:2 |
| not used | 1:4 |
| Level 1 | 1:8 |
| Level 2 | 1:16 |
| Level 3 | 1:32 |
| Level 4 | 1:64 |
| Level 5 | 1:128 |
| Level 6 | 1:256 |
| Level 7 | 1:512 |
| Level 8 | 1:1024 |
| Level 9 | 1:2048 |
| Level 10 | 1:4096 |
| Level 11 | 1:8192 |
| Level 12 | 1:16384 |
| Level 13 | 1:32768 |
| Level 14 | 1:65536 |
| Level 15 | 1:131072 |
| Level 16 | 1:262144 |

*Dilution ratio 1:1 corresponds to a mixture of 30 components of equal volume from the "SMELL-S mixtures"

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing ODD odor. All mixtures have equal volumes of each component.

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing the ODD odor. All mixtures have equal volumes of each component.

| CID | Odor name | Dilution | CAS # |
|---|---|---|---|
| | SMELL-R (v1) - level 1 - ODD odor | | |
| 7720 | 2-ethyl-1-hexanol | 1/1,000 | 104-76-7 |
| 10364 | carvacrol | 1/1000 | 499-75-2 |
| 3314 | eugenol | 1/1,000 | 97-53-0 |
| 6054 | 2-phenylethanol | 1/100 | 60-12-8 |
| 14514 | 2-acetyl-5-methylfuran | 1/1000 | 1193-79-9 |
| 261 | butyraldehyde | 1/1,000 | 123-72-8 |
| 12327 | ethyl undecanoate | 1/10 | 627-90-7 |
| 62378 | dihydrojasmone | 1/10 | 1128-08-1 |
| 7795 | isoamyl butyrate | 1/10 | 106-27-4 |
| 24020 | ethyl 2-methylbutyrate | 1/1000 | 7452-79-1 |
| 61293 | ethyl-3-hydroxyhexanoate | pure | 2305-25-1 |
| 6826 | dimethyl anthranilate | 1/100 | 85-91-6 |
| 13187 | 2-nonanone | 1/100 | 821-55-6 |
| 2969 | decanoic acid | 1/10 | 334-48-5 |
| 7583 | diphenyl ether | 1/1,000 | 101-84-8 |
| 8129 | heptanol | 1/1000 | 111-70-6 |
| 31225 | phenethyl propionate | 1/100 | 122-70-3 |
| 7921 | gamma-valerolactone | 1/100 | 108-29-2 |
| 8094 | heptanoic acid | 1/10 | 111-14-8 |
| 1001 | phenethylamine | 1/1,000 | 64-04-0 |
| 8030 | thiophene | 1/1000 | 110-02-1 |
| 8914 | nonanol | pure | 143-08-8 |
| 12741 | 2-decanone | 1/10 | 693-54-9 |
| 1068 | methyl sulfide | 1/1,000 | 75-18-3 |
| 7410 | acetophenone | 1/1,000 | 98-86-2 |
| 16324 | allyl butyrate | 1/1000 | 2051-78-7 |
| 7335 | carvyl acetate | 1/1000 | 97-42-7 |
| 89440 | 6-acetyl-1,1,2,4,4,7-hexamethyltetralin | 1/10 | 21145-77-7 |
| 9024 | α,α-dimethylphenethyl acetate | 1/10 | 151-05-3 |
| 660 | dihydrocoumarin | 1/100 | 119-84-6 |
| 7720 | 2-ethyl-1-hexanol | 1/1000 | 104-76-7 |
| 10364 | carvacrol | 1/1000 | 499-75-2 |
| 3314 | eugenol | 1/1000 | 97-53-0 |
| 6054 | 2-phenylethanol | 1/100 | 60-12-8 |
| 14514 | 2-acetyl-5-methylfuran | 1/1000 | 1193-79-9 |
| 261 | butyraldehyde | 1/1,000 | 123-72-8 |
| 12327 | ethyl undecanoate | 1/10 | 627-90-7 |
| 62378 | dihydrojasmone | 1/10 | 1128-08-1 |
| 7795 | isoamyl butyrate | 1/10 | 106-27-4 |
| 24020 | ethyl 2-methylbutyrate | 1/1000 | 7452-79-1 |
| 61293 | ethyl-3-hydroxyhexanoate | pure | 2305-25-1 |
| 6826 | dimethyl anthranilate | 1/100 | 85-91-6 |
| 13187 | 2-nonanone | 1/100 | 821-55-6 |
| 2969 | decanoic acid | 1/10 | 334-48-5 |
| 7583 | diphenyl ether | 1/1,000 | 101-84-8 |
| 8129 | heptanol | 1/1000 | 111-70-6 |
| 31225 | phenethyl propionate | 1/100 | 122-70-3 |
| 7921 | gamma-valerolcatone | 1/100 | 108-29-2 |
| 8094 | heptanoic acid | 1/10 | 111-14-8 |
| 1001 | phenethylamine | 1/1,000 | 64-04-0 |
| 8030 | thiophene | 1/1000 | 110-02-1 |
| 8914 | nonanol | pure | 143-08-8 |
| 12741 | 2-decanone | 1/10 | 693-54-9 |
| 1088 | methyl sulfide | 1/1,000 | 75-18-3 |
| 7410 | acetophenone | 1/1,000 | 98-86-2 |
| 16324 | allyl butyrate | 1/1000 | 2051-78-7 |
| 7335 | carvyl acetate | 1/1000 | 97-42-7 |
| 89440 | 6-acetyl-1,1,2,4,4,7-hexamethyltetralin | 1/10 | 21145-77-7 |
| 9024 | α,α-dimethlyphenethyl acetate | 1/10 | 151-05-3 |
| 660 | dihydrocoumarin | | 119-84-6 |
| | SMELL-R (v1) - level 1 - CONTROL odor | | |
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing the ODD odor. All mixtures have equal volumes of each component.

| CID | Odor name | Dilution | CAS # |
|---|---|---|---|
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/1,000 | 18277-27-5 |
| 61204 | delta-undecalactone | pure | 710-04-3 |
| 957 | octanol | 1/10 | 111-87-5 |
| 61177 | hexyl formate | 1/1,000 | 620-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/1,000 | 118-62-3 |
| 1136 | 4-methyl-5-thiazoleethanol | 1/1,000 | 137-00-8 |
| 8007 | butylamine | 1/1,000 | 109-73-9 |
| 251531 | phenethyl 2-furoate | 1/100 | 7149-32-8 |
| 1060 | pyruvic acid | 1/1,000 | 127-17-3 |
| 60999 | benzyl phenylacetate | 1/100 | 102-16-9 |
| 11124 | methyl propionate | 1/1,000 | 554-12-1 |
| 454 | octanal | 1/1,000 | 124-13-0 |
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/1,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/1,000 | 110-62-3 |
| 1136 | 4-methyl-5-thiazoleethanol | 1/1,000 | 137-00-8 |
| 8007 | butylamine | 1/1,000 | 109-73-9 |
| 251531 | phenethyl 2-furoate | 1/100 | 7149-32-8 |
| 1060 | pyruvic acid | 1/1,000 | 127-17-3 |
| 60999 | benzyl phenylacetate | 1/100 | 102-16-9 |
| 11124 | methyl propionate | 1/1,000 | 554-12-1 |
| 454 | octanal | 1/1,000 | 124-13-0 |

SMELL-R (v1) - level 2 - ODD odor

| CID | Odor name | Dilution | CAS # |
|---|---|---|---|
| 7969 | benzenethiol | 1/100,000 | 108-98-5 |
| 7731 | 4-methylanisole | 1/1,000 | 104-93-8 |
| 3314 | eugenol | 1/1,000 | 97-53-0 |
| 6054 | 2-phenylethanol | 1/100 | 60-12-8 |
| 14514 | 2-acetyl-5-methylfuran | 1/1,000 | 1193-79-9 |
| 261 | butyraldehyde | 1/1,000 | 123-72-8 |
| 12327 | ethyl undecanoate | 1/10 | 627-90-7 |
| 62378 | dihydrojasmone | 1/10 | 1128-08-1 |
| 7795 | isoamyl butyrate | 1/10 | 106-27-4 |
| 24020 | ethyl 2-methylbutyrate | 1/1,000 | 7452-79-1 |
| 61293 | ethyl-3-hydroxyhexanoate | pure | 2305-25-1 |
| 6826 | dimethyl anthranilate | 1/100 | 85-91-6 |
| 13187 | 2-nonanone | 1/100 | 821-55-6 |
| 2969 | decanoic acid | 1/10 | 334-48-5 |
| 7583 | diphenyl ether | 1/1,000 | 101-84-8 |
| 8129 | heptanol | 1/1,000 | 111-70-6 |
| 31225 | phenethyl propionate | 1/100 | 122-70-3 |
| 7921 | gamma-valerolacetone | 1/100 | 108-29-2 |
| 8094 | heptanoic acid | 1/10 | 111-14-8 |
| 1001 | phenethylamine | 1/1,000 | 64-04-0 |
| 8030 | thiophene | 1/1,000 | 110-02-1 |
| 8914 | nonanol | pure | 143-08-8 |
| 12741 | 2-decanone | 1/10 | 693-54-9 |
| 1068 | methyl sulfide | 1/1,000 | 75-18-3 |
| 7410 | acetophenone | 1/1,000 | 98-86-2 |
| 16324 | allyl butyrate | 1/1,000 | 2051-78-7 |
| 7335 | carvyl acetate | 1/1,000 | 97-42-7 |
| 89440 | 6-acetyl-1,1,2,4,4,7-hexamethyltetralin | 1/10 | 21145-77-7 |
| 9024 | α,α-dimethylphenethyl acetate | 1/10 | 151-05-3 |
| 660 | dihydrocoumarin | 1/100 | 119-84-6 |

SMELL-R (v1) - level 2 - CONTROL odor

| CID | Odor name | Dilution | CAS # |
|---|---|---|---|
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/1,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/1,000 | 110-62-3 |
| 1136 | 4-methyl-5-thiazoleethanol | 1/1,000 | 137-00-8 |
| 8007 | butylamine | 1/1,000 | 109-73-9 |
| 251531 | phenethyl 2-furoate | 1/100 | 7149-32-8 |
| 1060 | pyruvic acid | 1/1,000 | 127-17-3 |
| 60999 | benzyl phenylacetate | 1/100 | 102-16-9 |
| 11124 | methyl propionate | 1/1,000 | 554-12-1 |
| 454 | octanal | 1/1,000 | 124-13-0 |

SMELL-R (v1) - level 3 - ODD odor

| CID | Odor name | Dilution | CAS # |
|---|---|---|---|
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 14514 | 2-acetyl-5-methylfuran | 1/1,000 | 1193-79-9 |
| 261 | butyraldehyde | 1/1,000 | 123-72-8 |
| 12327 | ethyl undecanoate | 1/10 | 627-90-7 |
| 62378 | dihydrojasmone | 1/10 | 1128-08-1 |
| 7795 | isoamyl butyrate | 1/10 | 106-27-4 |
| 24020 | ethyl 2-methylbutyrate | 1/1,000 | 7452-79-1 |
| 61293 | ethyl-3-hydroxyhexanoate | pure | 2305-25-1 |
| 6826 | dimethyl anthranilate | 1/100 | 85-91-6 |
| 13187 | 2-nonanone | 1/100 | 821-55-6 |
| 2969 | decanoic acid | 1/10 | 334-48-5 |
| 7583 | diphenyl ether | 1/1,000 | 101-84-8 |
| 8129 | heptanol | 1/1,000 | 111-70-6 |
| 31225 | phenethyl propionate | 1/100 | 122-70-3 |
| 7921 | gamma-valerolactone | 1/100 | 108-29-2 |
| 8094 | heptanoic acid | 1/10 | 111-14-8 |

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing the ODD odor. All mixtures have equal volumes of each component.

| CID | Odor name | Dilution | CAS # |
|---|---|---|---|
| 1001 | phenethylamine | 1/1,000 | 64-04-0 |
| 8030 | thiophene | 1/1,000 | 110-02-1 |
| 8914 | nonanol | pure | 143-08-8 |
| 12741 | 2-decanone | 1/10 | 693-54-9 |
| 1068 | methyl sulfide | 1/1,000 | 75-18-3 |
| 7410 | acetophenone | 1/1,000 | 98-86-2 |
| 16324 | allyl butyrate | 1/1,000 | 2051-78-7 |
| 7335 | carvyl acetate | 1/1,000 | 97-42-7 |
| 89440 | 6-acetyl-1,1,2,4,4,7-hexamethyltetralin | 1/10 | 21145-77-7 |
| 9024 | α,α-dimethylphenethyl acetate | 1/10 | 151-05-3 |
| 660 | dihydrocoumarin | 1/100 | 119-84-6 |

SMELL-R (v1) - level 3 - CONTROL odor

| CID | Odor name | Dilution | CAS # |
|---|---|---|---|
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/1,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/1,000 | 110-62-3 |
| 1136 | 4-methyl-5-thiazoleethanol | 1/1,000 | 137-00-8 |
| 8007 | butylamine | 1/1,000 | 109-73-9 |
| 251531 | phenethyl 2-furoate | 1/100 | 7149-32-8 |
| 1060 | pyruvic acid | 1/1,000 | 127-17-3 |
| 60999 | benzyl phenylacetate | 1/100 | 102-16-9 |
| 11124 | methyl propionate | 1/1,000 | 554-12-1 |
| 454 | octanal | 1/1,000 | 124-13-0 |

SMELL-R (v1) - level 4 - ODD odor

| CID | Odor name | Dilution | CAS # |
|---|---|---|---|
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-acetyl-5-methylfuran | 1/1,000 | 111-13-7 |
| 7826 | butyraldehyde | 1/1,000 | 106-73-0 |
| 12327 | ethyl undecanoate | 1/10 | 627-90-7 |
| 62378 | dihydrojasmone | 1/10 | 1128-08-1 |
| 7795 | isoamyl butyrate | 1/10 | 106-27-4 |
| 24020 | ethyl 2-methylbutyrate | 1/1,000 | 7452-79-1 |
| 61293 | ethyl-3-hydroxyhexanoate | pure | 2305-25-1 |
| 6826 | dimethyl anthranilate | 1/100 | 85-91-6 |
| 13187 | 2-nonanone | 1/100 | 821-55-6 |
| 2969 | decanoic acid | 1/10 | 334-48-5 |
| 7583 | diphenyl ether | 1/1,000 | 101-84-8 |
| 8129 | heptanol | 1/1,000 | 111-70-6 |
| 31225 | phenethyl propionate | 1/100 | 122-70-3 |
| 7921 | gamma-valerolactone | 1/100 | 108-29-2 |
| 8094 | heptanoic acid | 1/10 | 111-14-8 |
| 1001 | phenethylamine | 1/1,000 | 64-04-0 |
| 8030 | thiophene | 1/1,000 | 110-02-1 |
| 8914 | nonanol | pure | 143-08-8 |
| 12741 | 2-decanone | 1/10 | 693-54-9 |
| 1068 | methyl sulfide | 1/1,000 | 75-18-3 |
| 7410 | acetophenone | 1/1,000 | 98-86-2 |
| 16324 | allyl butyrate | 1/1,000 | 2051-78-7 |
| 7335 | carvyl acetate | 1/1,000 | 97-42-7 |
| 89440 | 6-acetyl-1,1,2,4,4,7-hexamethyltetralin | 1/10 | 21145-77-7 |
| 9024 | α,α-dimethylphenethyl acetate | 1/10 | 151-05-3 |
| 660 | dihydrocoumarin | 1/100 | 119-84-6 |

SMELL-R (v1) - level 4 - CONTROL odor

| CID | Odor name | Dilution | CAS # |
|---|---|---|---|
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/100,000 | 110-62-3 |
| 1136 | 4-methyl-5-thiazoleethanol | 1/1,000 | 137-00-8 |
| 8007 | butylamine | 1/100,000 | 109-73-9 |
| 251531 | phenethyl 2-furoate | 1/100 | 7149-32-8 |
| 1060 | pyruvic acid | 1/100,000 | 127-17-3 |
| 60999 | benzyl phenylacetate | 1/100 | 102-16-9 |
| 11124 | methyl propionate | 1/1,000 | 554-12-1 |
| 454 | octanal | 1/100,000 | 124-13-0 |

SMELL-R (v1) - level 5 - ODD odor

| CID | Odor name | Dilution | CAS # |
|---|---|---|---|
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-acetyl-5-methylfuran | 1/1,000 | 111-13-7 |
| 7826 | butyraldehyde | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 7795 | isoamyl butyrate | 1/10 | 106-27-4 |
| 24020 | ethyl 2-methylbutyrate | 1/1,000 | 7452-79-1 |
| 61293 | ethyl-3-hydroxyhexanoate | pure | 2305-25-1 |
| 6826 | dimethyl anthranilate | 1/100 | 85-91-6 |
| 13187 | 2-nonanone | 1/100 | 821-55-6 |
| 2969 | decanoic acid | 1/10 | 334-48-5 |
| 7583 | diphenyl ether | 1/1,000 | 101-84-8 |
| 8129 | heptanol | 1/1,000 | 111-70-6 |
| 31225 | phenethyl propionate | 1/100 | 122-70-3 |
| 7921 | gamma-valerolactone | 1/100 | 108-29-2 |
| 8094 | heptanoic acid | 1/10 | 111-14-8 |
| 1001 | phenethylamine | 1/1,000 | 64-04-0 |
| 8030 | thiophene | 1/1,000 | 110-02-1 |
| 8914 | nonanol | pure | 143-08-8 |
| 12741 | 2-decanone | 1/10 | 693-54-9 |
| 1068 | methyl sulfide | 1/1,000 | 75-18-3 |
| 7410 | acetophenone | 1/1,000 | 98-86-2 |

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing the ODD odor. All mixtures have equal volumes of each component.

| CID | Odor name | Dilution | CAS # |
|---|---|---|---|
| 16324 | allyl butyrate | 1/1,000 | 2051-78-7 |
| 7335 | carvyl acetate | 1/1,000 | 97-42-7 |
| 89440 | 6-acetyl-1,1,2,4,4,7-hexamethyltetralin | 1/10 | 21145-77-7 |
| 9024 | α,α-dimethylphenethyl acetate | 1/10 | 151-05-3 |
| 660 | dihydrocoumarin | 1/100 | 119-84-6 |
| SMELL-R (v1) - level 5 - CONTROL odor | | | |
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/100,000 | 110-62-3 |
| 1136 | 4-methyl-5-thiazoleethanol | 1/1,000 | 137-00-8 |
| 8007 | butylamine | 1/100,000 | 109-73-9 |
| 251531 | phenethyl 2-furoate | 1/100 | 7149-32-8 |
| 1060 | pyruvic acid | 1/100,000 | 127-17-3 |
| 60999 | benzyl phenylacetate | 1/100 | 102-16-9 |
| 11124 | methyl propionate | 1/1,000 | 554-12-1 |
| 454 | octanal | 1/1,000 | 124-13-0 |
| SMELL-R (v1) - level 6 - ODD odor | | | |
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61293 | ethyl-3-hydroxyhexanoate | pure | 2305-25-1 |
| 6826 | dimethyl anthranilate | 1/100 | 85-91-6 |
| 13187 | 2-nonanone | 1/100 | 821-55-6 |
| 2969 | decanoic acid | 1/10 | 334-48-5 |
| 7583 | diphenyl ether | 1/1,000 | 101-84-8 |
| 8129 | heptanol | 1/1,000 | 111-70-6 |
| 31225 | phenethyl propionate | 1/100 | 122-70-3 |
| 7921 | gamma-valerolacetone | 1/100 | 108-29-2 |
| 8094 | heptanoic acid | 1/10 | 111-14-8 |
| 1001 | phenethylamine | 1/1,000 | 64-04-0 |
| 8030 | thiophene | 1/1,000 | 110-02-1 |
| 8914 | nonanol | pure | 143-08-6 |
| 12741 | 2-decanone | 1/10 | 693-54-9 |
| 1068 | methyl sulfide | 1/1,000 | 75-18-3 |
| 7410 | acetophenone | 1/1,000 | 98-86-2 |
| 16324 | allyl butyrate | 1/1,000 | 2051-78-7 |
| 7335 | carvyl acetate | 1/1,000 | 97-42-7 |
| 89440 | 6-acetyl-1,1,2,4,4,7-hexamethyltetralin | 1/10 | 21145-77-7 |
| 9024 | α,α-dimethylphenethyl acetate | 1/10 | 151-05-3 |
| 660 | dihydrocoumarin | 1/100 | 119-84-6 |
| SMELL-R (v1) - level 6 - CONTROL odor | | | |
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/100,000 | 110-62-3 |
| 1136 | 4-methyl-5-thiazoleethanol | 1/1,000 | 137-00-8 |
| 8007 | butylamine | 1/100,000 | 109-73-9 |
| 251531 | phenethyl 2-furoate | 1/100 | 7149-32-8 |
| 1060 | pyruvic acid | 1/100,000 | 127-17-3 |
| 60999 | benzyl phenylacetate | 1/100 | 102-16-9 |
| 11124 | methyl propionate | 1/1,000 | 554-12-1 |
| 454 | octanal | 1/1,000 | 124-13-0 |
| SMELL-R (v1) - level 7 - ODD odor | | | |
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 13187 | 2-nonanone | 1/100 | 821-55-6 |
| 2969 | decanoic acid | 1/10 | 334-48-5 |
| 7583 | diphenyl ether | 1/1,000 | 101-84-8 |
| 8129 | heptanol | 1/1,000 | 111-70-6 |
| 31225 | phenethyl propionate | 1/100 | 122-70-3 |
| 7921 | gamma-valerolacetone | 1/100 | 108-29-2 |
| 8094 | heptanoic acid | 1/10 | 111-14-8 |
| 1001 | phenethylamine | 1/1,000 | 64-04-0 |
| 8030 | thiophene | 1/1,000 | 110-02-1 |
| 8914 | nonanol | pure | 143-08-6 |
| 12741 | 2-deoanone | 1/10 | 693-54-9 |
| 1068 | methyl sulfide | 1/1,000 | 75-18-3 |
| 7410 | acetophenone | 1/1,000 | 98-86-2 |
| 16324 | allyl butyrate | 1/1,000 | 2051-78-7 |
| 7335 | carvyl acetate | 1/1,000 | 97-42-7 |
| 89440 | 6-acetyl-1,1,2,4,4,7-hexamethyltetralin | 1/10 | 21145-77-7 |
| 9024 | α,α-dimethylphenethyl acetate | 1/10 | 151-05-3 |
| 660 | dihydrocoumarin | 1/100 | 119-84-6 |
| SMELL-R (v1) - level 7 - CONTROL odor | | | |
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing the ODD odor. All mixtures have equal volumes of each component.

| CID | Odor name | Dilution | CAS # |
|---|---|---|---|
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/1,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/100,000 | 110-62-3 |
| 1136 | 4-methyl-5-thiazoleethanol | 1/1,000 | 137-00-8 |
| 8007 | butylamine | 1/100,000 | 109-73-9 |
| 251531 | phenethyl 2-furoate | 1/100 | 7149-32-8 |
| 1060 | pyruvic acid | 1/100,000 | 127-17-3 |
| 60999 | benzyl phenylacetate | 1/100 | 102-16-9 |
| 11124 | methyl propionate | 1/1,000 | 554-12-1 |
| 454 | octanal | 1/1,000 | 124-13-0 |

SMELL-R (v1) - level 8 - ODD odor

| CID | Odor name | Dilution | CAS # |
|---|---|---|---|
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 87715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalatone | pure | 710-04-3 |
| 7583 | diphenyl ether | 1/1,000 | 101-84-8 |
| 8129 | heptanol | 1/1,000 | 111-70-6 |
| 31225 | phenethyl propionate | 1/100 | 122-70-3 |
| 7921 | gamma-valerolactone | 1/100 | 108-29-2 |
| 8094 | heptanoic acid | 1/10 | 111-14-8 |
| 1001 | phenethylamine | 1/1,000 | 64-04-0 |
| 8030 | thiophene | 1/1,000 | 110-02-1 |
| 8914 | nonanol | pure | 143-08-8 |
| 12741 | 2-decanone | 1/10 | 693-54-9 |
| 1068 | methyl sulfide | 1/1,000 | 75-18-3 |
| 7410 | acetophenone | 1/1,000 | 98-86-2 |
| 16324 | allyl butyrate | 1/1,000 | 2051-78-7 |
| 7335 | carvyl acetate | 1/1,000 | 97-42-7 |
| 89440 | 6-acetyl-1,1,2,4,4,7-hexamethyltetralin | 1/10 | 21145-77-7 |
| 9024 | α,α-dimethylphenethyl acetate | 1/10 | 151-05-3 |
| 660 | dihydrocoumarin | 1/100 | 119-84-6 |

SMELL-R (v1) - level 8 - CONTROL odor

| CID | Odor name | Dilution | CAS # |
|---|---|---|---|
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-65-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/100,000 | 110-62-3 |
| 1136 | 4-methyl-5-thiazoleethanol | 1/1,000 | 137-00-8 |
| 8007 | butylamine | 1/100,000 | 109-73-9 |
| 251531 | phenethyl 2-furoate | 1/100 | 7149-32-8 |
| 1060 | pyruvic acid | 1/100,000 | 127-17-3 |
| 60999 | benzyl phenylacetate | 1/100 | 102-16-9 |
| 11124 | methyl propionate | 1/1,000 | 554-12-1 |
| 454 | octanal | 1/1,000 | 124-13-0 |

SMELL-R (v1) - level 9 - ODD odor

| CID | Odor name | Dilution | CAS # |
|---|---|---|---|
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 31225 | phenethyl propionate | 1/100 | 122-70-3 |
| 7921 | gamma-valerolactone | 1/100 | 108-29-2 |
| 8094 | heptanoic acid | 1/10 | 111-14-8 |
| 1001 | phenethytamine | 1/1,000 | 64-04-0 |
| 8030 | thiophene | 1/1,000 | 110-02-1 |
| 8914 | nonanol | pure | 143-08-8 |
| 12741 | 2-decanone | 1/10 | 693-54-9 |
| 1068 | methyl sulfide | 1/1,000 | 75-18-3 |
| 7410 | acetophenone | 1/1,000 | 98-86-2 |
| 16324 | allyl butyrate | 1/1,000 | 2051-78-7 |
| 7335 | carvyl acetate | 1/1,000 | 97-42-7 |
| 89440 | 6-acetyl-1,1,2,4,4,7-hexamethyltetralin | 1/10 | 21145-77-7 |
| 9024 | α,α-dimethylphenethyl acetate | 1/10 | 151-05-3 |
| 660 | dihydrocoumarin | 1/100 | 119-84-6 |

SMELL-R (v1) - level 9 - CONTROL odor

| CID | Odor name | Dilution | CAS # |
|---|---|---|---|
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing the ODD odor. All mixtures have equal volumes of each component.

| CID | Odor name | Dilution | CAS # |
|---|---|---|---|
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/1,000 | 110-62-3 |
| 1136 | 4-methyl-5-thiazoleethanol | 1/1,000 | 137-00-8 |
| 8007 | butylamine | 1/1,000 | 109-73-9 |
| 251531 | phenethyl 2-furoate | 1/100 | 7149-32-8 |
| 1060 | pyruvic acid | 1/1,000 | 127-17-3 |
| 60999 | benzyl phenylacetate | 1/100 | 102-16-9 |
| 11124 | methyl propionate | 1/1,000 | 554-12-1 |
| 454 | octanal | 1/1,000 | 124-13-0 |
| SMELL-R (v1) - level 10 - ODD odor | | | |
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-187 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalatone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 8094 | heptanoic acid | 1/10 | 111-14-8 |
| 1001 | phenethylamine | 1/1,000 | 64-04-0 |
| 8030 | thiophene | 1/1,000 | 110-02-1 |
| 8914 | nonanol | pure | 143-08-8 |
| 12741 | 2-decanone | 1/10 | 693-54-9 |
| 1068 | methyl sulfide | 1/1,000 | 75-18-3 |
| 7410 | acetophenone | 1/1,000 | 98-86-2 |
| 16324 | allyl butyrate | 1/1,000 | 2051-78-7 |
| 7335 | carvyl acetate | 1/1,000 | 97-42-7 |
| 89440 | 6-acetyl-1,1,2,4,4,7-hexamethyltetralin | 1/10 | 21145-77-7 |
| 9024 | α,α-dimethylphenethyl acetate | 1/10 | 151-05-3 |
| 660 | dihydrocoumarin | 1/100 | 119-84-6 |
| SMELL-R (v1) - level 10 - CONTROL odor | | | |
| 7969 | benzenethiol | 1/100,000 | 108-98-5 |
| 7731 | 4-methylanisole | 1/1,000 | 104-988 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 60845-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-984 |
| 7144 | 2-methoxy-4-methylphenol | 1/100,000 | 93-51-6 |
| 8063 | valeraldehyde | 1/100,000 | 110-62-3 |
| 1136 | 4-methyl-5-thiazoleethanol | 1/1,000 | 137-00-8 |
| 8007 | butylamine | 1/100,000 | 109-73-9 |
| 251531 | phenethyl 2-furoate | 1/100 | 7149-32-8 |
| 1060 | pyruvic acid | 1/100,000 | 127-17-3 |
| 60999 | benzyl phenylacetate | 1/100 | 102-16-9 |
| 11124 | methyl propionate | 1/1,000 | 554-12-1 |
| 454 | octanal | 1/1,000 | 124-13-0 |
| SMELL-R (v1) - level 11 - ODD odor | | | |
| 7969 | benzenethiol | 1/100,000 | 408-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalatone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8030 | thiophene | 1/1,000 | 110-02-1 |
| 8914 | nonanol | pure | 143-08-8 |
| 12741 | 2-decanone | 1/10 | 693-54-9 |
| 1068 | methyl sulfide | 1/1,000 | 75-18-3 |
| 7410 | acetophenone | 1/1,000 | 98-86-2 |
| 16324 | allyl butyrate | 1/1,000 | 2051-78-7 |
| 7335 | carvyl acetate | 1/1,000 | 97-42-7 |
| 89440 | 6-acetyl-1,1,2,4,4,7-hexamethyltetralin | 1/10 | 21145-77-7 |
| 9024 | α,α-dimethylphenethyl acetate | 1/10 | 151-05-3 |
| 660 | dihydrocoumarin | 1/100 | 119-84-6 |
| SMELL-R (v1) - level 11 - CONTROL odor | | | |
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/100,000 | 110-62-3 |

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing the ODD odor. All mixtures have equal volumes of each component.

| CID | Odor name | Dilution | CAS # |
|---|---|---|---|
| 1136 | 4-methyl-5-thiazoleethanol | 1/1,000 | 137-00-8 |
| 8007 | butylamine | 1/100,000 | 109-73-9 |
| 251531 | phenethyl 2-furoate | 1/100 | 7149-32-8 |
| 1060 | pyruvic acid | 1/100,000 | 127-17-3 |
| 60999 | benzyl phenylacetate | 1/100 | 102-16-9 |
| 11124 | methyl propionate | 1/1,000 | 554-12-1 |
| 454 | octanal | 1/1,000 | 124-13-0 |

SMELL-R (v1) - level 12 - ODD odor

| CID | Odor name | Dilution | CAS # |
|---|---|---|---|
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 12741 | 2-decanone | 1/10 | 693-54-9 |
| 1068 | methyl sulfide | 1/1,000 | 75-18-3 |
| 7410 | acetophenone | 1/1,000 | 98-86-2 |
| 16324 | allyl butyrate | 1/1,000 | 2051-78-7 |
| 7335 | carvyl acetate | 1/1,000 | 97-42-7 |
| 89440 | 6-acetyl-1,1,2,4,4,7-hexamethyltetralin | 1/10 | 21145-77-7 |
| 9024 | α,α-dimethylphenethyl acetate | 1/10 | 151-05-3 |
| 660 | dihydrocoumarin | 1/100 | 119-84-6 |

SMELL-R (v1) - level 12 - CONTROL odor

| CID | Odor name | Dilution | CAS # |
|---|---|---|---|
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 3093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7963 | butyl butyrate | 1/1,000 | 109-21-7 |
| 519539 | 2-(1-methylpropyl)thiazole | 1/100,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/100,000 | 110-62-3 |
| 1136 | 4-methyl-5-thiazoleethanol | 1/1,000 | 137-00-8 |
| 8007 | butylamine | 1/100,000 | 109-73-9 |
| 251531 | phenethyl 2-furoate | 1/100 | 7149-32-8 |
| 1060 | pyruvic acid | 1/100,000 | 127-17-3 |
| 60999 | benzyl phenylacetate | 1/100 | 102-16-9 |
| 11124 | methyl propionate | 1/1,000 | 554-12-1 |
| 454 | octanal | 1/1,000 | 124-13-0 |

SMELL-R (v1) - level 13 - ODD odor

| CID | Odor name | Dilution | CAS # |
|---|---|---|---|
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalatone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/10 | 110-62-3 |
| 1136 | 4-methyl-5-thiazole | 1/1,000 | 137-00-8 |
| 7410 | acetophenone | 1/1,000 | 98-86-2 |
| 16324 | allyl butyrate | 1/1,000 | 2051-78-7 |
| 7335 | carvyl acetate | 1/1,000 | 97-42-7 |
| 89440 | 6-acetyl-1,1,2,4,4,7-hexamethyltetralin | 1/10 | 21145-77-7 |
| 9024 | α,α-dimethylphenethyl acetate | 1/10 | 151-05-3 |
| 660 | dihydrocoumarin | 1/100 | 119-84-6 |

SMELL-R (v1) - level 13 - CONTROL odor

| CID | Odor name | Dilution | CAS # |
|---|---|---|---|
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/100,000 | 110-62-3 |
| 1136 | 4-methyl-5-thiazoleethanol | 1/1,000 | 137-00-8 |
| 8007 | butylamine | 1/100,000 | 109-73-9 |
| 251531 | phenethyl 2-furoate | 1/100 | 7149-32-8 |
| 1060 | pyruvic acid | 1/100,000 | 127-17-3 |
| 60939 | benzyl phenylacetate | 1/100 | 102-169 |
| 11124 | methyl propionate | 1/1,000 | 554-12-1 |
| 454 | octanal | 1/1,000 | 124-13-0 |

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing the ODD odor. All mixtures have equal volumes of each component.

| CID | Odor name | Dilution | CAS # |
|---|---|---|---|
| SMELL-R (v1) - level 14 - ODD odor | | | |
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalatone | pure | 710-04-3 |
| 957 | octanol | 1/10 | 111-87-5 |
| 61177 | hexyl formate | 1/1,000 | 629-33-4 |
| 8174 | decano | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8062 | valeraldehyde | 1/10 | 110-62-3 |
| 1136 | 4-methyl-5-thiazole | 1/1,000 | 137-00-8 |
| 8007 | butylamine | 1/1,000 | 109-73-9 |
| 251531 | phenethyl 2-furoate | 1/1,000 | 7149-32-8 |
| 7335 | carvyl acetate | 1/1,000 | 97-42-7 |
| 89440 | 6-acetyl-1,1,2,4,4,7-hexamethyltetralin | 1/10 | 21145-77-7 |
| 9024 | α,α-dimethylphenethyl acetate | 1/10 | 151-05-3 |
| 660 | dihydrocoumarin | 1/100 | 119-84-6 |
| SMELL-R (v1) - level 14 - CONTROL odor | | | |
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/10 | 110-62-3 |
| 1136 | 4-methyl-5-thiazoleethanol | 1/1,000 | 137-00-8 |
| 8007 | butylamine | 1/100,000 | 109-73-9 |
| 251531 | phenethyl 2-furoate | 1/100 | 7149-32-8 |
| 1060 | pyruvic acid | 1/100,000 | 127-17-3 |
| 60999 | benzyl phenylacetate | 1/100 | 102-16-9 |
| 11124 | methyl propionate | 1/1,000 | 554-12-1 |
| 454 | octanal | 1/1,000 | 124-13-0 |
| SMELL-R (v1) - level 15 - ODD odor | | | |
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalatone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/10 | 110-62-3 |
| 1136 | 4-methyl-5-thiazole | 1/1,000 | 137-00-8 |
| 8007 | butylamine | 1/1,000 | 109-73-9 |
| 251531 | phenethyl 2-furoate | 1/1,000 | 17149-32-8 |
| 1060 | pyruvic acid | 1/1,000 | 127-17-3 |
| 60999 | benzyl phenylacetate | 1/10 | 102-16-9 |
| 9024 | α,α-dimethylphenethyl acetate | 1/10 | 151-05-3 |
| 660 | dihydrocoumarin | 1/100 | 119-84-6 |
| SMELL-R (v1) - level 15 - CONTROL odor | | | |
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-61-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/100,000 | 110-62-3 |
| 1136 | 4-methyl-5-thiazoleethanol | 1/1,000 | 137-00-8 |
| 8007 | butylamine | 1/100,000 | 109-73-9 |
| 251531 | phenethyl 2-furoate | 1/100 | 7149-32-8 |
| 1060 | pyruvic acid | 1/100,000 | 127-17-3 |
| 60999 | benzyl phenylacetate | 1/100 | 102-16-9 |
| 11124 | methyl propionate | 1/1,000 | 554-12-1 |
| 454 | octanal | 1/1,000 | 124-13-0 |
| SMELL-R (v1) - level 16 - ODD odor | | | |
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing the ODD odor. All mixtures have equal volumes of each component.

| CID | Odor name | Dilution | CAS # |
|---|---|---|---|
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalatone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-81-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/10 | 110-62-3 |
| 1136 | 4-methyl-5-thiazole | 1/1,000 | 137-00-8 |
| 8007 | butylamine | 1/1,000 | 109-73-9 |
| 251531 | phenethyl 2-furoate | 1/1,000 | 7149-32-8 |
| 1060 | pyruvic acid | 1/1,000 | 127-17-3 |
| 60999 | benzyl phenylacetate | 1/10 | 102-16-9 |
| 11124 | α,α-dimethylphenethyl acetate | 1/10 | 554-12-1 |
| 660 | dihydrocoumarin | 1/100 | 119-84-6 |
| | SMELL-R (v1) - level 16 - CONTROL odor | | |
| 7969 | benzenethiol | 1/100,000 | 108-98-5 |
| 7731 | 4-methylanisole | 1/1,000 | 104-93-8 |
| 13216 | decahydro-2-naphthol | 1/1,000 | 825-51-4 |
| 7770 | propyl butyrate | 1/1,000 | 105-66-8 |
| 8093 | 2-octanone | 1/1,000 | 111-13-7 |
| 7826 | methyl heptanoate | 1/1,000 | 106-73-0 |
| 7559 | methyl phenylacetate | 1/1,000 | 101-41-7 |
| 101010 | 2-methyl-4-propyl-1,3-oxathiane | 1/100,000 | 67715-80-4 |
| 6943 | 2-isopropylphenol | 1/1,000 | 88-69-7 |
| 22873 | hexyl hexanoate | 1/10 | 6378-65-0 |
| 61151 | methyl 2-methoxybenzoate | 1/100 | 606-45-1 |
| 7983 | butyl butyrate | 1/1,000 | 109-21-7 |
| 519539 | 2-(1-methylpropyl)thiazole | 1/100,000 | 18277-27-5 |
| 61204 | delta-undecalactone | pure | 710-04-3 |
| 957 | octanol | 1/10 | 111-87-5 |
| 61177 | hexyl formate | 1/1,000 | 629-33-4 |
| 8174 | decanol | 1/10 | 112-30-1 |
| 31266 | allyl hexanoate | 1/1,000 | 123-68-2 |
| 12097 | 5-methylfurfural | 1/1,000 | 620-02-0 |
| 521238 | 3-octyl acetate | 1/10 | 4864-81-3 |
| 8375 | 2-hydroxyacetophenone | 1/1,000 | 118-93-4 |
| 7144 | 2-methoxy-4-methylphenol | 1/100,000 | 93-51-6 |
| 8063 | valeraldehyde | 1/100,000 | 110-62-3 |
| 1136 | 4-methyl-5-thiazoleethanol | 1/1,000 | 137-00-8 |
| 8007 | butylamine | 1/100,000 | 109-73-9 |
| 251531 | phenethyl 2-furoate | 1/100 | 7149-32-8 |
| 1060 | pyruvic acid | 1/100,000 | 127-17-3 |
| 60999 | benzyl phenylacetate | 1/100 | 102-16-9 |
| 11124 | methyl propionate | 1/1,000 | 554-12-1 |
| 454 | octanal | 1/1,000 | 124-13-0 |
| | SMELL-R (v2) - Level 1 - ODD odor | | |
| 61005 | 2-phenoxyethyl isobutyrate | pure | 103-60-6 |
| 660 | dihydrocoumarin | 1/10 | 119-64-6 |
| 14257 | undecane | pure | 1120-21-4 |
| 62900 | whiskey lactone | 1/1,000 | 39212-23-2 |
| 7820 | dimethyl succinate | 1/10 | 106-65-0 |
| 61809 | 2-ethoxythiazole | 1/100,000 | 15679-19-3 |
| 454 | octanal | 1/1,000 | 124-13-0 |
| 61027 | butyl 10-undecenoate | pure | 109-42-2 |
| 7749 | ethyl propionate | 1/1,000 | 105-37-3 |
| 8797 | p-tolyl acetate | 1/10 | 140-39-6 |
| 7654 | phenethyl acetate | 1/10 | 103-45-7 |
| 12327 | ethyl undecanoate | 1/10 | 627-90-7 |
| 7793 | (−)-citronellol | 1/10 | 7540-51-4 |
| 61192 | 4-methyl-5-thiazoleethanol acetate | 1/1,000 | 656-53-1 |
| 246728 | 3-octanone | 1/1,000 | 106-68-3 |
| 16255 | Isoamyl octanoate | 1/10 | 2035-99-6 |
| 1136 | 4-methyl-5-thiazoteethanol | 1/1,000 | 137-00-8 |
| 8118 | propyl sulfide | 1/100,000 | 111-47-7 |
| 9589 | 3-acetylpyridine | 1/1,000 | 350-03-8 |
| 7632 | α,α-dimethylbenzenepropanal | 1/10 | 103-05-9 |
| 8082 | piperidine | 1/100,000 | 110-89-4 |
| 31265 | ethyl hexanoate | 1/100 | 123-66-0 |
| 17898 | 2-methoxy-3-methylpyrazine | 1/100,000 | 2847-30-5 |
| 7762 | ethyl butyrate | 1/1,000 | 105-54-4 |
| 8857 | ethyl acetate | 1/1,000 | 141-78-6 |
| 7799 | ethyl octanoate | pure | 106-32-1 |
| 104721 | 2-acetyl-3,5(6)-dimethylpyrazine | 1/1,000 | 54300-08-2 |
| 11902 | methyl 2-furoate | 1/1,000 | 611-13-2 |
| 11529 | butyl propionate | 1/1,000 | 590-01-2 |
| 9862 | 6-methyl-5-hepten-2-one | 1/1,000 | 110-93-0 |
| | SMELL-R (v2) - Level 1 - CONTROL odor | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-49-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxyhenzoate | 1/100 | 606-45-1 |
| 9609 | diethyl sulfide | 1/100,000 | 352-93-2 |
| 637568 | geraniol | 1/10 | 106-24-1 |
| 7803 | propyl propionate | 1/1,000 | 106-36-5 |
| 7409 | α-methylbenzyl alcohol | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentadecalactone | 1/10 | 106-02-5 |
| 7761 | diethyl malonate | 1/100 | 105-53-3 |
| 31244 | p-anisaldehyde | 1/1,000 | 123-11-5 |
| 16537 | terpinyl formate | 1/1,000 | 2153-26-6 |
| 7826 | methyl heptanoate | 1/1,000 | 106-73-0 |
| 7826 | methyl heptanoate | 1/1,000 | 106-73-0 |
| | SMELL-R (v2) - Level 2 - ODD odor | | |
| 8205 | lauryl acetate | 1/10 | 112-66-3 |
| 7770 | propyl butyrate | 1/1,000 | 105-66-8 |
| 14257 | undecane | pure | 1120-21-4 |
| 62900 | whiskey lactone | 1/1,000 | 39212-23-2 |
| 7820 | dimethyl succinate | 1/10 | 106-65-0 |
| 61809 | 2-ethoxythiazole | 1/1,000 | 15679-19-3 |
| 454 | octanal | 1/1,000 | 124-13-0 |
| 61027 | butyl 10-undecenoate | pure | 109-42-2 |
| 7749 | ethyl propionate | 1/1,000 | 105-37-3 |
| 8797 | p-tolyl acetate | 1/10 | 140-39-6 |
| 7654 | phenethyl acetate | 1/10 | 103-45-7 |
| 12327 | ethyl undecanoate | 1/10 | 627-90-7 |
| 7793 | (−)-citronellol | 1/10 | 7540-51-4 |
| 61192 | 4-methyl-5-thiazoleethanol acetate | 1/1,000 | 656-53-1 |
| 246728 | 3-octanone | 1/1,000 | 106-68-3 |
| 16255 | Isoamyl octanoate | 1/10 | 2035-99-6 |
| 1136 | 4-methyl-5-thiazoteethanol | 1/1,000 | 137-00-8 |

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing the ODD odor. All mixtures have equal volumes of each component.

| CID | Odor name | Dilution | CAS # |
|---|---|---|---|
| 8118 | propyl sulfide | 1/100,000 | 111-47-7 |
| 9589 | 3-acetylpyridine | 1/1,000 | 350-03-8 |
| 7632 | α,α-dimethylbenzenepropanal | 1/10 | 103-05-9 |
| 8082 | piperidine | 1/1,000 | 110-89-4 |
| 31265 | ethyl hexanoate | 1/100 | 123-66-0 |
| 17898 | 2-methoxy-3-methylpyrazine | 1/100,000 | 2847-30-5 |
| 7762 | ethyl butyrate | 1/1,000 | 105-54-4 |
| 8857 | ethyl acetate | 1/1,000 | 141-78-6 |
| 7799 | ethyl octanoate | pure | 106-32-1 |
| 104721 | 2-acetyl-3,5(6)-dimethylpyrazine | 1/1,000 | 54300-08-2 |
| 11902 | methyl 2-furoate | 1/1,000 | 611-13-2 |
| 11529 | butyl propionate | 1/1,000 | 590-01-2 |
| 9862 | 6-methyl-5-hepten-2-one | 1/1,000 | 110-93-0 |
| | SMELL-R (v2) - Level 2 - CONTROL odor | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxybenzoate | 1/100 | 606-45-1 |
| 9609 | diethyl sulfide | 1/100,000 | 352-93-2 |
| 637566 | geraniol | 1/10 | 106-24-1 |
| 7803 | propyl propionate | 1/1,000 | 106-36-5 |
| 7409 | α-methylbenzyl alcohol | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentadecalactone | 1/10 | 106-02-5 |
| 7761 | diethyl malonate | 1/100 | 105-53-3 |
| 31244 | p-anisaldehyde | 1/1,000 | 123-11-5 |
| 16537 | terpinyl formate | 1/1,000 | 2153-26-6 |
| 7826 | methyl heptanoate | 1/1,000 | 106-73-0 |
| | SMELL-R (v2) - Level 3 - ODD odor | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 7820 | dimethyl succinate | 1/10 | 106-65-0 |
| 61809 | 2-ethoxythiazole | 1/100,000 | 15679-19-3 |
| 454 | octanal | 1/1,000 | 124-13-0 |
| 61027 | butyl 10-undecenoate | pure | 109-42-2 |
| 7749 | ethyl propionate | 1/1,000 | 105-37-3 |
| 8797 | p-tolyl acetate | 1/1,000 | 140-39-6 |
| 7654 | phenethyl acetate | 1/10 | 103-45-7 |
| 12327 | ethyl undecanoate | 1/10 | 627-90-7 |
| 7793 | (−)-citronellol | 1/10 | 7540-51-4 |
| 61192 | 4-methyl-5-thiazoleethanol acetate | 1/1,000 | 656-534 |
| 246728 | 3-octanone | 1/1,000 | 106-68-3 |
| 16255 | Isoamyl octanoate | 1/1,000 | 2035-99-6 |
| 1136 | 4-methyl-5-thiazoteethanol | 1/1 | 137-00-8 |
| 8118 | propyl sulfide | 1/100,000 | 111-47-7 |
| 9589 | 3-acetylpyridine | 1/1,000 | 350-03-8 |
| 7632 | α,α-dimethylbenzenepropanal | 1/10 | 103-05-9 |
| 8082 | piperidine | 1/100,000 | 110-89-4 |
| 31265 | ethyl hexanoate | 1/100 | 123-66-0 |
| 17898 | 2-methoxy-3-methylpyrazine | 1/100,000 | 2847-30-5 |
| 7762 | ethyl butyrate | 1/1,000 | 105-54-4 |
| 8857 | ethyl acetate | 1/1,000 | 141-78-6 |
| 7799 | ethyl octanoate | pure | 106-32-1 |
| 104721 | 2-acetyl-3,5(6)-dimethylpyrazine | 1/1,000 | 54300-08-2 |
| 11902 | methyl 2-furoate | 1/1,000 | 611-13-2 |
| 11529 | butyl propionate | 1/1,000 | 590-01-2 |
| 9862 | 6-methyl-5-hepten-2-one | 1/1,000 | 110-93-0 |
| | SMELL-R (v2) - Level 3 - CONTROL odor | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxybenzoate | 1/100 | 606-45-1 |
| 9609 | diethyl sulfide | 1/100,000 | 352-93-2 |
| 637566 | geraniol | 1/10 | 106-24-1 |
| 7803 | propyl propionate | 1/1,000 | 106-36-5 |
| 7409 | α-methylbenzyl alcohol | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentadecalactone | 1/10 | 106-02-5 |
| 7761 | diethyl malonate | 1/100 | 105-53-3 |
| 31244 | p-anisaldehyde | 1/1,000 | 123-11-5 |
| 16537 | terpinyl formate | 1/1,000 | 2153-26-6 |
| 7826 | methyl heptanoate | 1/1,000 | 106-73-0 |
| | SMELL-R (v2) - Level 4 - ODD odor | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-96-5 |
| 454 | octanal | 1/1,000 | 124-13-0 |
| 61027 | butyl 10-undecenoate | pure | 109-42-2 |
| 7749 | ethyl propionate | 1/1,000 | 105-37-3 |
| 8797 | p-tolyl acetate | 1/1,000 | 140-39-6 |
| 7654 | phenethyl acetate | 1/10 | 103-45-7 |
| 12327 | ethyl undecanoate | 1/10 | 627-90-7 |
| 7793 | (−)-citronellol | 1/10 | 7540-51-4 |
| 61192 | 4-methyl-5-thiazoleethanol acetate | 1/1,000 | 656-53-1 |
| 246728 | 3-octanone | 1/1,000 | 106-68-3 |
| 16255 | Isoamyl octanoate | 1/1,000 | 2035-99-6 |
| 1136 | 4-methyl-5-thiazoteethanol | 1/1 | 137-00-8 |
| 8118 | propyl sulfide | 1/100,000 | 111-47-7 |
| 9589 | 3-acetylpyridine | 1/1,000 | 350-03-8 |
| 7632 | α,α-dimethylbenzenepropanal | 1/10 | 103-05-9 |
| 8082 | piperidine | 1/100,000 | 110-89-4 |
| 31265 | ethyl hexanoate | 1/100 | 123-66-0 |
| 17898 | 2-methoxy-3-methylpyrazine | 1/100,000 | 2847-30-5 |
| 7762 | ethyl butyrate | 1/1,000 | 105-54-4 |
| 8857 | ethyl acetate | 1/1,000 | 141-78-6 |
| 7799 | ethyl octanoate | pure | 106-32-1 |
| 104721 | 2-acetyl-3,5(6)-dimethylpyrazine | 1/1,000 | 54300-08-2 |

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing the ODD odor. All mixtures have equal volumes of each component.

| CID | Odor name | Dilution | CAS # |
|---|---|---|---|
| 11902 | methyl 2-furoate | 1/1,000 | 611-13-2 |
| 11529 | butyl propionate | 1/1,000 | 590-01-2 |
| 9862 | 6-methyl-5-hepten-2-one | 1/1,000 | 110-93-0 |
| | SMELL-R (v2) - Level 4 - CONTROL odor | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-040 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxybenzoate | 1/100 | 606-45-1 |
| 9609 | diethyl sulfide | 1/100,000 | 352-93-2 |
| 637566 | geraniol | 1/10 | 106-24-1 |
| 7803 | propyl propionate | 1/1,000 | 106-36-5 |
| 7409 | α-methylbenzyl alcohol | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentadecalactone | 1/10 | 106-02-5 |
| 7761 | diethyl malonate | 1/100 | 105-53-3 |
| 31244 | p-anisaldehyde | 1/1,000 | 123-11-5 |
| 16537 | terpinyl formate | 1/1,000 | 2153-26-6 |
| 7826 | methyl heptanoate | 1/1,000 | 106-73-0 |
| | SMELL-R (v2) - Level 5 - ODD odor | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 7749 | ethyl propionate | 1/1,000 | 105-37-3 |
| 8797 | p-tolyl acetate | 1/1,000 | 140-39-6 |
| 7654 | phenethyl acetate | 1/10 | 103-45-7 |
| 12327 | ethyl undecanoate | 1/10 | 627-90-7 |
| 7793 | (−)-citronellol | 1/10 | 7540-51-4 |
| 61192 | 4-methyl-5-thiazoleethanol acetate | 1/1,000 | 656-53-1 |
| 246728 | 3-octanone | 1/1,000 | 106-68-3 |
| 16255 | Isoamyl octanoate | 1/10 | 2035-99-6 |
| 1136 | 4-methyl-5-thiazoteethanol | 1/1,000 | 137-00-8 |
| 8118 | propyl sulfide | 1/100,000 | 111-47-7 |
| 9589 | 3-acetylpyridine | 1/1,000 | 350-03-8 |
| 7632 | α,α-dimethylbenzenepropanal | 1/10 | 103-05-9 |
| 8082 | piperidine | 1/100,000 | 110-89-4 |
| 31265 | ethyl hexanoate | 1/100 | 123-66-0 |
| 17898 | 2-methoxy-3-methylpyrazine | 1/100,000 | 2847-30-5 |
| 7762 | ethyl butyrate | 1/1,000 | 105-54-4 |
| 8857 | ethyl acetate | 1/1,000 | 141-78-6 |
| 7799 | ethyl octanoate | pure | 106-32-1 |
| 104721 | 2-acetyl-3,5(6)-dimethylpyrazine | 1/1,000 | 54300-08-2 |
| 11902 | methyl 2-furoate | 1/1,000 | 611-13-2 |
| 11529 | butyl propionate | 1/1,000 | 590-01-2 |
| 9862 | 6-methyl-5-hepten-2-one | 1/1,000 | 110-93-0 |
| | SMELL-R (v2) - Level 5 - CONTROL odor | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxybenzoate | 1/100 | 606-45-1 |
| 9609 | diethyl sulfide | 1/100,000 | 352-93-2 |
| 637566 | geraniol | 1/10 | 106-24-1 |
| 7803 | propyl propionate | 1/1,000 | 106-36-5 |
| 7409 | α-methylbenzyl alcohol | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentadecalactone | 1/10 | 106-02-5 |
| 7761 | diethyl malonate | 1/100 | 105-53-3 |
| 31244 | p-anisaldehyde | 1/1,000 | 123-11-5 |
| 16537 | terpinyl formate | 1/1,000 | 2153-26-6 |
| 7826 | methyl heptanoate | 1/1,000 | 106-73-0 |
| | SMELL-R (v2) - Level 6 - ODD odor | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-altylanisole | 1/1,000 | 140-67-0 |
| 8878 | allyl heptanoate | 1/1,000 | 142-19-8 |
| 7361 | furfuryl alcohol | 1/1,000 | 98-00-0 |
| 7654 | phenethyl acetate | 1/10 | 103-45-7 |
| 12327 | ethyl undecanoate | 1/10 | 627-90-7 |
| 7793 | (−)-citronellol | 1/10 | 7540-51-4 |
| 61192 | 4-methyl-5-thiazoleethanol acetate | 1/1,000 | 656-53-1 |
| 246728 | 3-octanone | 1/1,000 | 106-68-3 |
| 16255 | Isoamyl octanoate | 1/10 | 2035-99-6 |
| 1136 | 4-methyl-5-thiazoteethanol | 1/1,000 | 137-00-8 |
| 8118 | propyl sulfide | 1/100,000 | 111-47-7 |
| 9589 | 3-acetylpyridine | 1/1,000 | 350-03-8 |
| 7632 | α,α-dimethylbenzenepropanal | 1/10 | 103-05-9 |
| 8082 | piperidine | 1/100,000 | 110-89-4 |
| 31265 | ethyl hexanoate | 1/100 | 123-66-0 |
| 17898 | 2-methoxy-3-methylpyrazine | 1/100,000 | 2847-30-5 |
| 7762 | ethvf butyrate | 1/1,000 | 105-54-4 |
| 8857 | ethyl acetate | 1/1,000 | 141-78-6 |
| 7799 | ethyl octanoate | pure | 106-32-1 |
| 104721 | 2-acetyl-3,5(6)-dimethylpyrazine | 1/1,000 | 54300-08-2 |
| 11902 | methyl 2-furoate | 1/1,000 | 611-13-2 |
| 11529 | butyl propionate | 1/1,000 | 590-01-2 |
| 9862 | 6-methyl-5-hepten-2-one | 1/1,000 | 110-93-0 |
| | SMELL-R (v2) - Level 6 - CONTROL odor | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing the ODD odor. All mixtures have equal volumes of each component.

| CID | Odor name | Dilution | CAS # |
|---|---|---|---|
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 6048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/10 | 134-20-3 |
| 1001 | phenethylamine | 1/10 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxybenzoate | 1/100 | 606-45-1 |
| 9609 | diethyl sulfide | 1/100,000 | 352-93-2 |
| 637566 | geraniol | 1/10 | 106-24-1 |
| 7803 | propyl propionate | 1/1,000 | 106-36-5 |
| 7409 | α-methylbenzyl alcohol | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentadecalactone | 1/10 | 106-02-5 |
| 7761 | diethyl malonate | 1/100 | 105-53-3 |
| 31244 | p-anisaldehyde | 1/1,000 | 123-11-5 |
| 16537 | terpinyl formate | 1/1,000 | 2153-26-6 |
| 7826 | methyl heptanoate | 1/1,000 | 106-73-0 |

SMELL-R (v2) - Level 7 - ODD odor

| CID | Odor name | Dilution | CAS # |
|---|---|---|---|
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/1,000 | 142-19-8 |
| 7361 | furfuryl alcohol | 1/1,000 | 98-00-0 |
| 8635 | methyl anthranilate | 1/10 | 134-20-3 |
| 1001 | phenethylamine | 1/10 | 64-04-0 |
| 7793 | (−)-citronellol | 1/10 | 7540-51-4 |
| 61192 | 4-methyl-5-thiazoteethanol | 1/1,000 | 656-53-1 |
| 246728 | 3-octanone | 1/1,000 | 106-68-3 |
| 16255 | Isoamyl octanoate | 1/10 | 2035-99-6 |
| 1136 | 4-methyl-5-thiazoteethanol | 1/1,000 | 137-00-8 |
| 8118 | propyl sulfide | 1/100,000 | 111-47-7 |
| 9589 | 3-acetylpyridine | 1/1,000 | 350-03-8 |
| 7632 | α,α-dimethylbenzenepropanal | 1/10 | 103-05-9 |
| 8082 | piperidine | 1/100,000 | 110-89-4 |
| 31265 | ethyl hexanoate | 1/100 | 123-66-0 |
| 17898 | 2-methoxy-3-methylpyrazine | 1/100,000 | 2847-30-5 |
| 7762 | ethyl butyrate | 1/1,000 | 105-54-4 |
| 8857 | ethyl acetate | 1/1,000 | 141-78-6 |
| 7799 | ethyl octanoate | pure | 106-32-1 |
| 104721 | 2-acetyl-3,5(6)-dimethylpyrazine | 1/1,000 | 54300-08-2 |
| 11902 | methyl 2-furoate | 1/1,000 | 611-13-2 |
| 11529 | butyl propionate | 1/1,000 | 590-01-2 |
| 9862 | 6-methyl-5-hepten-2-one | 1/1,000 | 110-93-0 |

SMELL-R (v2) - Level 7 - CONTROL odor

| CID | Odor name | Dilution | CAS # |
|---|---|---|---|
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 10-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/10 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 12051-78-7 |
| 61151 | methyl 2-methoxybenzoate | 1/100 | 606-45-1 |
| 9609 | diethyl sulfide | 1/100,000 | 352-93-2 |
| 637566 | geraniol | 1/10 | 106-24-1 |
| 7803 | propyl propionate | 1/1,000 | 106-36-5 |
| 7409 | α-methylbenzyl alcohol | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentadecalactone | 1/10 | 106-02-5 |
| 7761 | diethyl malonate | 1/100 | 105-53-3 |
| 31244 | p-anisaldehyde | 1/1,000 | 123-11-5 |
| 16537 | terpinyl formate | 1/1,000 | 2153-26-6 |
| 7826 | methyl heptanoate | 1/1,000 | 106-73-0 |

SMELL-R (v2) - Level 8 - ODD odor

| CID | Odor name | Dilution | CAS # |
|---|---|---|---|
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/10 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 246728 | 3-octanone | 1/1,000 | 106-68-3 |
| 16255 | Isoamyl octanoate | 1/10 | 2035-99-6 |
| 1136 | 4-methyl-5-thiazoteethanol | 1/1,000 | 137-00-8 |
| 8118 | propyl sulfide | 1/100,000 | 111-47-7 |
| 9589 | 3-acetylpyridine | 1/1,000 | 350-03-8 |
| 7632 | α,α-dimethylbenzenepropanal | 1/10 | 103-05-9 |
| 8082 | piperidine | 1/100,000 | 110-89-4 |
| 31265 | ethyl hexanoate | 1/100 | 123-66-0 |
| 17898 | 2-methoxy-3-methylpyrazine | 1/100,000 | 2847-30-5 |
| 7762 | ethyl butyrate | 1/1,000 | 105-54-4 |
| 8857 | ethyl acetate | 1/1,000 | 141-78-6 |
| 7799 | ethyl octanoate | pure | 106-32-1 |
| 104721 | 2-acetyl-3,5(6)-dimethylpyrazine | 1/1,000 | 54300-08-2 |
| 11902 | methyl 2-furoate | 1/1,000 | 611-13-2 |
| 11529 | butyl propionate | 1/1,000 | 590-01-2 |
| 9862 | 6-methyl-5-hepten-2-one | 1/1,000 | 110-93-0 |

SMELL-R (v2) - Level 8 - CONTROL odor

| CID | Odor name | Dilution | CAS # |
|---|---|---|---|
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38- 3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/10 | 134-20-3 |
| 1001 | phenethylamine | 1/1,000 | 64-04-0 |
| 62374 | 4-oxoisophorone | 1/100 | 1125-21-9 |

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing the ODD odor. All mixtures have equal volumes of each component.

| CID | Odor name | Dilution | CAS # |
|---|---|---|---|
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxybenzoate | 1/100 | 606-45-1 |
| 9609 | diethyl sulfide | 1/100,000 | 352-93-2 |
| 637566 | geraniol | 1/10 | 106-24-1 |
| 7803 | propyl propionate | 1/1,000 | 106-36-5 |
| 7409 | α-methylbenzyl alcohol | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentadecalactone | 1/10 | 106-02-5 |
| 7761 | diethyl malonate | 1/100 | 105-53-3 |
| 31244 | p-anisaldehyde | 1/1,000 | 123-11-5 |
| 16537 | terpinyl formate | 1/1,000 | 2153-26-6 |
| 7826 | methyl heptanoate | 1/1,000 | 106-73-0 |
| SMELL-R (v2) - Level 9 - ODD odor | | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-57-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 1136 | 4-methyl-5-thiazoteethanol | 1/1,000 | 137-00-8 |
| 8118 | propyl sulfide | 1/100,000 | 111-47-7 |
| 9589 | 3-acetylpyridine | 1/1,000 | 350-03-8 |
| 7632 | α,α-dimethylbenzenepropanal | 1/10 | 103-05-9 |
| 8082 | piperidine | 1/100,000 | 110-89-4 |
| 31265 | ethyl hexanoate | 1/100 | 123-66-0 |
| 17898 | 2-methoxy-3-methylpyrazine | 1/100,000 | 2847-30-5 |
| 7762 | ethyl butyrate | 1/1,000 | 105-54-4 |
| 8857 | ethyl acetate | 1/1,000 | 141-78-6 |
| 7799 | ethyl octanoate | pure | 106-32-1 |
| 104721 | 2-acetyl-3,5(6)-dimethylpyrazine | 1/1,000 | 54300-08-2 |
| 11902 | methyl 2-furoate | 1/1,000 | 611-13-2 |
| 11529 | butyl propionate | 1/1,000 | 590-01-2 |
| 9862 | 6-methyl-5-hepten-2-one | 1/1,000 | 110-93-0 |
| SMELL-R (v2) - Level 9 - CONTROL odor | | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8043 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-57-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxybenzoate | 1/100 | 606-45-1 |
| 9609 | diethyl sulfide | 1/100,000 | 352-93-2 |
| 637566 | geraniol | 1/10 | 106-24-1 |
| 7803 | propyl propionate | 1/1,000 | 106-36-5 |
| 7409 | α-methylbenzyl alcohol | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentadecalactone | 1/10 | 106-02-5 |
| 7761 | diethyl malonate | 1/100 | 105-53-3 |
| 31244 | p-anisaldehyde | 1/1,000 | 123-11-5 |
| 16537 | terpinyl formate | 1/1,000 | 2153-26-6 |
| 7826 | methyl heptanoate | 1/1,000 | 106-73-0 |
| SMELL-R (v2) - Level 10 - ODD odor | | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | 4-methyl-5-thiazoteethanol | 1/100 | 606-45-1 |
| 9609 | propyl sulfide | 1/100,000 | 352-93-2 |
| 9589 | 3-acetylpyridine | 1/1,000 | 350-03-8 |
| 7632 | α,α-dimethylbenzenepropanal | 1/10 | 103-05-9 |
| 8082 | piperidine | 1/100,000 | 110-89-4 |
| 31265 | ethyl hexanoate | 1/100 | 123-66-0 |
| 17898 | 2-methoxy-3-methylpyrazine | 1/100,000 | 2847-30-5 |
| 7762 | ethyl butyrate | 1/1,000 | 105-54-4 |
| 8857 | ethyl acetate | 1/1,000 | 141-78-6 |
| 7799 | ethyl octanoate | pure | 106-32-1 |
| 104721 | 2-acetyl-3,5(6)-dimethylpyrazine | 1/1,000 | 54300-08-2 |
| 11902 | methyl 2-furoate | 1/1,000 | 611-13-2 |
| 11529 | butyl propionate | 1/1,000 | 590-01-2 |
| 9862 | 6-methyl-5-hepten-2-one | 1/1,000 | 110-93-0 |
| SMELL-R (v2) - Level 10 - CONTROL odor | | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxybenzoate | 1/100 | 606-45-1 |
| 9609 | diethyl sulfide | 1/100,000 | 352-93-2 |
| 637566 | geraniol | 1/10 | 106-24-1 |
| 7803 | propyl propionate | 1/1,000 | 106-36-5 |
| 7409 | α-methylbenzyl alcohol | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing the ODD odor. All mixtures have equal volumes of each component.

| CID | Odor name | Dilution | CAS # |
|---|---|---|---|
| 12348 | pentyl acetate | 1/1,000 | 628-63-7 |
| 7792 | 3,7-dimethyl-1-octanol | 1/1,000 | 106-21-8 |
| 235414 | omega-pentadecalactone | 1/10 | 106-02-5 |
| 7761 | diethyl malonate | 1/100 | 105-53-3 |
| 31244 | p-anisaldehyde | 1/1,000 | 123-11-5 |
| 16537 | terpinyl formate | 1/1,000 | 2153-26-6 |
| 7826 | methyl heptanoate | 1/1,000 | 106-73-0 |
| SMELL-R (v2) - Level 11 - ODD odor | | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxybenzoate | 1/100 | 606-45-1 |
| 9609 | diethyl sulfide | 1/100,000 | 352-93-2 |
| 637566 | geraniol | 1/1,000 | 106-24-1 |
| 7803 | propyl propionate | 1/1,000 | 106-36-5 |
| 8082 | piperidine | 1/100,000 | 110-89-4 |
| 31265 | ethyl hexanoate | 1/100 | 123-66-0 |
| 17898 | 2-methoxy-3-methylpyrazine | 1/100,000 | 2847-30-5 |
| 7762 | ethyl butyrate | 1/1,000 | 105-54-4 |
| 8857 | ethyl acetate | 1/1,000 | 141-78-6 |
| 7799 | ethyl octanoate | pure | 106-32-1 |
| 104721 | 2-acetyl-3,5(6)-dimethylpyrazine | 1/1,000 | 54300-08-2 |
| 11902 | methyl 2-furoate | 1/1,000 | 611-13-2 |
| 11529 | butyl propionate | 1/1,000 | 590-01-2 |
| 9862 | 6-methyl-5-hepten-2-one | 1/1,000 | 110-93-0 |
| SMELL-R (v2) - Level 11 - CONTROL odor | | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxybenzoate | 1/100 | 606-45-1 |
| 9609 | diethyl sulfide | 1/100,000 | 352-93-2 |
| 637566 | geraniol | 1/1,000 | 106-24-1 |
| 7803 | propyl propionate | 1/1,000 | 106-36-5 |
| 7409 | α-methylbenzyl alcohol | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentadecalactone | 1/10 | 106-02-5 |
| 7761 | diethyl malonate | 1/100 | 105-53-3 |
| 31244 | p-anisaldehyde | 1/1,000 | 123-11-5 |
| 16537 | terpinyl formate | 1/1,000 | 2153-26-6 |
| 7826 | methyl heptanoate | 1/1,000 | 106-73-0 |
| SMELL-R (v2) - Level 12 - ODD odor | | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxybenzoate | 1/100 | 606-45-1 |
| 9609 | diethyl sulfide | 1/100,000 | 352-93-2 |
| 637566 | geraniol | 1/1,000 | 106-24-1 |
| 7803 | propyl propionate | 1/1,000 | 106-36-5 |
| 7409 | α-methylbenzyl | 1/100 | 98-85-1 |
| 24020 | ethyl 2-methylbutyrate | 1/1,000 | 7452-79-1 |
| 17898 | 2-acetyl-5-methylfuran | 1/100,000 | 2847-30-5 |
| 7762 | pentyl acetate | 1/1,000 | 105-54-4 |
| 8857 | 3,7-dimethyl-1-octanol | 1/1,000 | 141-78-6 |
| 7799 | omega-pentade | pure | 106-32-1 |
| 104721 | diethyl malonate | 1/1,000 | 54300-08-2 |
| 11902 | p-anisaldehyde | 1/1,000 | 611-13-2 |
| 11529 | butyl propionate | 1/1,000 | 590-01-2 |
| 9862 | methyl heptanoate | 1/1,000 | 110-93-0 |
| SMELL-R (v2) - Level 12 - CONTROL odor | | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxybenzoate | 1/100 | 606-45-1 |
| 9609 | diethyl sulfide | 1/100,000 | 352-93-2 |
| 637566 | geraniol | 1/1,000 | 106-24-1 |
| 7803 | propyl propionate | 1/1,000 | 106-36-5 |
| 7409 | α-methylbenzyl alcohol | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentadecalactone | 1/10 | 106-02-5 |
| 7761 | diethyl malonate | 1/100 | 105-53-3 |
| 31244 | p-anisaldehyde | 1/1,000 | 123-11-5 |
| 16537 | terpinyl formate | 1/1,000 | 2153-26-6 |
| 7826 | methyl heptanoate | 1/1,000 | 106-73-0 |

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing the ODD odor. All mixtures have equal volumes of each component.

| CID | Odor name | Dilution | CAS # |
|---|---|---|---|
| SMELL-R (v2) - Level 13 - ODD odor | | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxyhenzoate | 1/100 | 606-45-1 |
| 9609 | diethyl sulfide | 1/100,000 | 352-93-2 |
| 637566 | geraniol | 1/1,000 | 106-24-1 |
| 7803 | propyl propionate | 1/1,000 | 106-36-5 |
| 7409 | α-methylbenzyl | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-637 |
| 8857 | 3,7-dimethyl-1-octanol | 1/1,000 | 141-78-6 |
| 7799 | omega-pentade | pure | 106-32-1 |
| 104721 | diethyl malonate | 1/1,000 | 54300-08-2 |
| 11902 | p-anisaldehyde | 1/1,000 | 611-13-2 |
| 11529 | butyl propionate | 1/1,000 | 590-01-2 |
| 9862 | methyl heptanoate | 1/1,000 | 110-93-0 |
| SMELL-R (v2) - Level 13 - CONTROL odor | | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxyhenzoate | 1/100 | 606-45-1 |
| 9609 | diethyl sulfide | 1/100,000 | 352-93-2 |
| 637566 | geraniol | 1/1,000 | 106-24-1 |
| 7803 | propyl propionate | 1/1,000 | 106-36-5 |
| 7409 | α-methylbenzyl alcohol | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentadecalactone | 1/10 | 106-02-5 |
| 7761 | diethyl malonate | 1/100 | 103-53-3 |
| 31244 | p-anisaldehyde | 1/1,000 | 123-11-5 |
| 16537 | terpinyl formate | 1/1,000 | 2153-26-6 |
| 7826 | methyl heptanoate | 1/1,000 | 106-73-0 |
| SMELL-R (v2) - Level 14 - ODD odor | | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxyhenzoate | 1/100 | 606-45-1 |
| 9609 | diethyl sulfide | 1/100,000 | 352-93-2 |
| 637566 | geraniol | 1/1,000 | 106-24-1 |
| 7803 | propyl propionate | 1/1,000 | 106-36-5 |
| 7409 | α-methylbenzyl | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentade | 1/10 | 106-02-5 |
| 104721 | diethyl malonate | 1/1,000 | 54300-08-2 |
| 11902 | p-anisaldehyde | 1/1,000 | 611-13-2 |
| 11529 | butyl propionate | 1/1,000 | 590-01-2 |
| 9862 | methyl heptanoate | 1/1,000 | 110-93-0 |
| SMELL-R (v2) - Level 14 - CONTROL odor | | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxyhenzoate | 1/100 | 606-45-1 |
| 9609 | diethyl sulfide | 1/100,000 | 352-93-2 |
| 637566 | geraniol | 1/1,000 | 106-24-1 |
| 7803 | propyl propionate | 1/1,000 | 106-36-5 |
| 7409 | α-methylbenzyl alcohol | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentadecalactone | 1/10 | 106-02-5 |
| 7761 | diethyl malonate | 1/100 | 105-53-3 |
| 31244 | p-anisaldehyde | 1/1,000 | 123-11-5 |
| 16537 | terpinyl formate | 1/1,000 | 2153-26-6 |
| 7826 | methyl heptanoate | 1/1,000 | 106-73-0 |
| SMELL-R (v2) - Level 15 - ODD odor | | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |

Table SMELL-R Combinations. This Table lists the composition of stimuli for all 16 levels of SMELL-R (v1) and SMELL-R (v2). In the triangle tests, the ODD odor is presented in a single vial, and the CONTROL odor is presented in two identical vials. The task is for the subject to sniff the three vials and select the one vial containing the ODD odor. All mixtures have equal volumes of each component.

| CID | Odor name | Dilution | CAS # |
|---|---|---|---|
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxyhenzoate | 1/100 | 606-45-1 |
| 9609 | diethyl sulfide | 1/100,000 | 352-93-2 |
| 637566 | geraniol | 1/1,000 | 106-24-1 |
| 7803 | propyl propionate | 1/1,000 | 106-36-5 |
| 7409 | α-methylbenzyl | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentade | 1/10 | 106-02-5 |
| 7761 | diethyl malonate | 1/100 | 105-53-3 |
| 31244 | p-anisaldehyde | 1/1,000 | 123-11-5 |
| 11529 | butyl propionate | 1/1,000 | 590-01-2 |
| 9862 | methyl heptanoate | 1/1,000 | 110-93-0 |
| SMELL-R (v2) - Level 15 - CONTROL odor | | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxyhenzoate | 1/100 | 606-45-1 |
| 9609 | diethyl sulfide | 1/100,000 | 352-93-2 |
| 637566 | geraniol | 1/1,000 | 106-24-1 |
| 7803 | propyl propionate | 1/1,000 | 106-36-5 |
| 7409 | α-methylbenzyl alcohol | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentadecalactone | 1/10 | 106-02-5 |
| 7761 | diethyl malonate | 1/100 | 105-53-3 |
| 31244 | p-anisaldehyde | 1/1,000 | 123-11-5 |
| 16537 | terpinyl formate | 1/1,000 | 2153-26-6 |
| 7826 | methyl heptanoate | 1/1,000 | 106-73-0 |
| SMELL-R (v2) - Level 16 - ODD odor | | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-57-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxyhenzoate | 1/100 | 606-45-1 |
| 9609 | diethyl sulfide | 1/100,000 | 352-93-2 |
| 637566 | geraniol | 1/1,000 | 106-24-1 |
| 7803 | propyl propionate | 1/1,000 | 106-36-5 |
| 7409 | α-methylbenzyl | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentade | 1/10 | 106-02-5 |
| 7761 | diethyl malonate | 1/100 | 105-53-3 |
| 31244 | p-anisaldehyde | 1/1,000 | 123-11-5 |
| 16537 | terpinyl formate | 1/1,000 | 2153-26-6 |
| 9862 | 6-methyl-5-hepten-2-one | 1/1,000 | 110-93-0 |
| SMELL-R (v2) - Level 16 - CONTROL odor | | | |
| 8205 | lauryl acetate | 1/10 | 112-66-3 |
| 7770 | propyl butyrate | 1/1,000 | 105-66-8 |
| 7797 | ethyl heptanoate | 1/100 | 106-30-9 |
| 8049 | diethyl sebacate | pure | 110-40-7 |
| 14491 | 1,6-hexanedithiol | 1/100,000 | 1191-43-1 |
| 62144 | 2-furanmethanethiol formate | 1/100,000 | 59020-90-5 |
| 8048 | ethyl decanoate | 1/10 | 110-38-3 |
| 8815 | 4-allylanisole | 1/1,000 | 140-67-0 |
| 8878 | allyl heptanoate | 1/100 | 142-19-8 |
| 7361 | furfuryl alcohol | 1/1,000 | 98-00-0 |
| 8635 | methyl anthranilate | 1/100 | 134-20-3 |
| 1001 | phenethylamine | 1/1,000 | 64-04-0 |
| 62374 | 4-oxoisophorone | 1/100 | 1125-21-9 |
| 326 | cuminaldehyde | 1/1,000 | 122-03-2 |
| 61527 | 3-acetyl-2,5-dimethylfuran | 1/100,000 | 10599-70-9 |
| 16324 | allyl butyrate | 1/1,000 | 2051-78-7 |
| 61151 | methyl 2-methoxyhenzoate | 1/100 | 606-45-1 |
| 9609 | diethyl sulfide | 1/100,000 | 352-93-2 |
| 637566 | geraniol | 1/1,000 | 106-24-1 |
| 7803 | propyl propionate | 1/1,000 | 106-36-5 |
| 7409 | α-methylbenzyl | 1/100 | 98-85-1 |
| 24020 | ethyl 2-methylbutyrate | 1/1,000 | 7452-79-1 |
| 14514 | 2-acetyl-5-methylfuran | 1/1,000 | 1193-79-9 |
| 12348 | pentyl acetate | 1/1,000 | 628-63-7 |
| 7792 | 3,7-dimethyl-1-octanol | 1/1,000 | 106-21-8 |
| 235414 | omega-pentade | 1/10 | 106-02-5 |
| 7761 | diethyl malonate | 1/100 | 105-53-3 |
| 31244 | p-anisaldehyde | 1/1,000 | 123-11-5 |
| 16537 | terpinyl formate | 1/1,000 | 2153-26-6 |
| 7826 | methyl heptanoate | 1/1,000 | 106-73-0 |

REFERENCES

This reference listing is not an indication that any of the references is material to patentability.

1. Bramerson A, Johansson L, Ek L, Nordin S, & Bende M (2004) Prevalence of olfactory dysfunction: the skovde population-based study. *Laryngoscope* 114(4):733-737.
2. Vennemann M M, Hummel T, & Berger K (2008) The association between smoking and smell and taste impairment in the general population. *J Neurol* 255(8):1121-1126.
3. Liu G, Zong G, Doty R L, & Sun Q (2016) Prevalence and risk factors of taste and smell impairment in a nationwide representative sample of the US population: a cross-sectional study. *BMJ Open* 6(11):e013246.

4. Hummel T & Nordin S (2005) Olfactory disorders and their consequences for quality of life. *Acta Otolaryngol* 125(2):116-121.
5. Keller A & Malaspina D (2013) Hidden consequences of olfactory dysfunction: a patient report series. *BMC Ear Nose Throat Disord* 13(1):8.
6. Leopold D A, Hornung D E, & Schwob J E (1992) Congenital lack of olfactory ability. *Ann Otol Rhinol Laryngol* 101(3):229-236.
7. Karstensen H G & Tommerup N (2012) Isolated and syndromic forms of congenital anosmia. *Clin Genet* 81(3):210-215.
8. Temmel A F, et al. (2002) Characteristics of olfactory disorders in relation to major causes of olfactory loss. *Arch Otolaryngol Head Neck Surg* 128(6):635-641.
9. Devanand D P, et al. (2015) Olfactory deficits predict cognitive decline and Alzheimer dementia in an urban community. *Neurology* 84(2):182-189.
10. Brookmeyer R, Gray S, & Kawas C (1998) Projections of Alzheimer's disease in the United States and the public health impact of delaying disease onset. *Am J Public Health* 88(9):1337-1342.
11. Sindhusake D, et al. (2001) Validation of self-reported hearing loss. The Blue Mountains Hearing Study. *Int J Epidemiol* 30(6):1371-1378.
12. Sorokowska A, Drechsler E, Karwowski M, & Hummel T (2017) Effects of olfactory training: a meta-analysis. *Rhinology* 55(1):17-26.
13. Nguyen D T, Rumeau C, Gallet P, & Jankowski R (2016) Olfactory exploration: State of the art. *Eur Ann Otorhinolaryngol Head Neck Dis* 133(2): 113-118.
14. Amoore J E (1967) Specific anosmia: a clue to the olfactory code. *Nature* 214(93):1095-1098.
15. Bremner E A, Mainland J D, Khan R M, & Sobel N (2003) The prevalence of androstenone anosmia. *Chem Senses* 28(5):423-432.
16. Keller A, Hempstead M, Gomez I A, Gilbert A N, & Vosshall L B (2012) An olfactory demography of a diverse metropolitan population. *BMC Neurosci* 13:122.
17. Zernecke R, et al. (2011) Correlation analyses of detection thresholds of four different odorants. *Rhinology* 49(3):331-336.
18. Jiang R S, et al. (2010) A pilot study of a traditional Chinese version of the University of Pennsylvania Smell Identification Test for application in Taiwan. *Am J Rhinol Allergy* 24(1):45-50.
19. Rabin M D (1988) Experience facilitates olfactory quality discrimination. *Percept Psychophys* 44:532-540.
20. Jehl C, Royet J P, & Holley A (1995) Odor discrimination and recognition memory as a function of familiarization. *Percept Psychophys* 57(1002-1011).
21. Weiss T, et al. (2012) Perceptual convergence of multi-component mixtures in olfaction implies an olfactory white. *Proc Natl Acad Sci USA* 109(49):19959-19964.
22. Bushdid C, Magnasco M O, Vosshall L B, & Keller A (2014) Humans can discriminate more than 1 trillion olfactory stimuli. *Science* 343(6177):1370-1372.
23. Hummel T, Sekinger B, Wolf S R, Pauli E, & Kobal G (1997) 'Sniffin' sticks': olfactory performance assessed by the combined testing of odor identification, odor discrimination and olfactory threshold. *Chem Senses* 22(1):39-52.
24. Bates B T, Zhang S, Dufek J S, & Chen F C (1996) The effects of sample size and variability on the correlation coefficient. *Med Sci Sports Exerc* 28(3):386-391.
25. Kobal G, et al. (1996) "Sniffin' sticks": screening of olfactory performance. *Rhinology* 34(4):222-226.
26. Oleszkiewicz A, Pellegrino R, Pusch K, Margot C, & Hummel T (2017) Chemical complexity of odors increases reliability of olfactory threshold testing. *Sci Rep* 7:39977.
27. Ruopp M D, Perkins N J, Whitcomb B W, & Schisterman E F (2008) Youden Index and optimal cut-point estimated from observations affected by a lower limit of detection. *Biom J* 50(3):419-430.
28. Croy I, et al. (2015) Peripheral adaptive filtering in human olfaction? Three studies on prevalence and effects of olfactory training in specific anosmia in more than 1600 participants. *Cortex* 73:180-187.
29. Doty R L (2006) Olfactory dysfunction and its measurement in the clinic and workplace. *Int Arch Occup Environ Health* 79(4):268-282.
30. Laska M & Hudson R (1991) A comparison of the detection thresholds of odour mixtures and their components. *Chem Senses* 16(6):651-662.
31. Shu C H, Yuan B C, Lin S H, & Lin C Z (2007) Cross-cultural application of the "Sniffin' Sticks" odor identification test. *Am J Rhinol* 21(5):570-573.
32. Fornazieri M A, et al. (2015) Development of normative data for the Brazilian adaptation of the University of Pennsylvania Smell Identification Test. *Chem Senses* 40(2):141-149.
33. Li W, Howard J D, & Gottfried J A (2010) Disruption of odour quality coding in piriform cortex mediates olfactory deficits in Alzheimer's disease. *Brain* 133(9):2714-2726.
34. Chapuis J, et al. (2013) Lateral entorhinal modulation of piriform cortical activity and fine odor discrimination. *J Neurosci* 33(33):13449-13459.
35. Khan U A, et al. (2014) Molecular drivers and cortical spread of lateral entorhinal cortex dysfunction in preclinical Alzheimer's disease. *Nat Neurosci* 17(2):304-311.
36. Doty R L, Reyes P F, & Gregor T (1987) Presence of both odor identification and detection deficits in Alzheimer's disease. *Brain Res Bull* 18(5):597-600.
37. Kost R G, Corregano L M, Rainer T L, Melendez C, & Coller B S (2015) A data-rich recruitment core to support translational clinical research. *Clin Transl Sci* 8(2):91-99.
38. Keller A & Vosshall L B (2016) Olfactory perception of chemically diverse molecules. *BMC Neurosci* 17(1):55.
39. Doty R L (1975) Intranasal trigeminal detection of chemical vapors by humans. *Physiol Behav* 14(6):855-859.
40. Doty R L, et al. (1978) Intranasal trigeminal stimulation from odorous volatiles: psychometric responses from anosmic and normal humans. *Physiol Behav* 20(2):175-185.
41. Kobal G, Van Toller S, & Hummel T (1989) Is there directional smelling? *Experientia* 45(2): 130-132.
42. Croy I, et al. (2014) Human olfactory lateralization requires trigeminal activation. *Neuroimage* 98:289-295.
43. Doty R L, Shaman P, & Dann M (1984) Development of the University of Pennsylvania Smell Identification Test: a standardized microencapsulated test of olfactory function. *Physiol Behav* 32(3):489-502.
44. Albrecht J, et al. (2008) Test-retest reliability of the olfactory detection threshold test of the Sniffin' sticks. *Chem Senses* 33(5):461-467.
45. Deems D A, et al. (1991) Smell and taste disorders, a study of 750 patients from the University of Pennsylvania Smell and Taste Center. *Arch Otolaryngol Head Neck Surg* 117(5):519-528.

46. Doty R L, Deems D A, & Stellar S (1988) Olfactory dysfunction in parkinsonism: a general deficit unrelated to neurologic signs, disease stage, or disease duration. *Neurology* 38(8): 1237-1244.

47. Schwartz B S, Doty R L, Monroe C, Frye R, & Barker S (1989) Olfactory function in chemical workers exposed to acrylate and methacrylate vapors. *Am J Public Health* 79(5):613-618.

Although the present disclosure has been described with respect to one or more particular embodiments and/or examples, it will be understood that other embodiments and/or examples of the present disclosure may be made without departing from the scope of the present disclosure.

The invention claimed is:

1. A method comprising allowing an individual to nasally inhale odors produced by a combination comprising all of: Heptanol, methyl heptanoate, 2-octanone, ethyl butyrate, methyl anthranilate, 2-decanone, Octanal, butyl butyrate, 3-octanone, allyl heptanoate, allyl hexanoate, butyl propionate, 6-methyl-5-hepten-2-one, methyl 2-furoate, delta-undecalactone, 2-ethylhexanol, whiskey lactone, Isoamyl butyrate, and phenethyl acetate, and determining whether or not the individual perceives an odor from the combination of the compounds.

2. The method of claim 1, wherein the individual perceives the odor, the method further comprising allowing the individual to compare perception of the odor to at least one control, wherein the control is devoid of one, some or all of the compounds.

3. The method of claim 2, wherein the individual perceives the odor, the method further comprising subsequently allowing the individual to nasally inhale odors produced by a dilution of the combination of compounds, and determining whether or not the individual perceives an odor from the dilution of the combination of the compounds, and optionally repeating said method with one or more serial dilutions of the combinations of the compounds until the individual does not percieve the odor, and generating a threshold value for olfactory sensitivity from a change in perception.

* * * * *